(12) United States Patent
Binggeli et al.

(10) Patent No.: US 6,673,795 B2
(45) Date of Patent: Jan. 6, 2004

(54) PYRIMIDINE, PYRAZINE AND TRIAZANE DERIVATIVES

(75) Inventors: Alfred Binggeli, Binningen (CH);
Hans-Peter Maerki, Basel (CH);
Thierry Masquelin, Kembs (FR);
Vincent Mutel, Brunstatt (FR);
Maurice Wilhelm, Morschwiller le Bas (FR); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/157,338

(22) Filed: May 29, 2002

(65) Prior Publication Data

US 2003/0060466 A1 Mar. 27, 2003

(30) Foreign Application Priority Data

Jun. 1, 2001 (EP) .............................. 01113379

(51) Int. Cl.[7] .................... C07D 241/26; C07D 401/04; C07D 401/14; A61K 31/4995; A61P 25/00
(52) U.S. Cl. ............ 514/242; 514/252.11; 514/255.05; 514/256; 514/272; 514/274; 544/182; 544/295; 544/319; 544/326; 544/408
(58) Field of Search ............................ 514/242, 252.11, 514/255.05, 272, 274, 256; 544/182, 295, 319, 326, 408

(56) References Cited

FOREIGN PATENT DOCUMENTS

AG           1 074 549 A2        2/2001

OTHER PUBLICATIONS

Monn, J.A. et al, Ann. Reports Med. Chem., 35, 2000, 1–10.*
R. G. Jones, J. Amer. Chem. Soc., 71, pp. 78–81 (1949).
Taylor et al., J. Org. Chem., 40, pp. 2341–2347 (1975).
J. J. Huang, J. Org. Chem., 50, pp. 2293–2298 (1985).
Taylor et al., J. Org. Chem., 37, pp. 3958–3960 (1972).

* cited by examiner

Primary Examiner—Mukund J. Shah
Assistant Examiner—Thomas McKenzie
(74) Attorney, Agent, or Firm—George W. Johnston; Patricia S. Rocha-Tramaloni; Kimberly J. Prior

(57) ABSTRACT

The present invention is a pyrimidine, triazine or pyrazine derivative of the formula

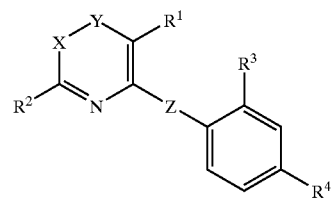

or a pharmaceutically acceptable salt thereof wherein $R^1$, $R^2$, $R^3$, $R^4$, X, Y and Z are as defined in the specification. The invention is a pharmaceutical composition containing an effective amount of the compound of formula 1, its preparation and to a method of treatment, control or prevention of acute and/or chronic neurological disorders by administering a therapeutically effective amount of a compound of formula 1.

38 Claims, No Drawings

PYRIMIDINE, PYRAZINE AND TRIAZANE DERIVATIVES

FIELD OF INVENTION

The present invention relates to pyrimidine, triazine and pyrazine derivatives of the formula

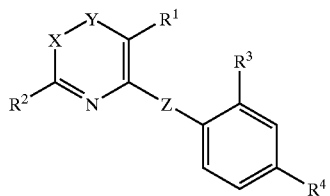

Compounds of formula I are metabotropic glutamate (mGluR 1) receptor antagonists and are useful in the treatment of disorders responsive to mediation of the mGluR 1 receptors, such as acute and/or chronic neurological disorders

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) belong to the second main group and, furthermore, belong to the family of G-protein-coupled receptors.

At present, eight different members of these mGluRs are known and of these some even have sub-types. On the basis of structural parameters, the different second messenger signaling pathways and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as epilepsy, stroke, chronic and acute pain, psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depression

SUMMARY OF THE INVENTION

The present invention is a compound of formula

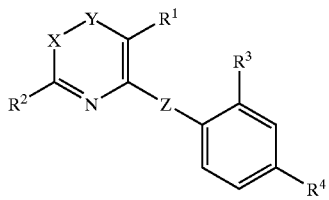

I or a pharmaceutically acceptable salt thereof wherein
$R^1$ is selected from the group consisting of nitro and cyano;
$R^2$ is selected from the group consisting of hydrogen, $(C_1-C_7)$-alkyl and $-NHR^{10}$, and wherein
$R^{10}$ is selected from the group consisting of hydrogen, $(C_1-C_7)$-alkyl, $-(CH_2)_m-OR^{11}$, $-(CH_2)_p-(C_3-C_6)$-cycloalkyl, $-(CH_2)_m-NH-C(O)O-(C_1-C_7)$-alkyl, and $-(CH_2)_p$-pyridyl and $R^{11}$ is selected from the group consisting of hydrogen and $(C_1-C_7)$-alkyl;
$R^3$ is selected from the group consisting of hydrogen, $(C_1-C_7)$-alkyl, fluoro, hydroxy, $(C_1-C_7)$-alkoxy, $(C_1-C_7)$-alkylthio, cyano and nitro;
$R^4$ is selected from the group consisting of hydrogen and fluoro;

is selected from the group consisting of

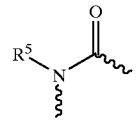

(a)

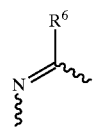

(b)

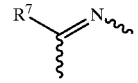

(c)

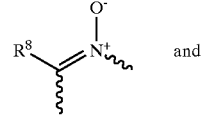

(d)

and

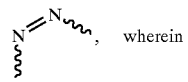

(e)

, wherein $R^5$ is selected from the group consisting of hydrogen, $(C_1-C_7)$-alkyl, $(C_1-C_7)$-alkenyl, $-(CH_2)_m-OR^{11}$, fluoro-$(C_1-C_7)$-alkyl and $-(CH_2)_n CN$;
$R^6$ is selected from the group consisting of $(C_1-C_7)$-alkyl, halogen, hydroxy, $(C_1-C_7)$-alkoxy, $(C_1-C_7)$-alkylthio, —O—(CH$_2$)$_m$—OR$^{11}$, —O-fluoro-(C$_1$–C$_7$)-alkyl and —NHR$^{12}$, and R$^{12}$ is selected from the group consisting of (C$_1$–C$_7$)-alkyl, —(CH$_2$)$_m$—OR$^{11}$, —(CH$_2$)$_p$—(C$_3$–C$_6$)-cycloalkyl and —(CH$_2$)$_p$-pyridyl;

R$^7$ is selected from the group consisting of hydrogen, (C$_1$–C$_7$)-alkyl and phenyl;

R$^8$ is selected from the group consisting of hydrogen, (C$_1$–C$_7$)-alkyl and phenyl;

Z is selected from the group consisting of

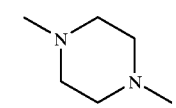
(i)

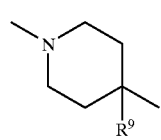
(ii)
and

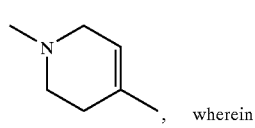
(iii)
, wherein

R$^9$ is selected from the group consisting of hydrogen, hydroxy and cyano;

m is independently from each other in each occurrence 2, 3, 4, 5 or 6;

n is independently from each other in each occurrence 1, 2, 3, 4, 5 or 6; and p is independently from each other in each occurrence 0, 1, 2, 3, 4, 5 or 6.

It has now been found that the compounds of formula I are antagonists of the metabotropic glutamate receptor.

Objects of the present invention are compounds of formula I or pharmaceutically acceptable salts thereof and their use as pharmaceutically active substances. Methods for the preparation of the above mentioned substances and pharmaceutical compositions based on compounds of formula I and their production are also objects of the present invention. The invention also is a method of treatment of conditions responsive to mediation of group I mGluR receptors comprising administering a therapeutically effective amount of a compound of formula I or a pharmaceutically acceptable salt thereof to a person in need of such treatment.

DETAILED DESCRIPTION

A preferred compound of formula I within the scope of the present invention has the formula

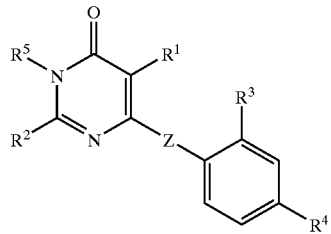
Ia or a pharmaceutically acceptable salt thereof, wherein

R$^1$ is selected from the group nitro and cyano;

R$^2$ is selected from the group consisting of hydrogen, (C$_1$–C$_7$)-alkyl and —NHR$^{10}$, and wherein R$^{10}$ is selected from the group consisting of hydrogen, (C$_1$–C$_7$)-alkyl, —(CH$_2$)$_m$—OR$^{11}$, —(CH$_2$)$_p$—(C$_3$–C$_6$)-cycloalkyl, —(CH$_2$)$_m$—NH—C(O)O—(C$_1$–C$_7$)-alkyl and —(CH$_2$)$_p$-pyridyl; wherein R$^{11}$ is hydrogen or (C$_1$–C$_7$)-alkyl;

R$^3$ is selected from the group consisting of hydrogen, (C$_1$–C$_7$)-alkyl, fluoro, hydroxy, (C$_1$–C$_7$)-alkoxy, (C$_1$–C$_7$)-alkylthio, cyano and nitro;

R$^4$ is hydrogen or fluoro;

R$^5$ is selected from the group consisting of hydrogen, (C$_1$–C$_7$)-alkyl, (C$_1$–C$_7$)-alkenyl, —(CH$_2$)$_m$—OR$^{11}$, fluoro-(C$_1$–C$_7$)-alkyl and —(CH$_2$)$_n$—CN;

Z is selected from the group consisting of

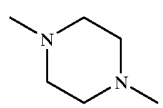
(i)

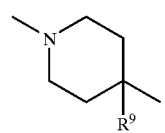
(ii)
and

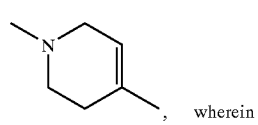
(iii)
, wherein

R$^9$ is selected from the group consisting of hydrogen, hydroxy and cyano;

m is independently from each other in each occurrence 2, 3, 4, 5 or 6;

n is independently from each other in each occurrence 1, 2, 3, 4, 5 or 6; and p is independently from each other in each occurrence 0, 1, 2, 3, 4, 5 or 6.

A further preferred compound of formula Ia has the formula

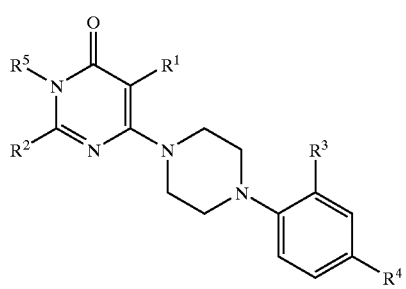
Ia1 wherein $R^2$ is lower alkyl and $R^5$ is selected from the group consisting of $(C_1-C_7)$-alkyl, $(C_1-C_7)$-alkyl subsituted by halo and $(C_1-C_7)$-alkyl substituted by hydroxyl.

A preferred compound of formula Ia1 is selected from the group consisting of 6-[4-(4-Fluoro-phenyl)-piperazin-1-yl]-2-methyl-5-nitro-3-(2,2,2-trifluoro-ethyl)-3H-pyrimidin-4-one;

3-ethyl-6-[4-(4-fluoro-phenyl)-piperazin-1-yl]-2-methyl-5-nitro-3H-pyrimidin-4-one; and 6-[4-(4-fluoro-phenyl)-piperazin-1-yl]-3-(2-hydroxy-ethyl)-2-methyl-5-nitro-3H-pyrimidin-4-one.

Another preferred compound of formula Ia has the formula

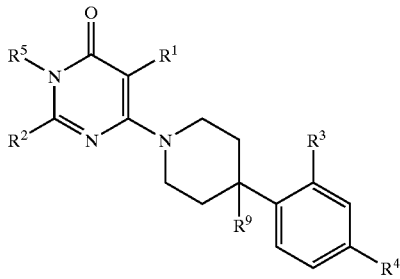

Ia2 wherein $R^2$ is selected from the group consisting of $(C_1-C_7)$-alkyl and —$NHR^{10}$, wherein $R^{10}$ is selected from the group consisting of $(C_1-C_7)$-alkyl, —$(CH_2)_m$—$OR^{11}$, —$(CH_2)_p$—$(C_3-C_6)$-cycloalkyl, and $R^{11}$ is selected from the group consisting of hydrogen and $(C_1-C_7)$-alkyl, —$(CH_2)_m$—NH—C(O)O—$(C_1-C_7)$-alkyl and —$(CH_2)_p$-pyridyl;

$R^3$ is selected from the group consisting of hydrogen and fluoro; and wherein $R^9$ is hydrogen.

A more preferred compound of formula Ia2 is wherein $R^3$ is hydrogen and $R^5$ is selected from the group consisting of $(C_1-C_7)$-alkyl, —$(CH_2)_m$—$OR^{11}$ and fluoro-$(C_1-C_7)$-alkyl.

An exemplary more preferred compound of formula Ia2 is selected from the group consisting of 6-[4-(4-fluoro-phenyl)-piperidin-1-yl]-2-methyl-5-nitro-3-(2,2,2-trifluoro-ethyl)-3H-pyrimidin-4-one, 2-methyl-5-nitro-6-(4-phenyl-piperidin-1-yl)-3-(2,2,2-trifluoro-ethyl)-3H-pyrimidin-4-one, and 6-[4-(4-fluoro-phenyl)-piperidin-1-yl]-3-(2-methoxy-ethyl)-2-methyl-5-nitro-3H-pyrimidin-4-one.

An additional preferred compound of formula I has the formula

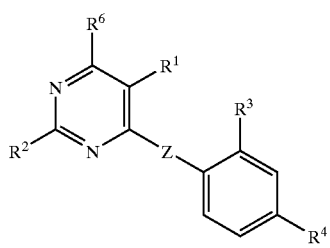

Ib or a pharmaceutically acceptable salt thereof.

A further preferred compound of formula Ib has the formula

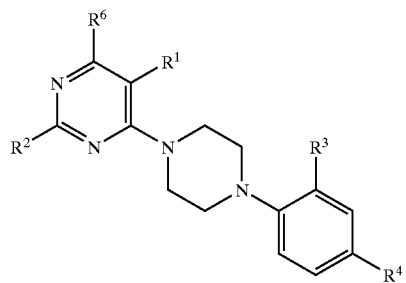

Ib1 wherein
$R^2$ is selected from the group consisting of $(C_1-C_7)$-alkyl and —$NHR^{10}$; and
$R^{10}$ is selected from the group consisting of $(C_1-C_7)$-alkyl, —$(CH_2)_m$—$OR^{11}$, —$(CH_2)_p$—$(C_3-C_6)$-cycloalkyl, and $R^{11}$ is selected from the group consisting of hydrogen, $(C_1-C_7)$-alkyl, —$(CH_2)_m$—NH—C(O)O—$(C_1-C_7)$-alkyl and —$(CH_2)_p$-pyridyl;
$R^3$ is selected from the group consisting of hydrogen and fluoro;
$R^6$ is selected from the group consisting of halogen, $(C_1-C_7)$-alkoxy, $(C_1-C_7)$-alkylthio, —O—$(CH_2)_m$—$OR^{11}$, —O-fluoro-$(C_1-C_7)$-alkyl and —$NHR^{12}$; and
$R^{12}$ is selected from the group consisting of $(C_1-C_7)$-alkyl, —$(CH_2)_m$—OR and —$(CH_2)_p$—$(C_3-C_6)$-cycloalkyl.

An exemplary preferred compound of formula Ib1 is selected from the group consisting of 2-(cyclopropylmethyl-amino)-4-[4-(4-fluoro-phenyl)-piperazin-1-yl]-6-(2-hydroxy-ethylamino)-pyrimidine-5-carbonitrile, 2-(cyclopropylmethyl-amino)-4-(2-hydroxy-ethylamino)-6-(4-phenyl-piperazin-1-yl)-pyrimidine-5-carbonitrile, 2-caclopropylamino-4-[4-(4-fluoro-phenyl)-piperazin-1-yl]-6-(2-hydroxy-ethylamino)-pyrimidine-5-carbonitrile, 2-caclopropylamino-4-(2-hydroxy-ethylamino)-6-(4-phenyl-piperazin-1-yl)-pyrimidine-5-carbonitrile, 2-{6-[4-(4-fluoro-phenyl)-piperazin-1-yl]-2-methyl-5-nitro-pyrimidin-4-yloxy}-ethanol, and 2,4-bis-cyclopropylamino-6-(4-phenyl-piperazin-1-yl)-pyrimidine-5-carbonitrile.

An additional preferred compound of formula Ib has the formula

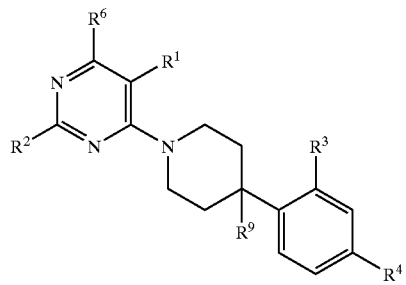

Ib2 wherein
$R^2$ is selected from the group consisting of $(C_1-C_7)$-alkyl and —$NHR^{10}$,
$R^{10}$ is selected from the group consisting of $(C_1-C_7)$-alkyl, —$(CH_2)_m$—$OR^{11}$, —$(CH_2)_p$—$(C_3-C_6)$-cycloalkyl and $R^{11}$ is selected from the group consisting of hydrogen and $(C_1-C_7)$-alkyl, —$(CH_2)_m$—NH—C(O)O—$(C_1-C_7)$-alkyl and —$(CH_2)_p$-pyridyl;

$R^3$ is selected from the group consisting of hydrogen and fluoro;

$R^6$ is selected from the group consisting of halogen, $(C_1-C_7)$-alkoxy, $(C_1-C_7)$-alkylthio, $-O-(CH_2)_m-OR^{11}$, $-O$-fluoro-$(C_1-C_7)$-alkyl and $-NHR^{12}$;

$R^9$ is hydrogen; and $R^{12}$ is selected from the group consisting of $(C_1-C_7)$-alkyl, $-(CH_2)_m-OR$ and $-(CH_2)_p-(C_3-C_6)$-cycloalkyl.

Exemplary preferred compounds of formula Ib2 are selected from the group consisting of 2-(cyclopropylmethyl-amino)-4-(2-hydroxy-ethylamino)-6-(4-phenyl-piperidin-1-yl)-pyrimidine-5-carbonitrile, 4-(4-phenyl-piperidin-1-yl)-2-[(pyridin-3-ylmethyl)-amino]-6-(2,2,2-trifluoro-ethoxy)-pyrimidine-5-carbonitrile, 4-[4-(4-fluoro-phenyl)-piperidin-1-yl]-2-[(pyridin-3-ylmethyl)-amino]-6-(2,2,2-trifluoro-ethoxy)-pyrimidine-5-carbonitrile, 2-caclopropylamino-4-(2-hydroxy-ethylamino)-6-(4-phenyl-piperidin-1-yl)-pyrimidine-5-carbonitrile, 4-[4-(4-fluoro-phenyl)-piperidin-1-yl]-2-(2-hydroxy-ethylamino)-6-(2,2,2-trifluoro-ethoxy)-pyrimidine-5-carbonitrile, 2-(cyclopropylmethyl-amino)-4-[4-(4-fluoro-phenyl)-piperidin-1-yl]-6-(2-hydroxy-ethylamino)-pyrimidine-5-carbonitrile, 4-(2-hydroxy-ethylamino)-6-(4-phenyl-piperidin-1-yl)-2-[(pyridin-3-ylmethyl)-amino]-pyrimidioine-5-carbonitrile, and 2-(2-hydroxy-ethylamino)-4-(4-phenyl-piperidin-1-yl)-6-(2,2,2-trifluoro-ethoxy)-pyrimidine-5-carbonitrile.

Another preferred compound of formula I in the scope of the present invention is a compound of formula

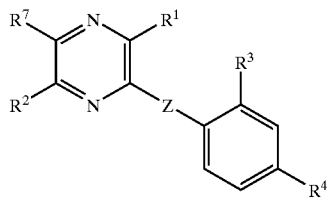

Ic or a pharmaceutically acceptable salt thereof

A preferred compound of formula Ic has the formula

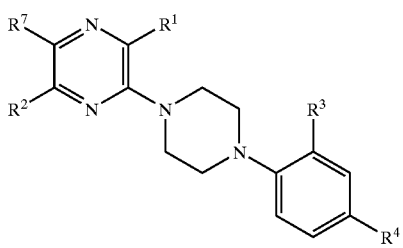

Ic1 wherein $R^2$ is selected from the group consisting of $(C_1-C_7)$-alkyl and $-NHR^{10}$, $R^{10}$ is selected from the group consisting of $(C_1-C_7)$-alkyl, $-(CH_2)_m-OR^{11}$, $-(CH_2)_p-(C_3-C_6)$-cycloalkyl and $R^{11}$ is selected from the group consisting of hydrogen and $(C_1-C_7)$-alkyl;

$R^3$ is selected from the group consisting of hydrogen and fluoro; and $R^7$ is selected from the group consisting of $(C_1-C_7)$-alkyl and phenyl.

A more preferred compound of formula Ic1 is, wherein $R^2$ is $(C_1-C_7)$-alkyl and $R^3$ is hydrogen. A more preferred compound exemplary of a formula Ic1 is selected from the group consisting of 4-(4-fluoro-phenyl)-6'-methyl-5'-phenyl-3,4,5,6-tetrahydro-2H-[1,2']bipyrazinyl-3'-carbonitrile, 5'-ethyl-4-(4-fluoro-phenyl)-6'-methyl-3,4,5,6-tetrahydro-2H-[1,2']bipyrazinyl-3'-carbonitrile, 6'-ethyl-4-(4-fluoro-phenyl)-5'-methyl-3,4,5,6-tetrahydro-2H-[1,2']bipyrazinyl-3'-carbonitrile, 5'-ethyl-6'-methyl-4-phenyl-3,4,5,6-tetrahydro-2H-[1,2']bipyrazinyl-3'-carbonitrile, and 6'-ethyl-5'-methyl-4-phenyl-3,4,5,6-tetrahydro-2H-[1,2']bipyrazinyl-3'-carbonitrile.

Another preferred compound of formula Ic has the formula

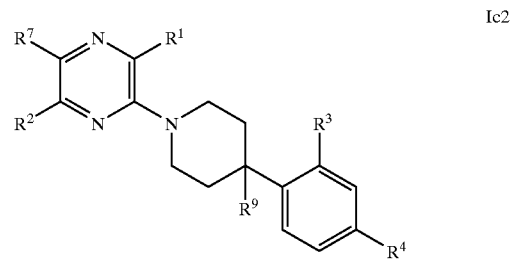

Ic2

A more preferred compound of formula Ic2 is wherein $R^2$ is $(C_1-C_7)$-alkyl and $R^3$ is hydrogen.

An exemplary more preferred compound of formula Ic2 is selected from the group consisting of 6-ethyl-5-methyl-3-(4-phenyl-piperidin-1-yl)-pyrazine-2-carbonitrile and 5-ethyl-6-methyl-3-(4-phenyl-piperidin-1-yl)-pyrazine-2-carbonitrile.

Another preferred compound of formula I has the formula

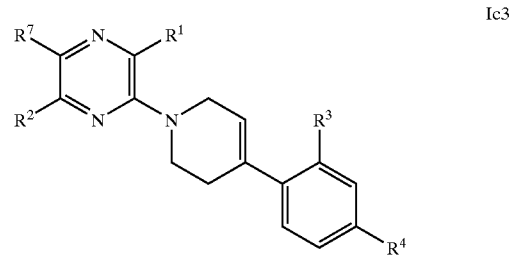

Ic3

A more preferred compound of formula Ic3 is wherein $R^2$ is selected from the group consisting of $(C_1-C_7)$-alkyl and $-NHR^{10}$, wherein $R^{10}$ is selected from the group consisting of $(C_1-C_7)$-alkyl, $-(CH_2)_m-OR^{11}$, $-(CH_2)_p-(C_3-C_6)$-cycloalkyl, and $R^{11}$ is selected from the group consisting of hydrogen and $(C_1-C_7)$-alkyl;

$R^3$ is selected from the group consisting of hydrogen and fluoro; and $R^7$ is selected from the group consisting of $(C_1-C_7)$-alkyl and phenyl.

A further preferred compound of formula Ic3 is seen when $R^2$ is $(C_1-C_7)$-alkyl and $R^3$ is hydrogen.

An exemplary further preferred compound of formula Ic3 is selected from the group consisting of 6-ethyl-5-methyl-3-(4-phenyl-3,6-dihydro-2H-pyridin-1-yl)-pyrazine-2-carbonitrile and 5-ethyl-6-methyl-3-(4-phenyl-3,6-dihydro-2H-pyridin-1-yl)-pyrazine-2-carbonitrile.

Yet another preferred compound of formula I in the scope of the invention has the formula

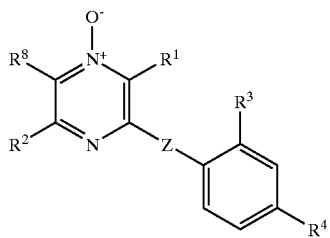

Id or a pharmaceutically acceptable salt thereof.

A more preferred compound of formula Id has the formula

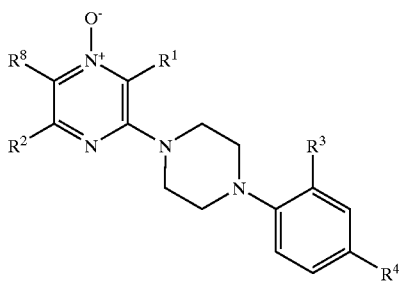

Id1 wherein $R^2$ is selected from the group consisting of $(C_1-C_7)$-alkyl and fluoro; and $R^8$ is $(C_1-C_7)$-alkyl.

Exemplary of a preferred compound of formula Id1 is a compound selected from the group consisting of 5'-ethyl-4-(4-fluoro-phenyl)-6'-methyl-4'-oxy-3,4,5,6-tetrahydro-2H-[1,2']bipyrazinyl-3'-carbonitrile, and 6'-ethyl-4-(4-fluoro-phenyl)-5'-methyl-4'-oxy-3,4,5,6-tetrahydro-2H-[1,2']bipyrazinyl-3'-carbonitrile.

Also preferred is another compound of formula I having the formula

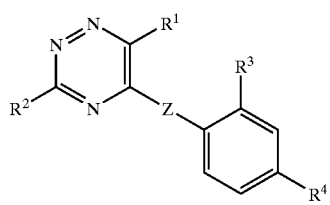

Ie or a pharmaceutically acceptable salt thereof.

A more preferred compound of formula 1e has the formula

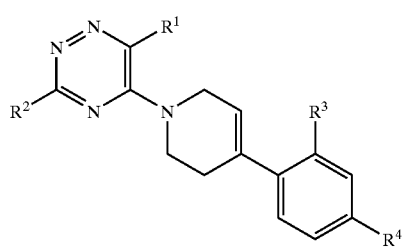

Ie1 wherein $R^2$ is —$NHR^{10}$, wherein $R^{10}$ is selected from the group consisting of $(C_1-C_7)$-alkyl, —$(CH_2)_m$—$OR^{11}$, —$(CH_2)_p$—$(C_3-C_6)$-cycloalkyl, and $R^{11}$ is selected from the group consisting of hydrogen and $(C_1-C_7)$-alkyl; and $R^3$ is hydrogen. An exemplary compound of formula Ie1 is 3-(2-hydroxy-ethylamino)-5-(4-phenyl-3,6-dihydro-2H-pyridin-1-yl)-[1,2,4]triazine-6-carbonitrile.

The term "$(C_1-C_7)$-alkyl" ("lower alkyl") used in the present description denotes straight-chain or branched saturated hydrocarbon residues with 1–7 carbon atoms, preferably with 1–4 carbon atoms, such as methyl, ethyl, n-propyl, i-propyl, butyl and the like.

The term "$(C_2-C_7)$-alkenyl" ("lower alkenyl") used in the present description denotes straight-chain or branched unsaturated hydrocarbon residues with 2–7 carbon atoms, preferably with 2–4 carbon atoms. A "$(C_2-C_7)$-alkenyl" group includes, for example, vinyl, prop-2-enyl, but-3-enyl, pent-4-enyl and isopropenyl.

The term "$(C_3-C_6)$-cycloalkyl" denotes a saturated carbocyclic group containing from 3 to 6 carbon atoms, such as cyclopropyl, cyclobutyl, cyclopentyl or cyclohexyl.

The term "halogen" embraces fluorine, chlorine, bromine and iodine.

A "fluoro-$(C_1-C_7)$-alkyl" group is a lower alkyl group as defined above, which is substituted by one or more fluorine atoms, for example trifluoromethyl, 2-fluoroethyl or 2,2,2-trifluoroethyl.

The terms "$(C_1-C_7)$-alkoxy" or "$(C_1-C_7)$-alkylthio" denote an lower alkyl group linked to an oxygen or sulphur atom, respectively, wherein the lower alkyl is defined as above. A $(C_1-C_7)$-alkoxy or a $(C_1-C_7)$-alkylthio group includes for example methoxy, ethoxy, methylthio or ethylthio.

The term "pharmaceutically acceptable salt" refers to any salt derived from a pharmaceutically acceptable inorganic or organic acid or base.

The compounds of formula I and their pharmaceutically acceptable salts can be manufactured by reacting a compound of formula

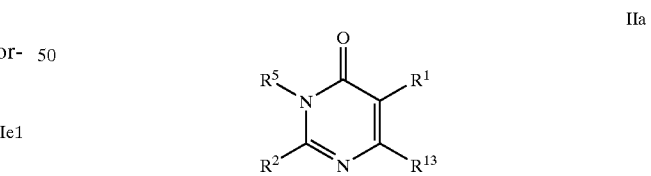

IIa wherein $R^{13}$ is halogen, with a compound of formula

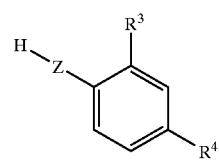

III forming a compound of formula

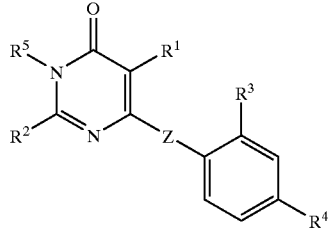
Ia wherein $R^1$ to $R^5$ and Z are as defined above,
and, if desired, converting a compound of formula Ia into a pharmaceutically acceptable salt; or
reacting a compound of formula

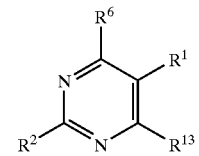
IIb wherein $R^6$ and $R^{13}$ are halogen, with a compound of formula

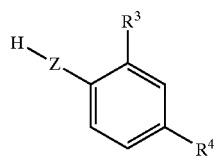
III and, if desired, substituting the halogen of $R^6$ with the respective nucleophiles forming a compound of formula

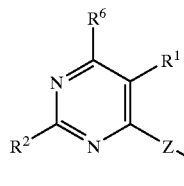
Ib wherein $R^1$ to $R^4$, $R^6$ and Z are as defined above,
and, if desired, converting a compound of formula Ib into a pharmaceutically acceptable salt; or
reacting a compound of formula

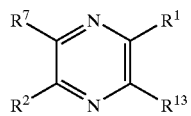
IIc wherein $R^{13}$ is halogen, with a compound of formula

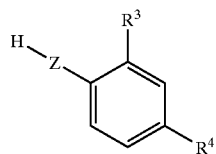
III forming a compound of formula

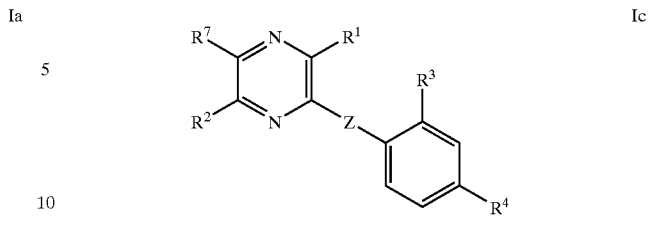
Ic wherein $R^1$ to $R^4$, $R^7$ and Z are as defined above, and, if desired, converting a compound of formula Ic into a pharmaceutically acceptable salt; or reacting a compound of formula

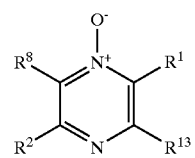
IId wherein $R^{13}$ is halogen, with a compound of formula

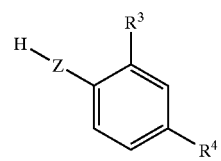
III forming a compound of formula

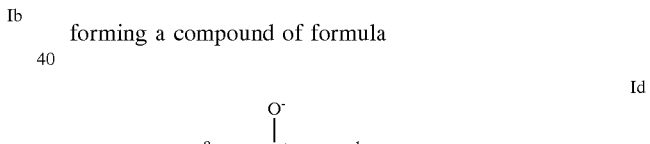
Id wherein $R^1$ to $R^4$, $R^8$ and Z are as defined above, and, if desired, converting a compound of formula Id into a pharmaceutically acceptable salt; or reacting a compound of formula

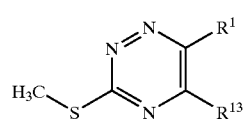
IIe wherein $R^{13}$ is halogen, with a compound of formula

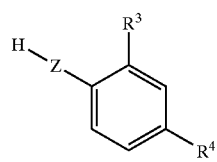

III and substituting the thiomethyl group with the respective nucleophiles to obtain a compound of formula

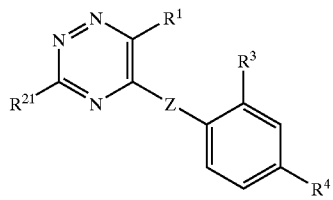

Ie-1 wherein $R^{21}$ is —$NHR^{10}$ and $R^1$, $R^3$, $R^4$ and Z are as defined above,
and, if desired, converting a compound of formula Ie-1 into a pharmaceutically acceptable salt; or reacting a compound of formula

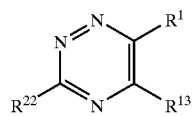

IIf wherein $R^{22}$ is $(C_1-C_7)$-alkyl and $R^{13}$ is halogen, with a compound of formula

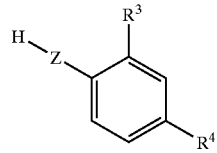

III forming a compound of formula

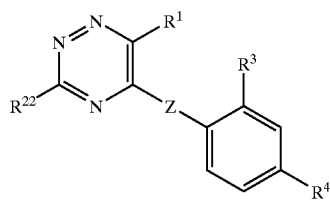

Ie-2 wherein $R^{22}$ is $(C_1-C_7)$-alkyl and $R^1$, $R^3$, $R^4$ and Z are as defined above, and, if desired, converting a compound of formula Ie into a pharmaceutically acceptable salt.

Compounds of formula Ia and Ib, wherein $R^2$ is $(C_1-C_7)$-alkyl, can be manufactured by reacting alkyl 6-bromo- or 6-chloro-5-nitro-3H-pyrimidin-4-ones of formula IIa-1, e.g. 6-bromo-2-methyl-5-nitro-3H-pyrimidin-4-one [Eur. Pat. Appl. EP 1 074 549 A2 (2001)], with optionally substituted phenyl-piperazines, phenyl-tetrahydropyridines or phenylpiperidines of formula III in the presence of a base like potassium carbonate, triethylamine or ethyldiisopropylamine in solvents like N,N-dimethylformamide, dimethylsulfoxide, acetone, methyl-ethylketone or tetrahydrofurane at temperatures between 0° C. and 100° C. to the pyrimidinones IV (Scheme 1). Alkylation of the pyrimidinones IV using optionally substituted alkyl halides, tosylates, mesylates or trifluoro-methansulfonates in solvents like ethanol, methanol, dichloromethane, chloroform, N,N-dimethylformamide, dimethylsulfoxide, acetone, methyl-ethylketone or tetrahydrofurane in the presence of base like alkali carbonates, e.g. sodium, potassium or cesium carbonate, tertiary amines like triethylamine or ethyldiisopropylamine, alkali metal hydrides, like sodium or potassium hydride, or phase transfer catalysts like benzyltrimethylammonium chloride in the presence of solid or concentrated aqueous sodium hydroxide gives variable mixtures of N- and/or O-alkylated compounds Ia-1 and Ib-1 wherein $R^{14}$ signifies $(C_1-C_7)$-alkyl, —$(CH_2)_m$—$OR^{11}$l, or fluoro-$(C_1-C_7)$-alkyl. The compounds Ia-1 and Ib-1 may contain functional groups in protected form in the N- or O-alkyl function which allow further structural modifications after removal of the protective functions.

Scheme 1

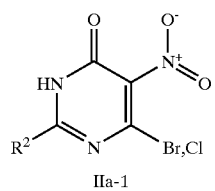
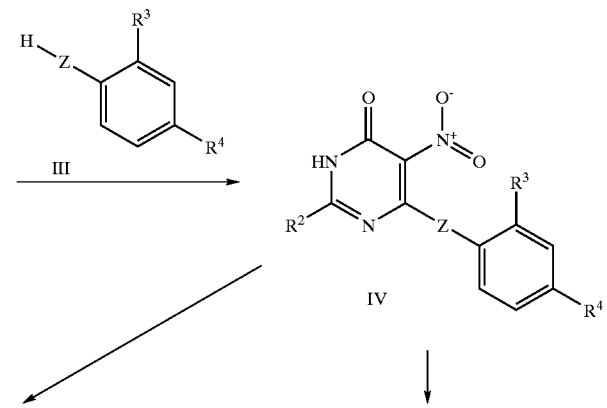

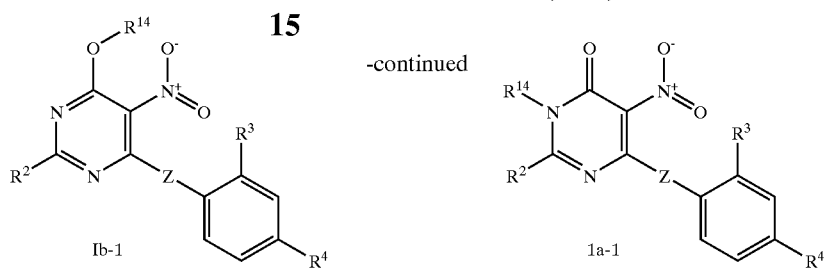

Known bis(methylthio)-acrylates V react with optionally substituted phenylpiperazines, phenyl-tetrahydropyridine or phenylpiperidines of formula III in the presence of bases like potassium carbonate and/or triethylamine in solvents like ethanol, methanol, acetone or methyl-ethylketone at temperatures between room temperature and 100° C. to adducts VI, which can be formed as the Z-isomer, as mixture of the E- and Z-isomers or as the E-isomer [Scheme 2 and Eur. Pat. Appl. EP 1 074 549 A2 (2001)]. The terms "E" and "Z" used in this context are "entgegen" and "zusammen": this useage is unrelated to the "Z" of formula I. Thereupon, adducts VI can be reacted with amidines or urea derivatives of formula VII or VIII either in the presence of 1,8-diazabicyclo[5.4.0]undec-7-ene in N,N-dimethylformamide or dimethylsulfoxide at temperatures between 70° C. and 140° C. or in the presence of sodium ethylate in ethanol preferentially at reflux thus yielding pyrimidinones Ia-2 or substituted pyrimidinones Ia-3. Pyrimidinones Ia-2 can then be alkylated as described for the sequence IV=>Ia-1 and Ib-1 in Scheme I.

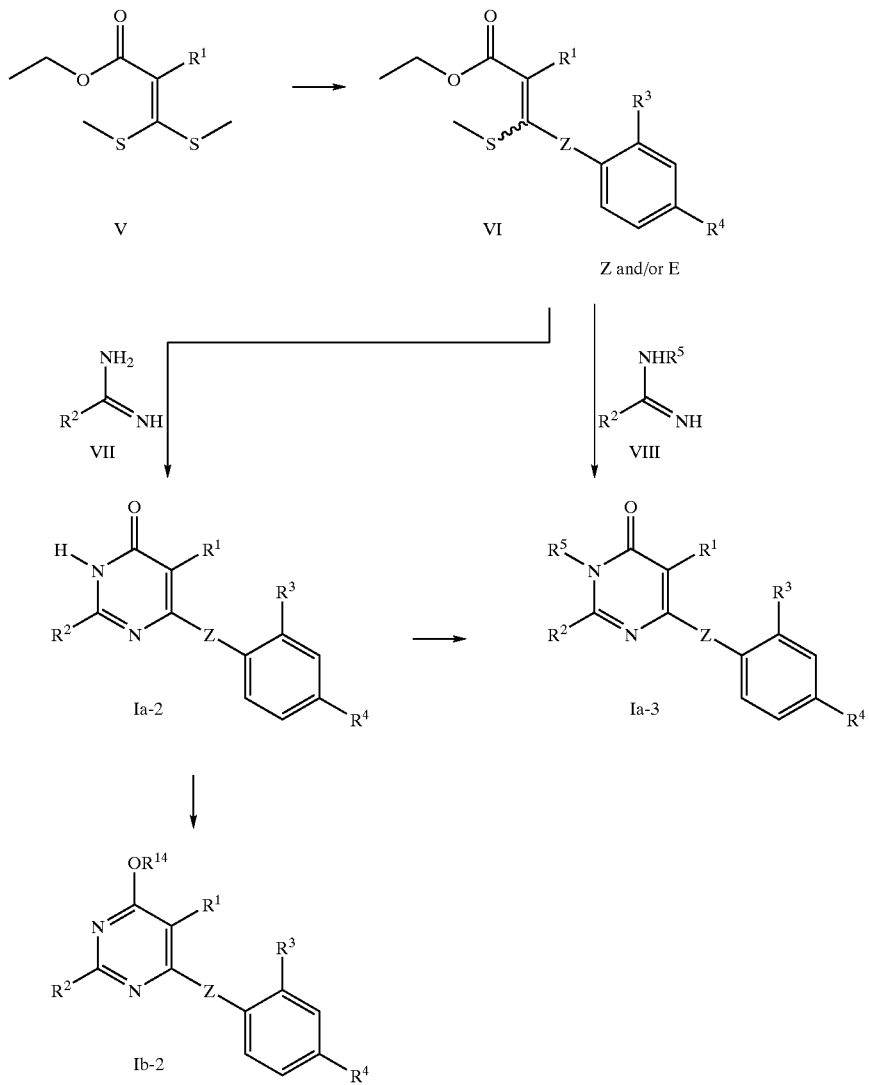

If an allyl moiety is introduced as $R^5$, then, it can also serve as protective function.

Thus, it allows modification at other parts of the molecules, e.g. in $R^2$ and a later removal of the N-allyl function by lithium borohydride in the presence of palladium(II)acetate and triphenylphosphin in an inert solvent like tetrahydrofuran or 1,2-dimethoxyethane at temperatures between room temperature and 60° C.

Compounds of formula Ib can be obtained by sequential substitution of compounds of formula IIb with the respective nucleophiles. The nucleophilic substitution reactions can be performed according to known methods, and for the sequence of introduction, the presence of further functionalities in the nucleophile has to be taken into account, a fact generally known to persons skilled in the art. For example, treatment of compounds of formula IIb-1 with compounds of formula III via compounds of formula IX are leading to compounds of formula Ib. Selective monosubstituion of di-chloro pyrimidines IIb-1 (Scheme 3) with optionally substituted secondary amines III can be performed in solvents like N,N-dimethylform-amide or dimethylsulfoxide in the presence of a base like triethylamine at temperatures between 0° C. and 60° C. producing mono-chloro pyrimidines IX. Thereafter, the remaining chloro atom in compounds IX can be replaced by i) alkoxy functions, treating compounds of formula IX with an alcoholate in the corresponding alcohol as solvent or in an inert solvent like tetrahydrofurane, N,N-dimethylformamide or dimethylsulfoxide at temperatures between room temperature and 100° C.; or by ii) amino functions, treating compounds of formula IX with an amine in an inert solvent like tetrahydrofurane, N,N-dimethylformamide or dimethylsulfoxide at temperatures between room temperature and 100° C.; or by iii) thio functions, treating compounds of formula IX with a thiol in the presence of a base like triethylamine or sodium hydride in an alcohol, N,N-dimethylform-amide or dimethylsulfoxide at temperatures between room temperature and 100° C. The replacement of the chloro group by a hydroxy function is preferentially performed in a two step procedure: a 4-methoxy-benzyloxy function is introduced first by reacting IX with the corresponding alcoholate as described above followed by treatment with methanolic hydrogen chloride at temperatures between 0° C. and 50° C. In case of hydroxy group containing intermediates, these can be protected according to known methods before the treatment with the alcoholates.

Scheme 3

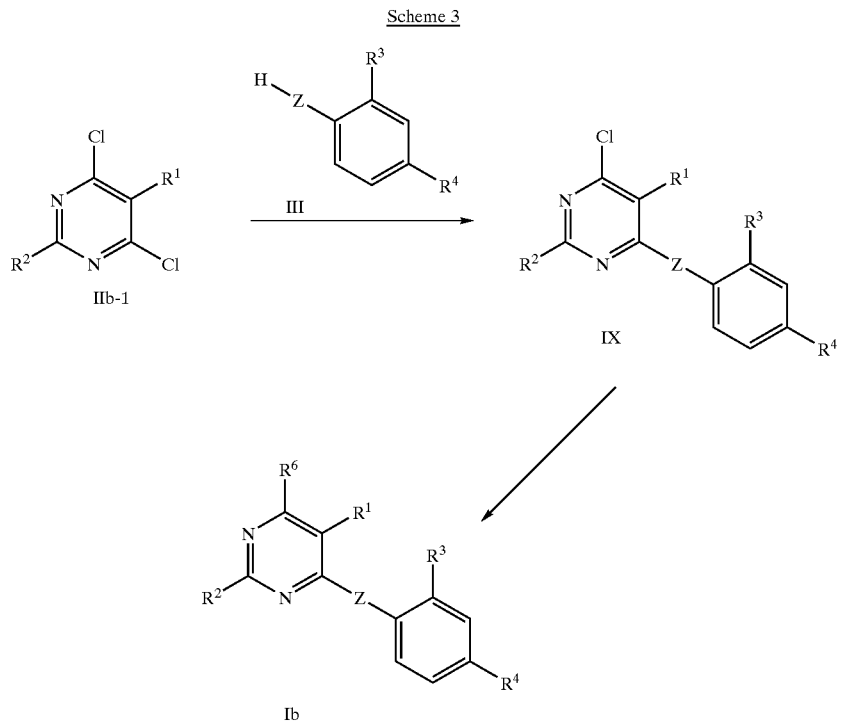

Compounds of formula IIb-1 wherein $R^2$ signifies $-NHR^{10}$ can be obtained starting from the 4,6-dichloro-2-methylsulfanyl-pyrimidine derivative X or the 2,4,6-trichloro-pyrimidine derivative XI. Starting with compounds of formula X, they are transformed into the 2-methylsulphonyl derivative according to known oxidative methods, e.g. by 3-chloro-perbenzoic acid in dichloromethane, followed by the treatment with the respective amines in tetrahydrofurane, dioxane, 1,2-dimethoxyethane, N,N-dimethylformamide or dimethylsulfoxide at temperatures between room temperature and about 100° C. to yield compounds of formula IIb-1.

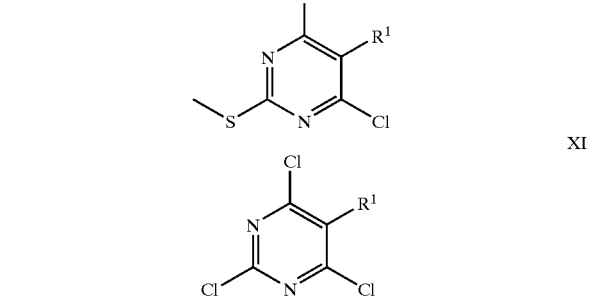

In case, compounds of formula XI are selected as starting materials, the treatment with amines in tetrahydrofurane, dioxane, 1,2-dimethoxyethane, ethanol, N,N-dimethylformamide or dimethylsulfoxide, at temperatures between room temperature and about 100° C., in presence of a base, e.g. potassium carbonate, triethylamine or ethyldiisopropyl-amine yields the 2- and 4-substituted derivatives. These can be separated by chromato-graphic methods and identified by physical methods known as such like $^{13}$C-NMR or X-ray analysis; e.g. when $R^2$ signifies hydroxyethylamino the assignment was performed by X-ray analysis. When an excess of the nucleophile is used under the aforementioned conditions, the 2,4-disubstituted derivative can be obtained.

To obtain compounds of formula Ic, 1,2-dicarbonyl compounds XII with $R^2$ and $R^7$ signifying both independently from each other hydrogen, phenyl, $(C_1–C_7)$-alkyl or $(C_2–C_7)$-alkenyl, react with 2-amino-malonic acid diamide XIII as described in *J. Amer. Chem. Soc.* 1949, 71, 78–81, either in the presence of an aqueous base at temperatures between 0° C. and 60° C. or in the absence of a base in solvents like water or an alcohol at temperatures between room temperature and 120° C. to form the 3-oxo-3,4-dihydro-pyrazine-2-carboxylic acid amides XIVa and XIVb, in which the former substituent $R^2$ of the 1,2-dicarbonyl compounds XII became the substituent $R^{7'}$ and the former substituent $R^7$ in the 1,2-dicarbonyl compounds XII became the substituent $R^{2'}$. Treatment of XIVa and XIVb either separately or as a mixture with phosphorus oxychloride and optionally additional phosphorus pentachloride in the presence of triethylamine or diethylaniline at temperatures between 40° C. and 120° C. give 3-chloro-pyrazine-2-carbonitriles XVa and XVb (Scheme 4).

3-chloro-pyrazine-2-carbonitriles XVa and XVb react either separately or as a mixture with optionally substituted phenyl-piperazines, phenyl-tetrahydropyridines or phenyl-piperidines or their hydrochlorides in solvents like N,N-dimethylformamide, acetonitrile, acetone or dimethylsulfoxide in the presence of a base like potassium carbonate or a tertiary amine as diisopropyl-ethylamine at temperatures between room temperature and 80° C. to form the desired 3-(phenyl-piperazine-yl, phenyl-tetrahydro-pyridine-yl or phenylpiperidine-yl)-pyrazine-2-carbonitriles Ic-1 and Ic-2 which can be separated by known methods such as chromatography or crystallization.

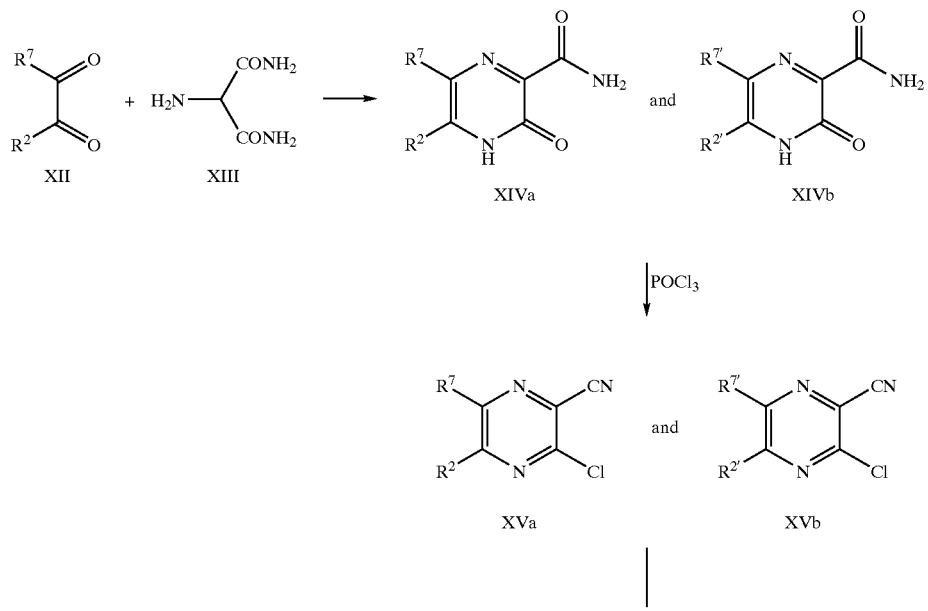

Scheme 4

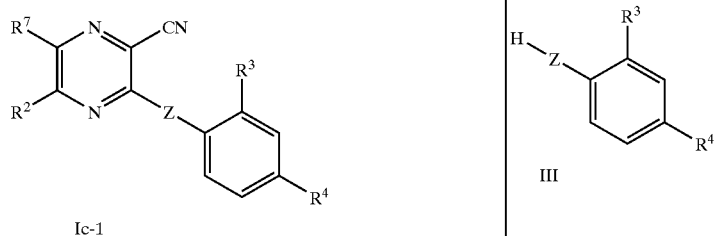

Ic-1 and

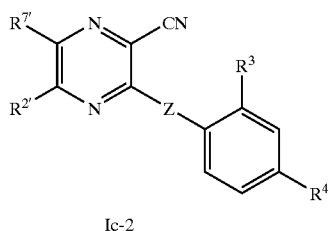

Ic-2

To obtain compounds of formula Id, 3-chloro-pyrazine-2-carbonitriles XVc and XVd can be oxidized to the corresponding mono-oxy-pyrazine compounds by various methods. If hydrogen peroxide in a solvent like trifluoroacetic acid is used preferentially at temperatures between 0° C. and 60° C., then mainly 1-oxy-pyrazine-2-carbonitriles IId-1 and IId-2 are formed (Scheme 5). 1-Oxy-pyrazine-2-carbonitriles IId-1 and IId-2 react either separately or as a mixture with optionally substituted phenyl-piperazines, phenyl-tetrahydropyridines or phenylpiperidines or their hydrochlorides in solvents like N,N-dimethylformamide, acetonitrile, acetone or dimethylsulfoxide in the presence of a base like potassium carbonate or a tertiary amine as diisopropyl-ethylamine at temperatures between room temperature and 80° C. to form the desired 3-(phenyl-piperazine-yl, phenyl-tetrahydropyridine-yl or phenylpiperidine-yl) 1-oxy-pyrazine-2-carbonitriles Id-1 and Id-2 which can be separated by known methods such as chromatography or crystallization.

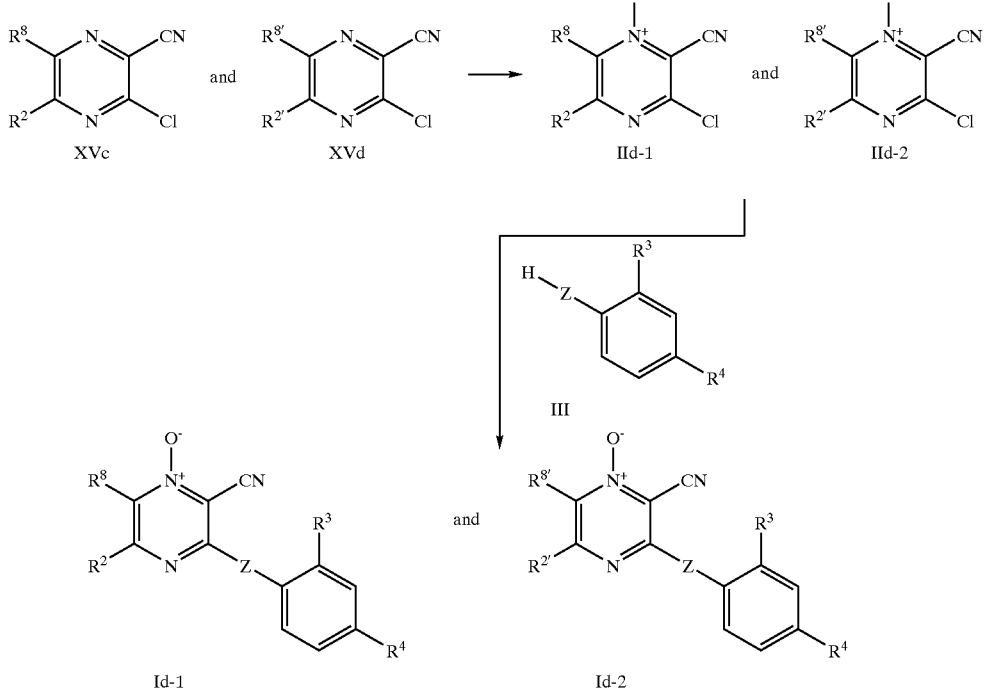

The diazotization of the 3-amino-5-chloro-2-cyano-pyrazine XVI according to *J.Org.Chem.* 1975, 40, 2341–2347, with t-butyl-nitrite in solvents like acetonitrile or N,N-dimethylformamide in the presence of copper-(II)-bromide at temperatures between room temperature and 95° C. gives the 3-bromo-5-chloro-2-cyano-pyrazine IIg. The 3-bromo-5-chloro-2-cyano-pyrazine IIg reacts with one equivalent of a primary or secondary amine to two products, in which either the chloro-atom or the bromo-atom is replaced in the amine moiety. If the reaction is performed with a primary amine $R^{10}NH_2$ in a solvent like dioxane or tetrahydrofurane in the presence of a base like triethylamine or diisopropylethylamine, preferentially at room temperature, then the pyrazine IIh with replaced chloro-atom can be obtained with reasonable selectivity. In a second analogous reaction, optionally substituted phenyl-piperazines, phenyl-tetrahydro-pyridines or phenylpiperidines or their hydrochlorides can then be reacted with the pyrazine IIh in solvents like N,N-dimethylformamide, tetrahydrofurane, dioxane, acetonitrile, acetone or dimethylsulfoxide and in the presence of a base like potassium carbonate or a tertiary amine like diisopropyl-ethylamine at temperatures between room temperature and 80° C. giving compounds of formula Ic-3 wherein $R^7$ signifies hydrogen (Scheme 6).

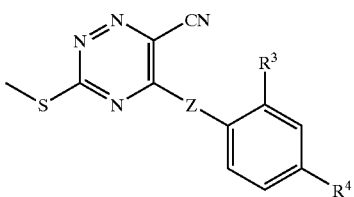

with appropriate nucleophiles. Substitution of the Me-S-group in compound Ie-3 by optionally substituted N-nucleophiles can be performed in water, ethanol, N,N-dimethylformamide, dimethylsulfoxide, 1,2-dimethoxyethane, preferentially in dioxane at elevated temperatures, preferentially 100° C. to 160° C.

Compounds of formula Ie-3 are prepared by reaction of 1,3-(methylthio)-5-chloro-6-cyano-1,2,4-triazine (J. J. Huang, *J. Org. Chem.* 1985, 50, 2293–2298) with amines of formula III

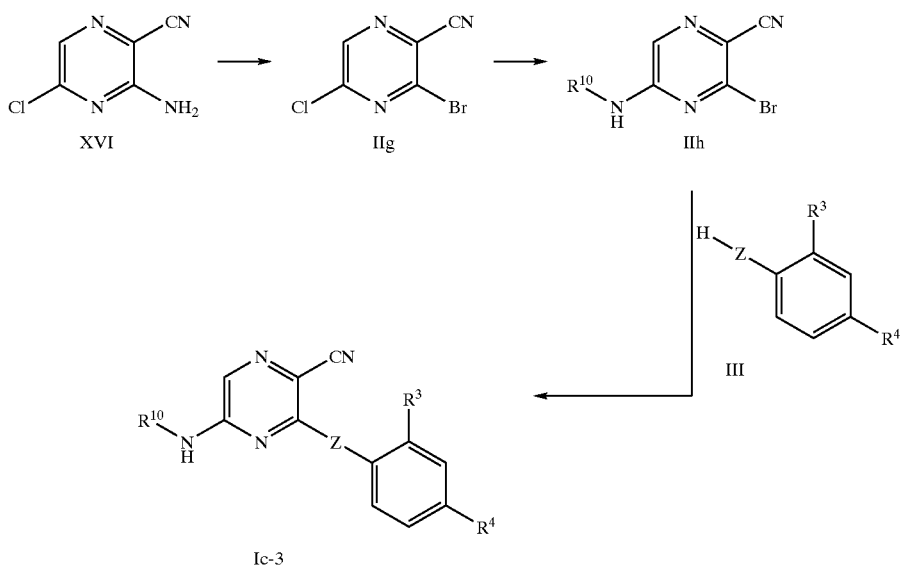

Compounds of formula Ie-1a

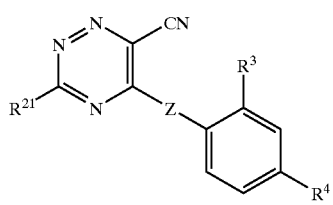

wherein $R^{21}$ signifies —$NHR^{10}$, can be obtained by reacting compounds of formula Ie-3.

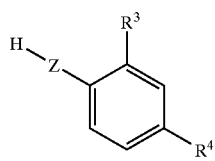

in the presence of a base like triethylamine or ethyl-diisopropylamine in solvents like N,N-dimethylformamide, dimethylsulfoxide, methyl-ethylketone, ethanol, dioxane or tetrahydrofuran at temperatures between 10° C. and 50° C.

The functionalization of the N-nucleophiles can also serve as a protective function. Thus, modifications at the other part of the $R^{21}$-substituent are allowed, e.g. removal of a N-protecting group, like the tert-butoxycarbonyl group, by methods well documented in the literature.

Compounds of formula Ie-2a

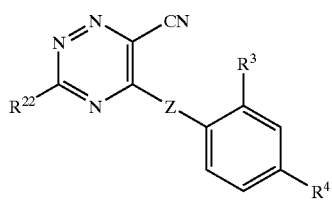

wherein $R^{22}$ signifies $(C_1$–$C_7)$-alkyl can be prepared by reacting the intermediate IIf-1 with amines of formula III in the presence of a base like triethylamine or ethyldiisopropylamine in solvents like N,N-dimethylformamide, dimethylsulfoxide, methyl-ethylketone, ethanol, dioxane or tetrahydrofurane at temperatures between 10° C. and 50° C.

The intermediate If-1 can be synthesized in analogy to the procedure described in J. Org. Chem. 1972, 37 (24), 3958–3960, starting with the condensation of the corresponding amidrazones XVII and methyl or ethyl oxomalonate XVIII, followed by ammonolysis of the ester XIX, and, finally, dehydration of the amide XX and substitution of the hydroxy group by chlorine (Scheme 7).

Scheme 7

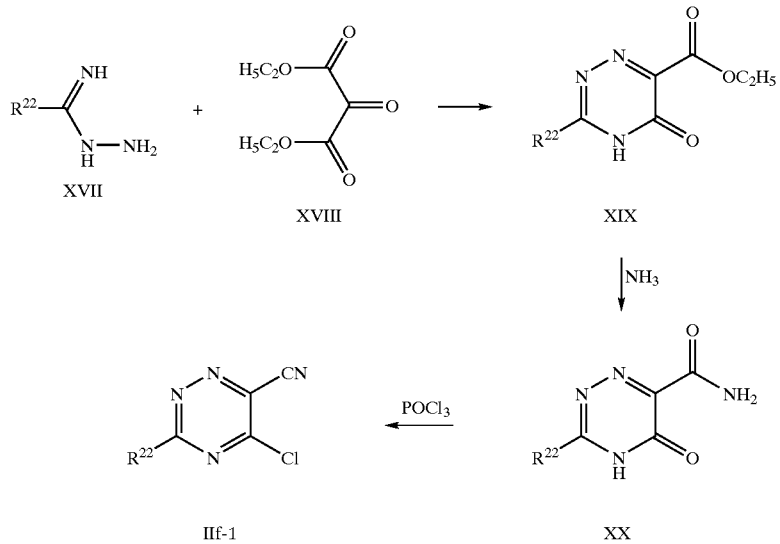

The pharmaceutically acceptable salts can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds of formula I.

The compounds of formula I and their pharmaceutically acceptable salts are, as already mentioned above, metabotropic glutamate receptor antagonists and can be used for the treatment or prevention of acute and/or chronic neurological disorders, such as epilepsy, stroke, chronic and acute pain, psychosis, schizophrenia, Alzheimer's disease, cognitive disorders, memory deficits and psychosis. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The compounds of the present invention are group I mGluR antagonists. Their pharmacological activity was tested using the following method:

Binding Assay for the Characterization of mGluR 1 Antagonistic Properties

Binding assay with tritiated 1-ethyl-2-methyl-6-oxo-4-(1,1,2-tritritio-1,2,4,5-tetrahydro-benzo[d]azepin-3-yl)-1,6-dihydro-pyrimidine-5-carbonitrile: HEK 293 cells were transiently transfected with the rat mGluR[1] a receptor. The cells were collected and washed 3 times with PBS. The cell pellets were frozen at −80° C. Membranes were prepared from HEK 293 cells transfected with the rat mGluR[1] a receptor and used in the binding experiments at 10 μg proteins per assay after resuspension in a HEPES NaOH 20 mM, pH=7.4 binding buffer. 1-Ethyl-2-methyl-6-oxo-4-(1,1,2-tritritio-1,2,4,5-tetrahydro-benzo [d]azepin-3-yl)-1,6-dihydro-pyrimidine-5-carbonitrile (S.A 33.4 Ci/mmol) was used at 3 nM final concentration. The incubation with variable concentrations of potential inhibitors was performed for 1 hour at room temperature, the incubate was then filtered onto GF/B glass fiber filter preincubated 1 hour in PEI 0,1% and washed 3 times with 1 ml of cold binding buffer. The radioactivity retained on the unifilter 96 was counted using a Topcount β counter. After correction for non specific binding the data were normalized and the $IC_{50}$ value calculated using a 4 parameters logistic equation which was fitted to the inhibition curve.

The preferred compounds have an $IC_{50}$ range of 0.001–10.0 µmol/l.

In table I below are shown some specific $IC_{50}$ values of preferred compounds of formula I of the present invention as measured with the binding assay described above:

TABLE I

| Compound name | Example No. | $IC_{50}$ (µmol/l)) |
|---|---|---|
| 6-[4-(4-fluoro-phenyl)-piperazin-1-yl]-2-methyl-5-nitro-3H-pyrimidin-4-one | 1 | 0.81 |
| 2-methyl-5-nitro-6-(4-phenyl-piperidin-1-yl)-3H-pyrimidin-4-one | 5 | 0.063 |
| 6-[4-(4-fluoro-phenyl)-piperazin-1-yl]-3-(2-hydroxy-ethyl)-2-methyl-5-nitro-3H-pyrimidin-4-one | 8-1 | 0.042 |
| 2-{6-[4-(4-fluoro-phenyl)-piperazin-1-yl]-2-methyl-5-nitro-pyrimidin-4-yloxy}-ethanol | 8-2 | 0.058 |
| 3-ethyl-6-[4-(4-fluoro-phenyl)-piperazin-1-yl]-2-methyl-5-nitro-3H-pyrimidin-4-one | 10-1 | 0.049 |
| 4-ethoxy-6-[4-(4-fluoro-phenyl)-piperazin-1-yl]-2-methyl-5-nitro-pyrimidine | 10-2 | 0.18 |
| 6-[4-(4-fluoro-phenyl)-piperidin-1-yl]-3-(4-hydroxy-butyl)-2-methyl-5-nitro-3H-pyrimidin-4-one | 18 | 0.28 |
| 4-[4-(2-fluoro-phenyl)-piperazin-1-yl]-2,6-bis-(2-hydroxy-ethylamino)-pyrimidine-5-carbonitrile | 20 | 0.290 |
| 2,4-bis-(2-hydroxy-ethylamino)-6-[4-(2-methyl-sulfanyl-phenyl)-piperazin-1-yl]-pyrimidine-5-carbonitrile | 25 | 0.350 |
| 2,4-bis-(2-hydroxy-ethylamino)-6-[4-(2-nitro-phenyl)-piperazin-1-yl]-pyrimidine-5-carbonitrile | 29 | 0.75 |
| 4-[4-(4-fluoro-phenyl)-piperidin-1-yl]-2,6-bis-(2-hydroxy-ethylamino)-pyrimidine-5-carbonitrile | 32 | 0.700 |
| 4-[4-(4-fluoro-phenyl)-3,6-dihydro-2H-pyridin-1-yl]-2,6-bis-(2-hydroxy-ethylamino)-pyrimidine-5-carbonitrile | 35 | 0.390 |
| 4-(4-cyano-4-phenyl-piperidin-1-yl)-2,6-bis-(2-hydroxy-ethylamino)-pyrimidine-5-carbonitrile | 37 | 1.8 |
| 2,4-bis-cyclopropylamino-6-(4-phenyl-piperazin-1-yl)-pyrimidine-5-carbonitrile | 38 | 0.064 |
| 4-(4-phenyl-piperazin-1-yl)-2,6-bis-[(pyridin-2-ylmethyl)-amino]-pyrimidine-5-carbonitrile | 40 | 1.50 |
| 2-cyclopropylamino-4-(2-hydroxy-ethylamino)-6-(4-phenyl-piperazin-1-yl)-pyrimidine-5-carbonitrile | 47 | 0.033 |
| 4-(2-hydroxy-ethylamino)-6-(4-phenyl-piperazin-1-yl)-2-[(pyridin-3-ylmethyl)-amino]-pyrimidine-5-carbonitrile | 49 | 0.15 |
| 4-(2-hydroxy-ethylamino)-6-(4-phenyl-piperidin-1-yl)-2-[(pyridin-3-ylmethyl)-amino]-pyrimidine-5-carbonitrile | 54 | 0.030 |
| 2-(2-hydroxy-ethylamino)-4-(4-phenyl-piperidin-1-yl)-6-(2,2,2-trifluoro-ethoxy)-pyrimidine-5-carbonitrile | 60 | 0.036 |
| 4-chloro-2-(cyclopropylmethyl-amino)-6-(4-phenyl-piperazin-1-yl)-pyrimidine-5-carbonitrile | 63 | 0.025 |
| 4-chloro-6-[4-(4-fluoro-phenyl)-piperidin-1-yl]-2-(2-hydroxy-ethylamino)-pyrimidine-5-carbonitrile | 68 | 0.140 |
| 2-amino-4-[4-(4-fluoro-phenyl)-piperazin-1-yl]-6-methylsulfanyl-pyrimidine-5-carbonitrile | 70 | 0.210 |
| 2-amino-4-[4-(4-fluoro-phenyl)-piperidin-1-yl]-6-methylsulfanyl-pyrimidine-5-carbonitrile | 73 | 0.159 |
| 5'-ethyl-6'-methyl-4-phenyl-3,4,5,6-tetrahydro-2H-[1,2']bipyrazinyl-3'-carbonitrile | 75-1 | 0.017 |
| 6'-ethyl-5'-methyl-4-phenyl-3,4,5,6-tetrahydro-2H-[1,2']bipyrazinyl-3'-carbonitrile | 75-2 | 0.023 |
| 5'-ethyl-4-(4-fluoro-phenyl)-6'-methyl-4'-oxy-3,4,5,6-tetrahydro-2H-[1,2']bipyrazinyl-3'-carbonitrile | 79-1 | 0.025 |
| 6'-ethyl-4-(4-fluoro-phenyl)-5'-methyl-4'-oxy-3,4,5,6-tetrahydro-2H-[1,2']bipyrazinyl-3'-carbonitrile | 79-2 | 0.21 |
| 4-(4-fluoro-phenyl)-6'-(2-hydroxy-ethylamino)-3,4,5,6-tetrahydro-2H-[1,2']bipyrazinyl-3'-carbonitrile | 83 | 1.0 |

TABLE I-continued

| Compound name | Example No. | $IC_{50}$ (µmol/l)) |
|---|---|---|
| 3-(2-hydroxy-ethylamino)-5-(4-phenyl-3,6-dihydro-2H-pyridin-1-yl)-[1,2,4]triazine-6-carbonitrile | 84 | 0.66 |

The compounds of formula I and pharmaceutically acceptable salts thereof can be used as pharmaceutical compositions, e.g. in the form of pharmaceutical preparations. The pharmaceutical compositions can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, draées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary.

Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, pharmaceutical compositions containing a compound of formula I or a pharmaceutically acceptable salt thereof and a therapeutically inert excipient are also an object of the present invention, as is a process for the production of such pharmaceutical compositions which comprises bringing a therapeutically effective amount of one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

Finally, as mentioned earlier, compounds of formula I and of pharmaceutically acceptable salts are useful thereof for the production of pharmaceutical compositons. These pharmaceutical compositions are useful in a method of treatment for the control or prevention of acute and/or chronic neurological disorders which comprises administering a therapeutically effective amount of the pharmaceutical composi-

29 tion containing the compound of formula 1 or a pharmaceutically acceptable salt there eo to a person having a disease responsive to mediation of the mGluR1 receptor The following examples are provided for illustration of the invention. They should not be considered as limiting the scope of the invention, but merely as being representative thereof. Unless stated to the contrary, all of the examples listed below were prepared and characterized as described.

EXAMPLE 1

6-[4-(4-Fluoro-phenyl)-piperazin-1-yl]-2-methyl-5-nitro-3H-pyrimidin-4-one 0.791 g (6.0 mmol) of N-ethyldiisopropylamine were slowly added to a solution of 0.468 g (2.00 mmol) of the 6-bromo-2-methyl-5-nitro-3H-pyrimidin-4-one (as prepared according to Eur. Pat. Appl. EP 1 074 549 A2) and 0.441 g (2.40 mmol) of the 1-(4-fluoro-phenyl)piperazine in 20 ml of N,N-dimethylformamide. The reaction mixture was stirred at room temperature for 16 hours. It was then poured into 50 ml of an ice/water mixture and extracted 3 times with 50 ml of dichloromethane. The combined dichloromethane phases were dried over magnesium sulfate and evaporated under reduced pressure. The residue obtained was then recrystallised from an ethylacetate/hexane mixture. There was thus obtained 0.570 g (1.71 mmol, 85.5 of theory) of the 6-[4-(4-fluoro-phenyl)-piperazin-1-yl]-2-methyl-5-nitro-3H-pyrimidin-4-one as yellow solid; m.p.>250° C. (decomposition); MS: $[M+H]^+=334$.

EXAMPLE 2

6-[4-(2-Fluoro-phenyl)-piperazin-1-yl]-2-methyl-5-nitro-3H-pyrimidin-4-one

In analogy to the procedure described in example 1, the 6-bromo-2-methyl-5-nitro-3H-pyrimidin-4-one (as prepared in Eur. Pat. Appl. EP 1 074 549 A2) was treated with the (2-fluoro-phenyl)-piperazine in N,N-dimethylformamide in the presence of potassium carbonate at room temperature to yield the 6-[4-(2-fluoro-phenyl)-piperazin-1-yl]-2-methyl-5-nitro-3H-pyrimidin-4-one as yellow amorphous solid; MS: $[M+H]^+=334$.

EXAMPLE 3

6-(4-Hydroxy-4-phenyl-piperidin-1-yl)-2-methyl-5-nitro-3H-pyrimidin-4-one

In analogy to the procedure described in example 1, the 6-bromo-2-methyl-5-nitro-3H-pyrimidin-4-one (as prepared in Eur. Pat. Appl. EP 1 074 549 A2) was treated with the 4-hydroxy-4-phenylpiperidine in N,N-dimethylformamide in the presence of potassium carbonate at room temperature to yield the 6-(4-hydroxy-4-phenyl-piperidin-1-yl)-2-methyl-5-nitro-3H-pyrimidin-4-one as yellow solid; m.p.>250° C. (decomposition); MS: $[M+H]^+=331$.

EXAMPLE 4

2-Methyl-5-nitro-6-(4-phenyl-piperazin-1-yl)-3H-pyrimidin-4-one

In analogy to the procedure described in example 1, the 6-bromo-2-methyl-5-nitro-3H-pyrimidin-4-one (as prepared in Eur. Pat. Appl. EP 1 074 549 A2) was treated with the 1-phenylpiperazine in N,N-dimethylformamide in the presence of potassium carbonate at room temperature to yield the 2-methyl-5-nitro-6-(4-phenyl-piperazin-1-yl)-3H-pyrimidin-4-one as yellow solid; m.p.>250° C. (decomposition); MS: $[M-H]^-=314$.

30

EXAMPLE 5

2-Methyl-5-nitro-6-(4-phenyl-piperidin-1-yl)-3H-pyrimidin-4-one

In analogy to the procedure described in example 1, the 6-bromo-2-methyl-5-nitro-3H-pyrimidin-4-one (as prepared in Eur. Pat. Appl. EP 1074549 A2) was treated with the 4-phenylpiperidine in N,N-dimethylformamide in the presence of N-ethyldiisopropyl-amine at room temperature to yield the 2-methyl-5-nitro-6-(4-phenyl-piperidin-1-yl)-3H-pyrimidin-4-one as yellowish solid; m.p. 210–213° C.; MS: $[M+H]^+=315$.

EXAMPLE 6

2-Methyl-5-nitro-6-(4-phenyl-3,6-dihydro-2H-pyridin-1-yl)-3H-pyrimidin-4-one

In analogy to the procedure described in example 1, the 6-bromo-2-methyl-5-nitro-3H-pyrimidin-4-one (prepared as in Eur. Pat. Appl. EP 1 074 549 A2) was treated with the 1,2,3,6-tetrahydro-4-phenylpiperidine hydrochloride in N,N-dimethylformamide in the presence of N-ethyldiisopropylamine at room temperature to yield the 2-methyl-5-nitro-6-(4-phenyl-3,6-dihydro-2H-pyridin-1-yl)-3H-pyrimidin-4-one as yellowish solid; m.p. 212–216° C. (decomposition); MS: $[M+H]^+=313$.

EXAMPLE 7

6-[4-(4-Fluoro-phenyl)-piperidin-1-yl]-2-methyl-5-nitro-3H-pyrimidin-4-one

In analogy to the procedure described in example 1, the 6-bromo-2-methyl-5-nitro-3H-pyrimidin-4-one (as prepared in Eur. Pat. Appl. EP 1 074 549 A2) was treated with the 4-(4-fluoro-phenyl)-piperidine hydrochloride in N,N-dimethylformamide in the presence of N-ethyldiisopropylamine at room temperature to yield the 6-[4-(4-fluoro-phenyl)-piperidin-1-yl]-2-methyl-5-nitro-3H-pyrimidin-4-one as yellowish solid;

m.p. 218–221° C. (decomposition); MS: $[M-H]^-=331$.

EXAMPLE 8

6-[4-(4-Fluoro-phenyl)-piperazin-1-yl]-3-(2-hydroxy-ethyl)-2-methyl-5-nitro-3H-pyrimidin-4-one and 2-{6-[4-(4-fluoro-phenyl)-piperazin-1-yl]-2-methyl-5-nitro-pyrimidin-4-yloxy}-ethanol 0.180 g (0.540 mmol) of the 6-[4-(4-fluoro-phenyl)-piperazin-1-yl]-2-methyl-5-nitro-3H-pyrimidin-4-one (example 1) and 0.142 g (1.1 mmol) of N-ethyldiisopropylamine, dissolved in 5.0 ml of N,N-dimethylformamide, were slowly added between –5° C. and 0° C. to a suspension of 0.923 g (7.0 mmol) of 2-bromo-ethanol and 0.897 g (6.5 mmol) of potassium carbonate in 5.0 ml of N,N-dimethylformamide. The reaction mixture was then stirred at room temperature for 48 hours. It was then poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with a 9:1 to 1:1 v/v gradient of hexane and ethylacetate as the eluent giving 0.039 g (0.10 mmol, 19.1% of theory) of the 2-{6-[4-(4-fluoro-phenyl)-piperazin-1-yl]-2-methyl-5-nitro-pyrimidin-4-yloxy}-ethanol as a light yellow amorphous solid; MS: $[M+H]^+=378$; and 0.091 g (0.241 mmol, 44.7% of theory) of the 6-[4-(4-fluoro-phenyl)-piperazin-1-yl]-3-(2-hydroxy-ethyl)-2-methyl-5-nitro-3H-pyrimidin-4-one as yellowish amorphous solid; MS: $[M+H]^+378$.

EXAMPLE 9

2-Methyl-5-nitro-6-(4-phenyl-piperidin-1-yl)-3-(2,2, 2-trifluoro-ethyl)-3H-pyrimidin-4-one and 2-methyl-5-nitro-4-(4-phenyl-piperidin-1-yl)-6-(2,2,2-trifluoro-ethoxy)-pyrimidine 0.591 g (2.55 mmol) of 2,2,2-trifluoroethyl trifluoromethanesulfonate were added slowly at room temperature to a suspension of 0.200 g (0.636 mmol) of the 2-methyl-5-nitro-6-(4-phenyl-piperidin-1-yl)-3H-pyrimidin-4-one (example 5) and 0.135 g (1.27 mmol) of sodium carbonate in 5.0 ml of acetone. After stirring of the reaction mixture for 2 hours, 0.136 g (0.99 mmol) of potassium carbonate were added and stirring continued for 18 hours. Additional 0.296 g (1.27 mmol) of 2,2,2-trifluoroethyl trifluoromethanesulfonate were added and stirring continued for 4 hours. The reaction mixture was then poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with a 9:1 to 1:1 v/v gradient of hexane and ethylacetate as the eluent giving 0.077 g (0.194 mmol, 30.5% of theory) of the 2-methyl-5-nitro-4-(4-phenyl-piperidin-1-yl)-6-(2,2, 2-trifluoro-ethoxy)-pyrimidine as a light yellow solid; m.p. 114–117° C.; MS: [M+H]$^+$=397; and 0.166 g (0.419 mmol, 65.8% of theory) of the 2-methyl-5-nitro-6-(4-phenyl-piperidin-1-yl)-3-(2,2,2-trifluoro-ethyl)-3H-pyrimidin-4-one as yellowish solid;

m.p. 161–163° C.; MS: [M+H]$^+$=397.

EXAMPLE 10

3-Ethyl-6-[4-(4-fluoro-phenyl)-piperazin-1-yl]-2-methyl-5-nitro-3H-pyrimidin-4-one and 4-ethoxy-6-[4-(4-fluoro-phenyl)-piperazin-1-yl]-2-methyl-5-nitro-pyrimidine In analogy to the procedure described in example 8, the 6-[4-(4-fluoro-phenyl)-piperazin-1-yl]-2-methyl-5-nitro-3H-pyrimidin-4-one (example 1) was treated with ethyliodide and potassium carbonate in N,N-dimethylformamide at room temperature to yield the 4-ethoxy-6-[4-(4-fluoro-phenyl)-piperazin-1-yl]-2-methyl-5-nitro-pyrimidine as a light yellow solid; m.p. 116–119° C.; MS: [M+H]$^+$=362; and the 3-ethyl-6-[4-(4-fluoro-phenyl)-piperazin-1-yl]-2-methyl-5-nitro-3H-pyrimidin-4-one as yellowish solid; m.p. 126–128° C.; MS: [M+H]$^+$=362.

EXAMPLE 11

4-[4-(4-Fluoro-phenyl)-piperazin-1-yl]-6-isopropoxy-2-methyl-5-nitro-pyrimidine

In analogy to the procedure described in example 8, the 6-[4-(4-fluoro-phenyl)-piperazin-1-yl]-2-methyl-5-nitro-3H-pyrimidin-4-one (example 1) was treated with 2-bromopropane, potassium iodide and potassium carbonate in N,N-dimethylformamide at 80° C. to yield the 4-[4-(4-fluoro-phenyl)-piperazin-1-yl]-6-isopropoxy-2-methyl-5-nitro-pyrimidine as a light yellow solid; m.p. 98–100° C.; MS: [M+H]$^+$=376.

EXAMPLE 12

6-[4-(4-Fluoro-phenyl)-piperazin-1-yl]-2-methyl-5-nitro-3-(2,2,2-trifluoro-ethyl)-3H-pyrimidin-4-one and 4-[4(4-fluoro-phenyl)-piperazin-1-yl]-2-methyl-5-nitro-6-(2,2,2-trifluoro-ethoxy)-pyrimidine In analogy to the procedure described in example 9, the 6-[4-(4-fluoro-phenyl)-piperazin-1-yl]-2-methyl-5-nitro-3H-pyrimidin-4-one (example 1) was treated with 2,2,2-trifluoroethyl trifluoromethanesulfonate, sodium and potassium carbonate in acetone at room temperature to yield the 4-[4-(4-fluoro-phenyl)-piperazin-1-yl]-2-methyl-5-nitro-6-(2,2,2-trifluoro-ethoxy)-pyrimidine as a light brown solid; m.p. 92–95° C.; MS: [M+H]$^+$=416; and the 6-[4-(4-fluoro-phenyl)-piperazin-1-yl]-2-methyl-5-nitro-3-(2,2,2-trifluoro-ethyl)-3H-pyrimidin-4-one as yellow amorphous solid;

MS: [M+H]$^+$=416.

EXAMPLE 13

6-[4-(4-Fluoro-phenyl)-piperidin-1-yl]-2-methyl-5-nitro-3-(2,2,2-trifluoro-ethyl)-3H-pyrimidin-4-one and 4-4[-(4-fluoro-phenyl)-piperidin-1-yl]-2-methyl-5-nitro-6-(2,2,2-trifluoro-ethoxy)-pyrimidine In analogy to the procedure described in example 9, the 6-[4-(4-fluoro-phenyl)-piperidin-1-yl]-2-methyl-5-nitro-3H-pyrimidin-4-one (example 7) was treated with 2,2,2-trifluoro-ethyl trifluoromethanesulfonate, sodium and potassium carbonate in acetone at room temperature to yield the 4-[4-(4-fluoro-phenyl)-piperidin-1-yl]-2-methyl-5-nitro-6-(2,2,2-trifluoro-ethoxy)-pyrimidine as a yellow oil; MS: [M+H]$^+$=415; and the 6-[4-(4-fluoro-phenyl)-piperidin-1-yl]-2-methyl-5-nitro-3-(2,2,2-trifluoro-ethyl)-3H-pyrimidin-4-one as yellow solid; m.p. 61–64° C.; MS: [M+H]$^+$=415.

EXAMPLE 14

6-[4-(4-Fluoro-phenyl)-piperidin-1-yl]-3-(2-methoxy-ethyl)-2-methyl-5-nitro-3H-pyrimidin-4-one and 4-[4-(4-fluoro-phenyl)-piperidin-1-yl]-6-(2-methoxy-ethoxy)-2-methyl-5-nitro-pyrimidine In analogy to the procedure described in example 8, the 6-[4-(4-fluoro-phenyl)-piperidin-1-yl]-2-methyl-5-nitro-3H-pyrimidin-4-one (example 7) was treated with 2-bromoethyl methyl ether and potassium carbonate in N,N-dimethylformamide at 50° C. to yield the 4-[4-(4-fluoro-phenyl)-piperidin-1-yl]-6-(2-methoxy-ethoxy)-2-methyl-5-nitro-pyrimidine as a yellow oil; MS: [M+H]$^{30}$=391; and the 6-[4-(4-fluoro-phenyl)-piperidin-1-yl]-3-(2-methoxy-ethyl)-2-methyl-5-nitro-3H-pyrimidin-4-one as a yellow solid; m.p. 45–48° C.; MS: [M+H]$^+$=391.

EXAMPLE 15

6-{6-[4-(4-Fluoro-phenyl)-piperazin-1-yl]-2-methyl-5-nitro-pyrimidin-4-yloxy}-hexan-1-ol In analogy to the procedure described in example 8, the 6-[4-(4-fluoro-phenyl)-piperazin-1-yl]-2-methyl-5-nitro-3H-pyrimidin-4-one (example 1) was treated with 6-chloro-1-hexanol and potassium carbonate in N,N-dimethylformamide at 120° C. to yield the 6-{6-[4-(4-fluoro-phenyl)-piperazin-1-yl]-2-methyl-5-nitro-pyrimidin-4-yloxy}-hexan-1-ol as a yellow amorphous solid; MS: [M+H]$^+$=434.

EXAMPLE 16

{4-[4-(4-Fluoro-phenyl)-piperidin-1-yl]-2-methyl-5-nitro-6-oxo-6H-pyrimidin-1-yl}-acetonitrile In analogy to the procedure described in example 8, the 6-[4-(4-fluoro-phenyl)-piperidin-1-yl]-2-methyl-5-nitro-3H-pyrimidin-4-one (example 7) was treated with bromoacetonitrile and potassium carbonate in N,N-dimethylformamide at room temperature to yield the {4-[4-(4-fluoro-phenyl)-piperidin-1-yl]-2-methyl-5-nitro-6-oxo- 6H-pyrimidin-1-yl}-acetonitrile as a yellow solid; m.p. 213–215° C. (decomposition); MS: [M+H]$^+$=372.

EXAMPLE 17

4-{6-[4-(4-Fluoro-phenyl)-piperidin-1-yl]-2-methyl-5-nitro-pyrimidin-4-yloxy}-butan-1-ol a) 3-[4-(tert-Butyl-dimethyl-silanyloxy)-butyl]-6-[4-(4-fluoro-phenyl)-piperidin-1-yl]-2-methyl-5-nitro-3H-pyrimidin-4-one and 4-[4-(tert-butyl-dimethyl-silanyloxy)-butoxy-6-[4-(4-fluoro-phenyl)-piperidin-1-yl]-2-methyl-5-nitro-pyrimidine In analogy to the procedure described in example 8, the 6-[4-(4-fluoro-phenyl)-piperidin-1-yl]-2-methyl-5-nitro-3H-pyrimidin-4-one (example 7) was treated with tert.-butyl-(4-chlorobutoxy)dimethylsilane and potassium carbonate in N,N-dimethyl-formamide at 80° C. to yield the 4-[4-(tert-butyl-dimethyl-silanyloxy)-butoxy]-6-[4-(4-fluoro-phenyl)-piperidin-1-yl]-2-methyl-5-nitro-pyrimidine as a yellowish oil; MS: [M+H]$^+$=519; and the 3-[4-(tert-butyl-dimethyl-silanyloxy)-butyl]-6-[4-(4-fluoro-phenyl)-piperidin-1-yl]-2-methyl-5-nitro-3H-pyrimidin-4 one as a yellowish oil; MS: [M+H]$^+$=519.

b) 4-{6-[4-(4-Fluoro-phenyl)-piperidin-1-yl]-2-methyl-5-nitro-pyrimidin-4-yloxy}-butan-1-ol 0.590 g (14.5 mmol) of hydrofluoric acid (47–51% in water) were slowly added to a solution of 0.375 g (0.723 mmol) of the 4-[4-(tert-butyl-dimethyl-silanyloxy)-butoxy]-6-[4-(4-fluoro-phenyl)-piperidin-1-yl]-2-methyl-5-nitro-pyrimidine in 10.0 ml of acetonitrile and 5.0 ml of dichloromethane. The reaction mixture was then stirred at room temperature for 1 hour. It was then poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with a 9:1 to 1:1 v/v gradient of hexane and ethylacetate as the eluent giving 0.181 g (0.448 mmol, 61.9% of theory) of the 4-{6-[4-(4-fluoro-phenyl)-piperidin-1-yl]-2-methyl-5-nitro-pyrimidin-4-yloxy}-butan-1-ol as a light yellowish oil; MS: [M+H]$^+$=405.

EXAMPLE 18

6-[4-(4-Fluoro-phenyl)-piperidin-1-yl]-3-(4-hydroxy-butyl)-2-methyl-5-nitro-3H-pyrimidin-4-one In analogy the procedure described in example 17b, the 3-[4-(tert-butyl-dimethyl-silanyloxy)-butyl]-6-[4-(4-fluoro-phenyl)-piperidin-1-yl]-2-methyl-5-nitro-3H pyrimidin-4-one (example 17a) was treated with hydrofluoric acid (47–51% in water) in acetonitrile and dichloromethane at room temperature to yield the 6-[4-(4-fluoro-phenyl)-piperidin-1-yl]-3-(4-hydroxy-butyl)-2-methyl-5-nitro-3H-pyrimidin-4-one as a yellow solid; m.p. 154–156° C.; MS: [M+H]$^+$=405

EXAMPLE 19

3-(2-Ethoxy-ethyl)-6-[4-(4-fluoro-phenyl)-piperazin-1-yl]-2-methyl-5-nitro-3H-pyrimidin-4-one and 4-(2-ethoxy-ethoxy)-6-[4-(4-fluoro-phenyl)-piperazin-1-yl]-2-methyl-5-nitro-pyrimidine In analogy to the procedure described in example 8, the 6-[4-(4-fluoro-phenyl)-piperidin-1-yl]-2-methyl-5-nitro-3H-pyrimidin-4-one (example 7) was treated with 2-bromoethyl ethyl ether and potassium carbonate in N,N-dimethylformamide at 80° C. to yield the 4-(2-ethoxy-ethoxy)-6-[4-(4-fluoro-phenyl)-piperazin-1-yl]-2-methyl-5-nitro-pyrimidine as a yellow oil; MS: [M+H]$^+$=406; and the 3-(2-ethoxy-ethyl)-6-[4-(4-fluoro-phenyl)-piperazin-1-yl]-2-methyl-5-nitro-3H-pyrimidin-4-one as a yellow oil; MS: [M+H]$^+$=406.

EXAMPLE 20

4-[4-(2-Fluoro-phenyl)-piperazin-1-yl]-2,6-bis-(2-hydroxy-ethylamino)-pyrimidine-5-carbonitrile a) 4-chloro-2,6-bis-(2-hydroxy-ethylamino)-pyrimidine-5-carbonitrile A solution of 10.0 g (48 mmol) of 2,4,6-trichloro-5-cyano-pyrimidine in 150 ml of dioxane was treated at 0° C. with 16.4 ml (96 mmol) of N-ethyl-diisopropylamine, followed by 8.7 ml (144 mmol) of ethanolamine. While warming up to room temperature, yellowish solid material started to precipitate. The yellow solution was stirred overnight, then the resulting material was separated by filtration and the mother liquor evaporated to dryness. The residue was stirred with dichloromethane and the solid filtered. To eliminate the ethanolammonium chloride, the two combined solid fractions were treated with 100 ml of ethanol, thereupon the resulting product was washed with 150 ml of dichloromethane. After drying under reduced pressure, 10.45 g (40.6 mmol, 84.5 of theory) of 4-chloro-2,6-bis-(2-hydroxy-ethylamino)-pyrimidine-5-carbonitrile were obtained as a yellowish powder.

b) 4-[4-(2-Fluoro-phenyl)-piperazin-1-yl]-2,6-bis-(2-hydroxy-ethylamino)-pyrimidine-5-carbonitrile A mixture of 125 mg (0.48 mmol) of 4-chloro-2,6-bis-(2-hydroxy-ethylamino)-pyrimidine-5-carbonitrile and 63 mg (0.48 mmol) of N-ethyl-diisopropylamine in 5 ml of ethanol was treated with 97 mg (0.48 mmol) of 1-(2-fluorophenyl)-piperazine.

The solution was heated at 80° C. during 15 h, and, thereafter, evaporated under reduced pressure. To separate the unreacted starting material, the residue obtained was then chromatographed on silica gel using a 95:15:0.1 mixture of dichloromethane, methanol and ammonium hydroxide as the eluent giving 70 mg (0.17 mmol, 36% of theory) of the 4-[4-(2-fluoro-phenyl)-piperazin-1-yl]-2,6-bis-(2-hydroxy-ethylamino)-pyrimidine-5-carbonitrile as an amorphous, white solid;
MS: [M+H]$^+$=402.

EXAMPLE 21

4-[4-(4-Fluoro-phenyl)-piperazin-1-yl]-2,6-bis-(2-hydroxy-ethylamino)-pyrimidine-5-carbonitrile In analogy to the procedure described in example 20b, 4-chloro-2,6-bis-(2-hydroxy-ethylamino)-pyrimidine-5-carbonitrile was treated with the 1-(4-fluorophenyl)-piperazine in dioxane in the presence of N-ethyl-diisopropylamine at 60° C. to yield 4-[4-(4-fluoro-phenyl)-piperazin-1-yl]-2,6-bis-(2-hydroxy-ethylamino)-pyrimidine-5-carbonitrile as a white lyophilisate; MS: [M+H]$^+$=402.

EXAMPLE 22

4-[4-(2-cyano-phenyl)-piperazin-1-yl]-2,6-bis-(2-hydroxy-ethylamino)-pyrimidine-5-carbonitrile In analogy to the procedure described in example 20b, 4-chloro-2,6-bis-(2-hydroxy-ethylamino)-pyrimidine-5-carbonitrile was treated with 1-(2-cyanophenyl)-piperazine in dioxane in the presence of N-ethyl-diisopropylamine at 50° C. to yield 4-[4-(2-cyano-phenyl)-piperazin-1-yl]-2,6-bis-(2-hydroxy-ethylamino)-pyrimidine-5-carbonitrile as an amorphous, light brown solid; MS: [M]$^+$=408.

EXAMPLE 23

2,4-Bis-(2-hydroxy-ethylamino)-6-(4-o-tolyl-piperazin-1-yl)-pyrimidine-5-carbonitrile In analogy to the procedure described in example 20b, 4-chloro-2,6-bis-(2-hydroxy-ethylamino)-pyrimidine-5-carbonitrile was treated with 1-(o-tolyl)-piperazine dihydrochloride in dioxane in the presence of N-ethyl-diisopropylamine at 80° C. to yield 2,4-bis-(2-hydroxy-ethylamino)-6-(4-o-tolyl-piperazin-1-yl)-pyrimidine-5-carbonitrile as an amorphous, light brown solid; MS: [M+H]$^+$=398.

EXAMPLE 24

4-[4-(2-Ethyl-phenyl)-piperazin-1-yl]-2,6-bis-(2-hydroxy-ethylamino)-pyrimidine-5-carbonitrile In analogy to the procedure described in example 20b, 4-chloro-2,6-bis-(2-hydroxy-ethylamino)-pyrimidine-5-carbonitrile was treated with 1-(2-ethyl-phenyl)-piperazine in dioxane in the presence of N-ethyl-diisopropylamine at 60° C. to yield 4-[4-(2-ethyl-phenyl)-piperazin-1-yl]-2,6-bis-(2-hydroxy-ethylamino)-pyrimidine-5-carbonitrile as an amorphous, light brown solid; MS: [M+H]$^+$=412.

EXAMPLE 25

2,4-Bis-(2-hydroxy-ethylamino)-6-[4-(2-methylsulfanyl-phenyl)-piperazin-1-yl]-pyrimidine-5-carbonitrile In analogy to the procedure described in example 20b, 4-chloro-2,6-bis-(2-hydroxy-ethylamino)-pyrimidine-5-carbonitrile was treated with 1-(2-methylsulfanyl-phenyl)-piperazine in dioxane in the presence of N-ethyl-diisopropylamine at 60° C. to yield the 2,4-bis-(2-hydroxy-ethylamino)-6-[4-(2-methylsulfanyl-phenyl)-piperazin-1-yl]-pyrimidine-5-carbonitrile as a yellowish lyophilisate; MS: [M+H]$^+$=430.

EXAMPLE 26

2,4-Bis-(2-hydroxy-ethylamino)-6-[4-(2-methoxy-phenyl)-piperazin-1-yl]-pyrimidine-5-carbonitrile In analogy to the procedure described in example 20b, 4-chloro-2,6-bis-(2-hydroxy-ethylamino)-pyrimidine-5-carbonitrile was treated with 1-(2-methoxy-phenyl)-piperazine in dioxane in the presence of N-ethyl-diisopropylamine at 60° C. to yield the 2,4-bis-(2-hydroxy-ethylamino)-6-[4-(2-methoxy-phenyl)-piperazin-1-yl]-pyrimidine-5-carbonitrile as a yellowish lyophilisate; MS: [M+H]$^+$=414.

EXAMPLE 27

4-[4-(2-Ethoxy-phenyl)-piperazin-1-yl]-2,6-bis-(2-hydroxy-ethylamino)-pyrimidine-5-carbonitrile In analogy to the procedure described in example 20b, 4-chloro-2,6-bis-(2-hydroxy-ethylamino)-pyrimidine-5-carbonitrile was treated with 1-(2-ethoxy-phenyl)-piperazine in dioxane in the presence of N-ethyl-diisopropylamine at 60° C. to yield 4-[4-(2-ethoxy-phenyl)-piperazin-1-yl]-2,6-bis-(2-hydroxy-ethylamino)-pyrimidine-5-carbonitrile as a white lyophilisate; MS: [M+H]$^+$=428.

EXAMPLE 28

2,4-Bis-(2-hydroxy-ethylamino)-6-[4-(2-hydroxy-phenyl)-piperazin-1-yl]-pyrimidine-5-carbonitrile In analogy to the procedure described in example 20b, 4-chloro-2,6-bis-(2-hydroxy-ethylamino)-pyrimidine-5-carbonitrile was treated with 1-(2-hydroxy-phenyl)-piperazine in dioxane in the presence of N-ethyl-diisopropylamine at 60° C. to yield 2,4-bis-(2-hydroxy-ethylamino)-6-[4-(2-hydroxy-phenyl)-piperazin-1-yl]-pyrimidine-5-carbonitrile as a white lyophilisate; MS: [M+H]$^+$=399.

EXAMPLE 29

2,4-Bis-(2-hydroxy-ethylamino)-6-[4-(2-nitro-phenyl)-piperazin-1-yl]-pyrimidine-5-carbonitrile In analogy to the procedure described in example 20b, 4-chloro-2,6-bis-(2-hydroxy-ethylamino)-pyrimidine-5-carbonitrile was treated with 1-(2-nitro-phenyl)-piperazine in dioxane in the presence of N-ethyl-diisopropylamine at 60° C. to yield 2,4-bis-(2-hydroxy-ethylamino)-6-[4-(2-nitro-phenyl)-piperazin-1-yl]-pyrimidine-5-carbonitrile as a yellowish lyophilisate; MS: [M+H]$^+$=429.

EXAMPLE 30

2,4-Bis-(2-hydroxy-ethylamino)-6-(4-phenyl-piperazin-1-yl)-pyrimidine-5-carbonitrile In analogy to the procedure described in example 20b, 4-chloro-2,6-bis-(2-hydroxy-ethylamino)-pyrimidine-5-carbonitrile was treated with 4-phenyl-piperazine in N,N-dimethylformamide in the presence of N-ethyl-diisopropylamine at 40° C. to yield 2,4-bis-(2-hydroxy-ethylamino)-6-(4-phenyl-piperazin-1-yl)-pyrimidine-5-carbonitrile as an amorphous, colorless solid; MS: [M+H]$^+$=384.

EXAMPLE 31

2,4-Bis-(2-hydroxy-ethylamino)-6-(4-phenyl-piperidin-1-yl)-pyrimidine-5-carbonitrile In analogy to the procedure described in example 20b, 4-chloro-2,6-bis-(2-hydroxy-ethylamino)-pyrimidine-5-carbonitrile was treated with 4-phenyl-piperidine in ethanol in the presence of N-ethyl-diisopropylamine at 80° C. to yield 2,4-bis-(2-hydroxy-ethylamino)-6-(4-phenyl-piperidin-1-yl)-pyrimidine-5-carbonitrile as an amorphous, white solid; MS: [M+H]$^+$383.

EXAMPLE 32

4-[4-(4-Fluoro-phenyl)-piperidin-1-yl]-2,6-bis-(2-hydroxy-ethylamino)-pyrimidine-5-carbonitrile In analogy to the procedure described in example 20b, 4-chloro-2,6-bis-(2-hydroxy-ethylamino)-pyrimidine-5-carbonitrile was treated with 4-(4-fluorophenyl)-piperidine hydrochloride in dioxane in the presence of N-ethyl-diisopropylamine at 90° C. to yield 4-[4-(4-fluoro-phenyl)-piperidin-1-yl]-2,6-bis-(2-hydroxy-ethylamino)-pyrimidine-5-carbonitrile as an amorphous, white solid; MS: [M+H]$^+$=401.

EXAMPLE 33

2,4-Bis-(2-hydroxy-ethylamino)-6-[4-(2-methoxy-phenyl)-piperidin-1-yl]-pyrimidine-5-carbonitrile In analogy to the procedure described in example 20b, 4-chloro-2,6-bis-(2-hydroxy-ethylamino)-pyrimidine-5-carbonitrile was treated with 4-(2-methoxy-phenyl)-piperidine in dioxane in the presence of N-ethyl-diisopropylamine at 90° C. to yield 2,4-bis-(2-hydroxy-ethylamino)-6-[4-(2-methoxy-phenyl)-piperidin-1-yl]-pyrimidine-5-carbonitrile as a white lyophilisate; MS: [M+H]$^+$=413.

EXAMPLE 34

2,4-Bis-(2-hydroxy-ethylamino)-6-(4-phenyl-3,6-dihydro-2H-pyridin-1-yl)-pyrimidine-5-carbonitrile In analogy to the procedure described in example 20b, 4-chloro-2,6-bis-(2-hydroxy-ethylamino)-pyrimidine-5-carbonitrile was treated with 4-phenyl-1,2,3,6-tetrahydro-pyridine hydrochloride in ethanol in the presence of N-ethyl-diisopropylamine at 80° C. to yield 2,4-bis-(2-hydroxy-ethylamino)-6-(4-phenyl-3,6-dihydro-2H-pyridin-1-yl)-pyrimidine-5-carbonitrile as an amorphous, brown solid; MS: $[M+H]^+=381$.

EXAMPLE 35

4-[4-(4-Fluoro-phenyl)-3,6-dihydro-2H-pyridin-1-yl]-2,6-bis-(2-hydroxy-ethylamino)-pyrimidine-5-carbonitrile In analogy to the procedure described in example 20b, 4-chloro-2,6-bis-(2-hydroxy-ethylamino)-pyrimidine-5-carbonitrile was treated with 4-(4-fluoro-phenyl)-1,2,3,6-tetrahydro-pyridine hydrochloride in dioxane in the presence of N-ethyl-diisopropyl-amine at 90° C. to yield 4-[4-(4-fluoro-phenyl)-3,6-dihydro-2H-pyridin-1-yl]-2,6-bis-(2-hydroxy-ethylamino)-pyrimidine-5-carbonitrile as an amorphous, white solid;
MS: $[M+H]^+=399$.

EXAMPLE 36

4-[4-(4-Fluoro-phenyl)-3,6-dihydro-2H-pyridin-1-yl]-2,6-bis-(2-hydroxy-ethylamino)-pyrimidine-5-carbonitrile In analogy to the procedure described in example 20 (2), the 4-chloro-2,6-bis-(2-hydroxy-ethylamino)-pyrimidine-5-carbonitrile was treated with the 4-(4-fluorophenyl)-1,2,3,6-tetrahydro-pyridine hydrochloride in dioxane in the presence of N-ethyl-diisopropylamine at 60° C. to yield the 4-[4-(4-fluoro-phenyl)-3,6-dihydro-2H-pyridin-1-yl]-2,6-bis-(2-hydroxy-ethylamino)-pyrimidine-5-carbonitrile as an amorphous, white solid; MS: $[M+H]^+=399$.

EXAMPLE 37

4-(4-cyano-4-phenyl-piperidin-1-yl)-2,6-bis-(2-hydroxy-ethylamino)-pyrimidine-5-carbonitrile In analogy to the procedure described in example 20b, 4-chloro-2,6-bis-(2-hydroxy-ethylamino)-pyrimidine-5-carbonitrile was treated with 4-phenyl-piperidine-4-carbonitrile in dioxane in the presence of N-ethyl-diisopropylamine at 60° C. to yield 4-(4-cyano-4-phenyl-piperidin-1-yl)-2,6-bis-(2-hydroxy-ethylamino)-pyrimidine-5-carbonitrile as an amorphous, white solid; MS: $[M+H]^+=408$.

EXAMPLE 38

2,4-Bis-cyclopropylamino-6-(4-phenyl-piperazin-1-yl)-pyrimidine-5-carbonitrile a) 2,4,6-Trichloro-5-cyano-pyrimidine The starting material,2,4,6-trichloro-5-cyano-pyrimidine, was prepared in analogy to the procedure described for 4,6-dichloro-2-methylsulfanyl-pyrimidine-5-carbonitrile [J. Heterocycl. Chem. (1971), 8(5),445–453] as follows:
(i) 2,4,6-Trichloro-pyrimidine-5-carbaldehyde To 179.2 ml (1.96 mol) of phosphoryl chloride were added 23.1 ml (0.30 mol) of N,N-dimethylformamide at 0° C. within 20 min. Thereupon, portionwise, 38.6 g (0.30 mol) of barbituric acid were added to the white suspension within 30 min. The reaction mixture was warmed up to room temperature and then heated to 100° C. during 15 h. For the working-up, the brownish solution was evaporated under reduced pressure and the resulting residue hydrolyzed on 700 ml of ice-water. The aqueous phase was extracted altogether with 3500 ml of tert-butyl-methyl ether, then the combined organic phases were dried over sodium sulfate, and evaporated under reduced pressure. The resulting residue was stirred with ether to yield 28.4 g (0.13 mol, 44.5% of theory) of 2,4,6-trichloro-pyrimidine-5-carbaldehyde as a yellow powder. Additional 2.9 g (0.013 mol, 4.6% of theory) of the product were obtained by concentrating the etheric solution. The quality of the product was sufficient to be used in the next step without further purification.

(ii) (E/Z)-2,4,6-Trichloro-pyrimidine-5-carbaldehyde oxime

A solution of 8.76 g (0.041 mol) of 2,4,6-trichloro-pyrimidine-5-carbaldehyde in 109.4 ml of acetic acid and 5.5 ml of water was treated at room temperature with 2.88 g (0.041 mol) of hydroxylamine hydrochloride. Thereafter, the mixture was warmed to 60° C. during 25 min. For the working-up, the red solution was cooled to room temperature and poured into 300 ml of a mixture of ice and water. The aqueous phase was extracted three times with 250 ml of dichloromethane. The combined organic phases were washed two times with a saturated aqueous solution of sodium chloride, then dried over sodium sulfate, and evaporated under reduced pressure to yield 8.03 g (0.035 mol, 85% of theory) of (E/Z)-2,4,6-trichloro-pyrimidine-5-carbaldehyde oxime as an orange solid which was used in the next step without further purification.

(iii) 2,4,6-Trichloro-5-cyano-pyrimidine

A solution of 8.03 g (0.035 mol) of (E/Z)-2,4,6-trichloro-pyrimidine-5-carbaldehyde oxime in 85 ml of thionylchloride prepared at 0° C., was heated to room temperature, then, during 2 hours to reflux. For the working-up, the yellow reaction mixture was cooled to room temperature, then evaporated under reduced pressure to yield 7.57 g of crude 2,4,6-trichloro-5-cyano-pyrimidine as a yellow-brownish solid. For purification, the crude material was chromatographed on silica gel using a 5:1 mixture of cyclohexane and dichloromethane as the eluent giving 4.38 g (0.021 mol, 59% of theory) of 2,4,6-trichloro-5-cyano-pyrimidine as a white solid; MS: $[M]^+=207$.

b) 4-chloro-2,6-bis-cyclopropylamino-pyrimidine-5-carbonitrile

To a solution of 500 mg (2.4 mmol) of 2,4,6-trichloro-5-cyano-pyrimidine in 30 ml of dioxane were added at room temperature 0.84 ml (4.8 mmol) of N-ethyl-diisopropylamine and 0.52 ml (7.2 mmol) of cyclopropylamine. The yellow reaction mixture was stirred at room temperature during 18 hours, then, for working-up, it was evaporated under reduced pressure. The residue obtained was then chromatographed on silica gel using a 3:1 mixture of dichloromethane and hexane as the eluent yielding 328 mg (1.3 mmol, 55% of theory) of 4-chloro-2,6-bis-cyclopropylamino-pyrimidine-5-carbonitrile as a yellow solid; MS: $[M+H]^+=249$.

c) 2,4-Bis-cylopropylamino-6-(4-phenyl-piperazin-1-yl)-pyrimidine-5-carbonitrile In analogy to the procedure described in example 20b, 4-chloro-2,6-bis-cyclopropyl-amino-pyrimidine-5-carbonitrile was treated with 1-phenyl-piperazine and N-ethyl-diisopropylamine in dioxane at 90° C. to yield 2,4-bis-cyclopropylamino-6-(4-phenyl-piperazin-1-yl)-pyrimidine-5-carbonitrile as an amorphous, light yellow solid; MS: $[M+H]^+376$.

EXAMPLE 39

2,4-Bis-(cyclopropylmethyl-amino)-6-(4-phenyl-piperazin-1-yl)-pyrimidine-5-carbonitrile a) 4-chloro-2,6-bis-(cyclopropylmethyl-amino)-pyrimidine-5-carbonitrile

In analogy to the procedure described in example 38b, 2,4,6-trichloro-5-cyano-pyrimidine as prepared in example 38a was treated with aminomethyl-cyclopropane in ethanol at room temperature during 3 hours to yield the 4-chloro-2,6-bis-(cyclopropyl-methyl-amino)-pyrimidine-5-carbonitrile as a white solid; MS: [M+H]$^+$=278.

b) 2,4-Bis-cyclopropylamino-6-(4-phenyl-piperazin-1-yl)-pyrimidine-5-carbonitrile In analogy to the procedure described in example 20b, 4-chloro-2,6-bis-(cyclopropyl-methyl-amino)-pyrimidine-5-carbonitrile was treated with 1-phenyl-piperazine in the presence of N-ethyl-diisopropylamine in dioxane at 80° C. during 18 hours to yield 2,4-bis-(cyclopropylmethyl-amino)-6-(4-phenyl-piperazin-1-yl)-pyrimidine-5-carbonitrile as an amorphous, white solid; MS: [M+H]$^+$=404.

EXAMPLE 40

4-(4-Phenyl-piperazin-1-yl)-2,6-bis-[(pyridin-2-ylmethyl)-amino]-pyrimidine-5-carbonitrile a) 4-chloro-2,6-bis-[(pyridin-2-ylmethyl)-amino]-pyrimidine-5-carbonitrile

In analogy to the procedure described in example 38b, 2,4,6-trichloro-5-cyano-pyrimidine was treated with 2-(aminomethyl)-pyridine in dioxane at room temperature during 18 hours in the presence of N-ethyl-diisopropylamine to yield the 4-chloro-2,6-bis-[(pyridin-2-ylmethyl)-amino]-pyrimidine-5-carbonitrile as a yellow solid; MS: [M+H]$^+$=352.

b) 4-(4-Phenyl-piperazin-1-yl)-2,6-bis-[(pyridin-2-ylmethyl)-amino]-pyrimidine-5-carbonitrile In analogy to the procedure described in example 20b, 4-chloro-2,6-bis-[(pyridin-2-ylmethyl)-amino]-pyrimidine-5-carbonitrile was treated with 1-phenyl-piperazine in the presence of N-ethyl-diisopropylamine in dioxane at 90° C. during 18 hours to yield 4-(4-phenyl-piperazin-1-yl)-2,6-bis-[(pyridin-2-ylmethyl)-amino]-pyrimidine-5-carbonitrile as an amorphous, yellowish solid; MS: [M+H]$^+$=478.

EXAMPLE 41

4-(Cyclopropylmethyl-amino)-2-(2-hydroxy-ethylamino)-6-(4-phenyl-piperazin-1-yl)-pyrimidine-5-carbonitrile a) 4,6-Dichloro-2-(2-hydroxy-ethylamino)-pyrimidine-5-carbonitrile and 2,4-dichloro-6-(2-hydroxy-ethylamino)-pyrimidine-5-carbonitrile A solution of 3.0 g (14.4 mmol) of 2,4,6-trichloro-5-cyano-pyrimidine (example 38a) and 2.51 ml (14.4 mmol) of N-ethyl-diisopropylamine in 90 ml of dioxane was treated at room temperature with 0.88 ml (14.4 mmol) of ethanolamine and stirred during 18 hours. For the working-up, the yellow solution was evaporated and the residue dissolved in 300 ml dichloromethane. The organic phase was washed twice with 50 ml of water, and the two aqueous phases were re-extracted with 50 ml of dichloromethane. The combined organic phases were dried over sodium sulfate and evaporated under reduced pressure. For purification and separation of the two isomers, the crude material (3.2 g) was chromatographed (2×) on silica gel using a 2:1 mixture of hexane and ethyl acetate as the eluent giving 0.85 g (3.6 mmol, 25% of theory) of the 2,4-dichloro-6-(2-hydroxy-ethylamino)-pyrimidine-5-carbonitrile (less polar isomer); MS: [M]$^+$=232; 1.51 g (6.5 mmol, 45% of theory) of the 4,6-dichloro-2-(2-hydroxy-ethylamino)-pyrimidine-5-carbonitrile (more polar isomer); MS: [M]$^+$=232; and 0.26 g (1.1 mmol, 8% of theory) of a mixture of the two isomers.

b) 4-chloro-6-(cyclopropylmethyl-amino)-2-(2-hydroxy-ethylamino)-pyrimidine-5-carbonitrile In analogy to the procedure described in example 38b, 4,6-dichloro-2-(2-hydroxy-ethylamino)-pyrimidine-5-carbonitrile was treated with aminomethyl-cyclopropane in dioxane in the presence of N-ethyl-diisopropylamine at 90° C. to yield 4-chloro-6-(cyclo-propylmethyl-amino)-2-(2-hydroxy-ethylamino)-pyrimidine-5-carbonitrile as an amorphous, white solid; MS: [M+H]$^+$=268.

c) 4-(Cyclopropylmethyl-amino)-2-(2-hydroxy-ethylamino)-6-(4-phenyl-piperazin-1-yl)-pyrimidine-5-carbonitrile In analogy to the procedure described in example 20b, 4-chloro-6-(cyclopropylmethyl-amino)-2-(2-hydroxy-ethylamino)-pyrimidine-5-carbonitrile was treated with 1-phenyl-piperazine in dioxane in the presence of N-ethyl-diisopropylamine at 90° C. to yield 4-(cyclopropylmethyl-amino)-2-(2-hydroxy-ethylamino)-6-(4-phenyl-piperazin-1-yl)-pyrimidine-5-carbonitrile as an amorphous, light brown solid; MS: [M+H]$^+$=394.

EXAMPLE 42

4-(Cyclopropylmethyl-amino)-2-(2-hydroxy-ethylamino)-6-(4-phenyl-piperidin-1-yl)-pyrimidine-5-carbonitrile

In analogy to the procedure described in example 20b, 4-chloro-6-(cyclopropylmethyl-amino)-2-(2-hydroxy-ethylamino)-pyrimidine-5-carbonitrile (example 41b) was treated with 4-phenyl-piperidine in dioxane in the presence of N-ethyl-diisopropylamine at 90° C. to yield the 4-(cyclopropylmethyl-amino)-2-(2-hydroxy-ethylamino)-6-(4-phenyl-piperidin-1-yl)-pyrimidine-5-carbonitrile as an amorphous, white solid;

MS: [M+H]$^+$=393.

EXAMPLE 43

4-(Cyclopropylmethyl-amino)-6-[4-(4-fluoro-phenyl)-3,6-dihydro-2H-pyridin-1-yl]-2-(2-hydroxy-ethylamino)-pyrimidine-5-carbonitrile

In analogy to the procedure described in example 20b, 4-chloro-6-(cyclopropylmethyl-amino)-2-(2-hydroxy-ethylamino)-pyrimidine-5-carbonitrile (example 41b) was treated with 4-(4-fluorophenyl)-1,2,3,6-tetrahydropyridine hydrochloride in dioxane in the presence of N-ethyl-diisopropylamine at 90° C. to yield 4-(cyclopropylmethyl-amino)-6-[4-(4-fluoro-phenyl)-3,6-dihydro-2H-pyridin-1-yl]-2-(2-hydroxy-ethylamino)-pyrimidine-5-carbonitrile as an amorphous, white solid; MS: [M+H]$^+$=409.

EXAMPLE 44

4-cyclopropylamino-6-[4-(4-fluoro-phenyl)-piperidin-1-yl]-2-(2-hydroxy-ethylamino)-pyrimidine-5-carbonitrile a) 4-chloro-6-cyclopropylamino-2-(2-hydroxy-ethylamino)-pyrimidine-5-carbonitrile In analogy to the procedure described in example 38b, 4,6-dichloro-2-(2-hydroxy-ethyl-amino)-pyrimidine-5-carbonitrile was treated with cyclopropylamine in dioxane in the presence of N-ethyl-diisopropylamine at 90° C. to yield 4-chloro-6-cyclopropylamino-2-(2-hydroxy-ethylamino)-pyrimidine-5-carbonitrile as an amorphous, white solid; MS: [M+H]$^+$=254.

b) 4-cyclopropylamino-6-[4-(4-fluoro-phenyl)-piperidin-1-yl]-2-(2-hydroxy-ethylamino)-pyrimidine-5-carbonitrile In analogy to the procedure described in example 20b, the 4-chloro-6-cyclopropylamino-2-(2-hydroxy-ethylamino)-pyrimidine-5-carbonitrile was treated with the 4-(4-fluoro-phenyl)-piperidine hydrochloride in dioxane in the presence of N-ethyl-diisopropyl-amine at 90° C. to yield 4-cyclopropylamino-6-[4-(4-fluoro-phenyl)-piperidin-1-yl]-2-(2-hydroxy-ethylamino)-pyrimidine-5-carbonitrile as an amorphous, light brown solid; MS: $[M+H]^+=397$.

EXAMPLE 45

4-cyclopropylamino-6-[4-(4-fluoro-phenyl)-3,6-dihydro-2H-pyridin-1-yl]-2-(2-hydroxy-ethylamino)-pyrimidine-5-carbonitrile In analogy to the procedure described in example 20b, 4-chloro-6-cyclopropylamino-2-(2-hydroxy-ethylamino)-pyrimidine-5-carbonitrile (example 44a) was treated with 4-(4-fluorophenyl)-1,2,3,6-tetrahydropyridine hydrochloride in dioxane in the presence of N-ethyl-diisopropylamine at 90° C. to yield 4-cyclopropylamino-6-[4-(4-fluoro-phenyl)-3,6-dihydro-2H-pyridin-1-yl]-2-(2-hydroxy-ethylamino)-pyrimidine-5-carbonitrile as an amorphous, white solid; MS: $[M+H]^+=395$.

EXAMPLE 46

4-[4-(4-Fluoro-phenyl)-piperidin-1-yl]-2-(2-hydroxy-ethylamino)-6-[(pyridin-3-ylmethyl)-amino]-pyrimidine-5-carbonitrile a) 4-chloro-2-(2-hydroxy-ethylamino)-6-[(pyridin-3-ylmethyl)-amino]-pyrimidine-5-carbonitrile In analogy to the procedure described in example 38b, 4,6-dichloro-2-(2-hydroxy-ethyl-amino)-pyrimidine-5-carbonitrile was treated with 3-picolylamine in dioxane in the presence of N-ethyl-diisopropylamine at room temperature to yield 4-chloro-2-(2-hydroxy-ethylamino)-6-[(pyridin-3-ylmethyl)-amino]-pyrimidine-5-carbonitrile as a colorless foam.

b) 4-[4-(4-Fluoro-phenyl)-piperidin-1-yl]-2-(2-hydroxy-ethylamino)-6-[(pyridin-3-ylmethyl)-amino]-pyrimidine-5-carbonitrile In analogy to the procedure described in example 20b, 4-chloro-2-(2-hydroxy-ethyl-amino)-6-[(pyridin-3-ylmethyl)-amino]-pyrimidine-5-carbonitrile was treated with 4-(4-fluorophenyl)-piperidine hydrochloride in dioxane in the presence of N-ethyl-diisopropyl-amine at 80° C. to yield the 4-[4-(4-fluoro-phenyl)-piperidin-1-yl]-2-(2-hydroxy-ethyl-amino)-6-[(pyridin-3-ylmethyl)-amino]-pyrimidine-5-carbonitrile as an amorphous, white solid; MS: $[M+H]^+=448$.

EXAMPLE 47

2-cyclopropylamino-4-(2-hydroxy-ethylamino)-6-(4-phenyl-piperazin-1-yl)-pyrimidine-5-carbonitrile a) 4-chloro-2-cyclopropylamino-6-(2-hydroxy-ethylamino)-pyrimidine-5-carbonitrile A solution of 0.5 g (2.0 mmol) of 4-chloro-6-(2-hydroxy-ethylamino)-2-methylsulfanyl-pyrimidine-5-carbonitrile (Timkevicius, S., *Chemija* 1997, 1, 58–61) in 30 ml of dichloromethane was treated at room temperature with 755 mg (70%, 3.0 mmol) of 3-chloro-perbenzoic acid and stirred during 18 hours. For the working-up, the reaction mixture was diluted with 20 ml of dichloromethane and washed rapidly with 50 ml of a cold, saturated aqueous solution of sodium hydrogencarbonate. The organic phase was separated, dried over sodium sulfate, and concentrated under reduced pressure. To the obtained crude 4-chloro-6-(2-hydroxy-ethylamino)-2-methanesulfonyl-pyrimidine-5-carbonitrile were added 5 ml of dichloromethane, then 0.5 ml (3.0 mmol) of N-ethyl-diisopropylamine and 235 mg (4.0 mmol) of cyclopropylamine. The mixture was stirred at room temperature during 18 hours, then it was evaporated under reduced pressure and the residue obtained directly chromatographed on silica gel using a 3:1 mixture of dichloromethane and ethyl acetate as the eluent yielding 340 mg (1.34 mmol, 65% of theory) of the 4-chloro-2-cyclopropylamino-6-(2-hydroxy-ethylamino)-pyrimidine-5-carbonitrile as an amorphous, white solid; MS: $[M+H]^+254$.

b) 2-cyclopropylamino-4-(2-hydroxy-ethylamino)-6-(4-phenyl-piperazin-1-yl)-pyrimidine-5-carbonitrile A mixture of 70 mg (0.27 mmol) of 4-chloro-2-cyclopropylamino-6-(2-hydroxy-ethylamino)-pyrimidine-5-carbonitrile and 0.047 ml (0.27 mmol) of N-ethyl-diisopropylamine in 5 ml of dioxane was treated with 49 mg (0.3 mg) of 1-phenyl-piperazine. The solution was heated to 100° C. during 18 hours, thereafter, for the working-up, evaporated under reduced pressure. For purification, the residue obtained was chromatographed by preparative HPLC on RP18-silica gel using a gradient of a mixture of acetonitrile and water (plus 0.1% of formic acid) as the eluent to give 60 mg (0.16 mmol, 58% of theory) of the 2-cyclopropylamino-4-(2-hydroxy-ethylamino)-6-(4-phenyl-piperazin-1-yl)-pyrimidine-5-carbonitrile as a white powder after lyophilization; MS: $[M+H]^+=380$.

EXAMPLE 48

2-(Cyclopropylmethyl-amino)-4-(2-hydroxy-ethylamino)-6-(4-phenyl-piperazin-1-yl)-pyrimidine-5-carbonitrile a) 4-chloro-2-(cyclopropylmethyl-amino)-6-(2-hydroxy-ethylamino)-pyrimidine-5-carbonitrile In analogy to the procedure described in example 47a, the crude 4-chloro-6-(2-hydroxy-ethylamino)-2-methanesulfonyl-pyrimidine-5-carbonitrile was treated with amino-methyl-cyclopropane in dioxane in the presence of N-ethyl-diisopropylamine at 40° C. to yield 4-chloro-2-(cyclopropylmethyl-amino)-6-(2-hydroxy-ethylamino)-pyrimidine-5-carbonitrile as an amorphous, white solid; MS: $[M+H]^+=268$.

b) 2-(Cyclopropylmethyl-amino)-4-(2-hydroxy-ethylamino)-6-(4-phenyl-piperazin-1-yl)-pyrimidine-5-carbonitrile In analogy to the procedure described in example 47b, 4-chloro-2-(cyclopropylmethyl-amino)-6-(2-hydroxy-ethylamino)-pyrimidine-5-carbonitrile was treated with 1-phenyl-piperazine in dioxane in the presence of N-ethyl-diisopropylamine at 100° C. to yield 2-(cyclopropylmethyl-amino)-4-(2-hydroxy-ethylamino)-6-(4-phenyl-piperazin-1-yl)-pyrimidine-5-carbonitrile as an amorphous, white solid; MS: $[M+H]^+=394$.

EXAMPLE 49

4-(2-Hydroxy-ethylamino)-6-(4-phenyl-piperazin-1-yl)-2-[(pyridin-3-ylmethyl)-amino]-pyrimidine-5-carbonitrile b) 4-chloro-6-(2-hydroxy-ethylamino)-2-[(pyridin-3-ylmethyl)-amino]-pyrimidine-5-carbonitrile In analogy to the procedure described in example 47a, the crude 4-chloro-6-(2-hydroxy-ethylamino)-2-methanesulfonyl-pyrimidine-5-carbonitrile was treated with 3-picolyl-amine in dioxane in the presence of N-ethyl-diisopropylamine at 40° C. to yield 4-chloro-6-(2-hydroxy-ethylamino)-2-[(pyridin-3-ylmethyl)-amino]-pyrimidine-5-carbonitrile as a brown solid which was used in the next step without further purification and characterization.

b) 4-(2-Hydroxy-ethylamino)-6-(4-phenyl-piperazin-1-yl)-2-[(pyridin-3-ylmethyl)-amino]-pyrimidine-5-carbonitrile In analogy to the procedure described in example 47b, the crude 4-chloro-6-(2-hydroxy-ethylamino)-2-[(pyridin-3-ylmethyl)-amino]-pyrimidine-5-carbonitrile was treated with 1-phenyl-piperazine in dioxane in the presence of N-ethyl-diisopropylamine at 100° C. to yield 4-(2-hydroxy-ethylamino)-6-(4-phenyl-piperazin-1-yl)-2-[(pyridin-3-ylmethyl)-amino]-pyrimidine-5-carbonitrile as an amorphous, light brown solid; MS: $[M+H]^+=431$.

EXAMPLE 50

2-(Cyclopropylmethyl-amino)-4-[4-(4-fluoro-phenyl)-piperazin-1-yl]-6-(2-hydroxy-ethylamino)-pyrimidine-5-carbonitrile In analogy to the procedure described in example 47b, 4-chloro-2-(cyclopropylmethyl-amino)-6-(2-hydroxy-ethylamino)-pyrimidine-5-carbonitrile (example 48a) was treated with the 1-(4-fluorophenyl)-piperazine in dioxane in the presence of N-ethyl-diisopropyl-amine at 100° C. to yield 2-(cyclopropylmethyl-amino)-4-[4-(4-fluoro-phenyl)-piperazin-1-yl]-6-(2-hydroxy-ethylamino)-pyrimidine-5-carbonitrile as an amorphous, white solid; MS: $[M+H]^+=412$.

EXAMPLE 51

2-cyclopropylamino-4-[4-(4-fluoro-phenyl)-piperazin-1-yl]-6-(2-hydroxy-ethylamino)-pyrimidine-5-carbonitrile In analogy to the procedure described in example 47b, 4-chloro-2-cyclopropylamino-6-(2-hydroxy-ethylamino)-pyrimidine-5-carbonitrile (example 47a) was treated with the 1-(4-fluorophenyl)-piperazine in dioxane in the presence of N-ethyl-diisopropylamine at 100° C. to yield the 2-cyclopropylamino-4-[4-(4-fluoro-phenyl)-piperazin-1-yl]-6-(2-hydroxy-ethylamino)-pyrimidine-5-carbonitrile as an amorphous, white solid; MS: $[M+H]^+=398$.

EXAMPLE 52

4-[4-(4-Fluoro-phenyl)-piperazin-1-yl]-6-(2-hydroxy-ethylamino)-2-[(pyridin-3-ylmethyl)-amino]-pyrimidine-5-carbonitrile In analogy to the procedure described in example 47b, the crude 4-chloro-6-(2-hydroxy-ethylamino)-2-[(pyridin-3-ylmethyl)-amino]-pyrimidine-5-carbonitrile (example 49a) was treated with 1-(4-fluorophenyl)-piperazine in dioxane in the presence of N-ethyl-diisopropylamine at 90° C. to yield 4-[4-(4-fluoro-phenyl)-piperazin-1-yl]-6-(2-hydroxy-ethylamino)-2-[(pyridin-3-ylmethyl)-amino]-pyrimidine-5-carbonitrile as an amorphous, light brown powder; MS: $[M+H]^+=449$.

EXAMPLE 53

2-(Cyclopropylmethyl-amino)-4-(2-hydroxy-ethylamino)-6-(4-phenyl-piperidin-1-yl)-pyrimidine-5-carbonitrile a) 4-(2-Hydroxy-ethylamino)-2-methylsulfanyl-6-(4-phenyl-piperidin-1-yl)-pyrimidine-5-carbonitrile A solution of 0.47 g (1.9 mmol) of 4-chloro-6-(2-hydroxy-ethylamino)-2-methylsulfanyl-pyrimidine-5-carbonitrile (Timkevicius, S., Chemija 1997, 1, 58–61) and 0.33 ml (1.9 mmol) of N-ethyl-diisopropylamine in 5 ml of dichloromethane was treated at 30° C. with 310 mg (1.9 mmol) of 4-phenyl-piperidine and stirred during 7 hours. For the working-up, the reaction mixture was evaporated under reduced pressure, and the residue obtained was directly chromatographed on silica gel using a 99:1 mixture of dichloromethane and methanol as the eluent yielding 490 mg (1.33 mmol, 70% of theory) of the 4-(2-hydroxy-ethylamino)-2-methylsulfanyl-6-(4-phenyl-piperidin-1-yl)-pyrimidine-5-carbonitrile as an amorphous, white solid; MS: $[M+H]^+=370$.

b) 2-(Cylopropylmethyl-amino)-4-(2-hydroxy-ethylamino)-6-(4-phenyl-piperidin-1-yl)-pyrimidine-5-carbonitrile A solution of 0.1 g (0.26 mmol) of 4-(2-hydroxy-ethylamino)-2-methylsulfanyl-6-(4-phenyl-piperidin-1-yl)-pyrimidine-5-carbonitrile in 3 ml of dichloromethane was treated at 0° C. with 95 mg (0.39 mmol) of 3-chloro-perbenzoic acid, and, thereupon, stirred at room temperature during 3 hours. For the working-up, the reaction mixture was diluted with 5 ml of dichloromethane and washed rapidly with 5 ml of a cold, saturated aqueous solution of sodium hydrogencarbonate. The organic phase was separated, dried over sodium sulfate, and concentrated under reduced pressure.

To the obtained crude 4-(2-hydroxy-ethylamino)-2-methanesulfonyl-6-(4-phenyl-piperidin-1-yl)-pyrimidine-5-carbonitrile were added 5 ml of dichloromethane and 0.045 ml (0.5 mmol) of aminomethyl-cyclopropane. The mixture was stirred at 40° C. during 18 hours, then it was evaporated under reduced pressure and the residue obtained directly chromato-graphed by preparative HPLC on RP 18-silica gel using a gradient of a mixture of acetonitrile and water (plus 0.1% of formic acid) as the eluent to give 35 mg (0.89 mmol, 35% of theory), of the 2-(cyclopropylmethyl-amino)-4-(2-hydroxy-ethylamino)-6-(4-phenyl-piperidin-1-yl)-pyrimidine-5-carbonitrile as an amorphous, white solid; MS: $[M]^+=392$.

EXAMPLE 54

4-(2-Hydroxy-ethylamino)-6-(4-phenyl-piperidin-1-yl)-2-[(pyridin-3-ylmethyl)-amino]-pyrimidine-5-carbonitrile In analogy to the procedure described in example 47b, the crude 4-chloro-6-(2-hydroxy-ethylamino)-2-[(pyridin-3-ylmethyl)-amino]-pyrimidine-5-carbonitrile (example 49a) was treated with 4-phenyl-piperidine in dioxane in the presence of N-ethyl-diisopropylamine at 100° C. to yield 4-(2-hydroxy-ethylamino)-6-(4-phenyl-piperidin-1-yl)-2-[(pyridin-3-ylmethyl)-amino]-pyrimidine-5-carbonitrile as an amorphous, brownish powder; MS: $[M+H]^+=430$.

EXAMPLE 55

2-cyclopropylamino-4-(2-hydroxy-ethylamino)-6-(4-phenyl-piperidin-1-yl)-pyrimidine-5-carbonitrile In analogy to the procedure described in example 47b, 4-chloro-2-cyclopropylamino-6-(2-hydroxy-ethylamino)-pyrimidine-5-carbonitrile (example 47a) was treated with 4-phenyl-piperidine in dioxane in the presence of N-ethyl-diisopropylamine at 100° C. to yield 2-cyclopropylamino-4-(2-hydroxy-ethylamino)-6-(4-phenyl-piperidin-1-yl)-pyrimidine-5-carbonitrile as an amorphous, white solid; MS: $[M+H]^+=379$.

EXAMPLE 56

4-[4-(4-Fluoro-phenyl)-piperidin-1-yl]-6-(2-hydroxy-ethylamino)-2-[(pyridin-3-ylmethyl)-amino]-pyrimidine-5-carbonitrile In analogy to the procedure described in example 47b, the crude 4-chloro-6-(2-hydroxy-ethylamino)-2-[(pyridin-3- ylmethyl)-amino]-pyrimidine-5-carbonitrile (example 49a) was treated with the 4-(4-fluorophenyl)-piperidine in dioxane in the presence of N-ethyl-diisopropylamine at 100° C. to yield 4-[4-(4-fluoro-phenyl)-piperidin-1-yl]-6-(2-hydroxy-ethylamino)-2-[(pyridin-3-ylmethyl)-amino]-pyrimidine-5-carbonitrile as an amorphous, light brown; MS: [M+H]$^+$=448.

EXAMPLE 57

2-(Cyclopropylmethyl-amino)-4-[4-(4-fluoro-phenyl)-piperidin-1-yl]-6-(2-hydroxy-ethylamino)-pyrimidine-5-carbonitrile a) 4-chloro-6-[4-(4-fluoro-phenyl)-piperidin-1-yl]-2-methylsulfanyl-pyrimidine-5-carbonitrile A dispersion of 0.5 g (2.3 mmol) of 4,6-dichloro-2-methylsulfanyl-pyrimidine-5-carbonitrile (*J. Heterocycl. Chem.* 1971, 8, 445–453) and 0.65 g (5.0 mmol) of N-ethyl-diisopropylamine in 40 ml of dioxane was treated at room temperature with 0.54 g (5.0 mmol) of 4-(4-fluorophenyl)-piperidine hydrochloride during 18 h. For the working-up, the reaction mixture was evaporated, and, thereafter, the residue obtained was directly chromatographed on silica gel using toluene as the eluent yielding 660 mg (1.8 mmol, 80% of theory) of 4-chloro-6-[4-(4-fluoro-phenyl)-piperidin-1-yl]-2-methylsulfanyl-pyrimidine-5-carbonitrile as an amorphous, white solid; MS: [M+H]$^+$=363.

b) 4-[4-(4-Fluoro-phenyl)-piperidin-1-yl]-6-(2-hydroxy-ethylamino)-2-methylsulfanyl-pyrimidine-5-carbonitrile A dispersion of 200 mg (0.55 mmol) of 4-chloro-6-[4-(4-fluoro-phenyl)-piperidin-1-yl]-2-methylsulfanyl-pyrimidine-5-carbonitrile and 84 mg (0.6 mmol) of N-ethyl-diisopropylamine in 4 ml of dioxane was treated at 65° C. with 37 mg (0.6 mmol) of ethanolamine during 18 h. For the working-up, the reaction mixture was evaporated, and, thereafter, the residue obtained was directly chromatographed on silica gel using a 5:1 mixture of toluene and ethyl acetate as the eluent yielding 177 mg (0.46 mmol, 83% of theory) of the 4-[4-(4-fluoro-phenyl)-piperidin-1-yl]-6-(2-hydroxy-ethylamino)-2-methylsulfanyl-pyrimidine-5-carbonitrile as a yellowish oil which crystallized on standing. MS: [M+H]$^+$=388.

c) 2-(Cyclopropylmethyl-amino)-4-[4-(4-fluoro-phenyl)-piperidin-1-yl]-6-(2-hydroxy-ethylamino)-pyrimidine-5-carbonitrile A solution of 150 mg (0.4 mmol) of 4-[4-(4-fluoro-phenyl)-piperidin-1-yl]-6-(2-hydroxy-ethylamino)-2-methylsulfanyl-pyrimidine-5-carbonitrile in 8 ml of dichloromethane was cooled to 0° C. and treated with a solution of 172 mg (70%, 0.7 mmol) of 3-chloro-perbenzoic acid. The reaction mixture was warmed to room temperature and stirring was continued during 4 hours (completion of the reaction was checked by TLC). For the working-up, the reaction mixture was diluted with 20 ml of dichloromethane and washed rapidly with 10 ml of a cold, saturated aqueous solution of sodium hydrogencarbonate. The organic phase was separated, dried over sodium sulfate., and evaporated under reduced pressure. Thereupon, without further working-up, the residue obtained was dissolved in 15 ml of dioxane and the solution was treated with 39 mzg (0.52 mmol) of aminomethyl-cyclopropane. After 18 hours at 40° C., the solution was evaporated and the residue obtained was then directly chromatographed by preparative HPLC on RP18-silica gel using a gradient of a mixture of acetonitrile and water (plus 0.1% of formic acid) as the eluent to give 48 mg (0.12 mmol, 25% of theory) of the 2-(cyclopropylmethyl-amino)-4-[4-(4-fluoro-phenyl)-piperidin-1-yl]-6-(2-hydroxy-ethylamino)-pyrimidine-5-carbonitrile as a white solid; MS: [M+H]$^+$=411.

EXAMPLE 58

2-cyclopropylamino-4-[4-(4-fluoro-phenyl)-piperidin-1-yl]-6-(2-hydroxy-ethylamino)-pyrimidine-5-carbonitrile In analogy to the procedure described in example 47b, 4-chloro-2-cyclopropylamino-6-(2-hydroxy-ethylamino)-pyrimidine-5-carbonitrile (example 47a) was treated with the 4-(4-fluorophenyl)-piperidine in dioxane in the presence of N-ethyl-diisopropylamine at 100° C. to yield the 2-cyclopropylamino-4-[4-(4-fluoro-phenyl)-piperidin-1-yl]-6-(2-hydroxy-ethylamino)-pyrimidine-5-carbonitrile as an amorphous, white solid; MS: [M+H]$^+$=397.

EXAMPLE 59

4-(4-Phenyl-piperidin-1-yl)-2-[(pyridin-3-ylmethyl)-amino]-6-(2,2,2-trifluoro-ethoxy)-pyrimidine-5-carbonitrile a) 4-chloro-2-methylsulfanyl-6-(4-phenyl-piperidin-1-yl)-pyrimidine-5-carbonitrile In analogy to the procedure described in example 57a, the 4,6-dichloro-2-methylsulfanyl-pyrimidine-5-carbonitrile (*J. Heterocycl. Chem.* 1971, 8, 445–453) was treated with 4-phenyl-piperidine in the presence of N-ethyl-diisopropylamine at room temperature during 18 hours to yield the 4-chloro-2-methylsulfanyl-6-(4-phenyl-piperidin-1-yl)-pyrimidine-5-carbonitrile as an amorphous, white solid; MS: [M+H]$^+$=345.

b) 2-Methylsulfanyl-4-(4-phenyl-piperidin-1-yl)-6-(2,2,2-trifluoro-ethoxy)-pyrimidine-5-carbonitrile A solution of 56 mg (0.55 mmol) of 2,2,2-trifluoroethanol in 5 ml of tetrahydrofurane was cooled to 0° C. and treated under an argon atmosphere with 23 mg (0.52 mmol) of sodium hydride (55% dispersion in oil). The mixture was kept at 0° C. during 10 min, then a solution of 200 mg (0.58 mmol) of 4-chloro-2-methylsulfanyl-6-(4-phenyl-piperidin-1-yl)-pyrimidine-5-carbonitrile in 5 ml of tetrahydrofurane was added and, thereupon, the mixture was warmed to room temperature and stirring continued during 36 hours. For the working-up, the reaction mixture was evaporated and the residue obtained was directly chromatographed on silica gel using a 9:1 mixture of hexane and ethyl acetate as the eluent yielding 142 mg (0.35 mmol, 60% of theory) of the 2-methylsulfanyl-4-(4-phenyl-piperidin-1-yl)-6-(2,2,2-trifluoro-ethoxy)-pyrimidine-5-carbonitrile as an amorphous, white solid; MS: [M+H]$^+$=409.

c) 4-(4-Phenyl-piperidin-1-yl)-2-[(pyridin-3-ylmethyl)-amino]-6-(2,2,2-trifluoro-ethoxy)-pyrimidine-5-carbonitrile In analogy to the procedure described in example 57c, the 2-methylsulfanyl-4-(4-phenyl-piperidin-1-yl)-6-(2,2,2-trifluoro-ethoxy)-pyrimidine-5-carbonitrile was oxidized by 3-chloro-perbenzoic acid to the 2-methanesulfonyl-4-(4-phenyl-piperidin-1-yl)-6-(2,2,2-trifluoro-ethoxy)-pyrimidine-5-carbonitrile which was then treated in crude form with 3-picolylamine in dioxane at 40° C. during 18 hours to yield the 4-(4-phenyl-piperidin-1-yl)-2-[(pyridin-3-ylmethyl)-amino]-6-(2,2,2-trifluoro-ethoxy)-pyrimidine-5-carbonitrile as an amorphous, light brown solid; MS: [M+H]$^+$=469.

EXAMPLE 60

2-(2-Hydroxy-ethylamino)-4-(4-phenyl-piperidin-1-yl)-6-(2,2,2-trifluoro-ethoxy)-pyrimidine-5-carbonitrile In analogy to the procedure described in example 57c, 2-methylsulfanyl-4-(4-phenyl-piperidin-1-yl)-6-(2,2,2-trifluoro-ethoxy)-pyrimidine-5-carbonitrile was oxidized by 3-chloro-perbenzoic acid to 2-methanesulfonyl-4-(4-phenyl-piperidin-1-yl)-6-(2,2,2-trifluoro-ethoxy)-pyrimidine-5-carbonitrile which was then treated in crude form with ethanolamine in dioxane at 40° C. during 18 hours to yield the 2-(2-hydroxy-ethylamino)-4-(4-phenyl-piperidin-1-yl)-6-(2,2,2-trifluoro-ethoxy)-pyrimidine-5-carbonitrile as an amorphous, white solid; MS: [M+H]$^+$=422.

EXAMPLE 61

4-[4-(4-Fluoro-phenyl)-piperidin-1-yl]-2-[(pyridin-3-ylmethyl)-amino]-6-(2,2,2-trifluoro-ethoxy)-pyrimidine-5-carbonitrile a) 4-[4-(4-Fluoro-phenyl)-piperidin-1-yl]-2-methylsulfanyl-6-(2,2,2-trifluoro-ethoxy)-pyrimidine-5-carbonitrile In analogy to the procedure described in example 59b, 4-chloro-6-[4-(4-fluoro-phenyl)-piperidin-1-yl]-2-methylsulfanyl-pyrimidine-5-carbonitrile (example 57a) was treated with 2,2,2-trifluoroethanolate in tetrahydrofurane at room temperature during 18 hours to yield the 4-phenyl-piperidine in the presence of N-ethyl-diisopropylamine at room temperature during 18 hours to yield 4-[4-(4-fluoro-phenyl)-piperidin-1-yl]-2-methylsulfanyl-6-(2,2,2-trifluoro-ethoxy)-pyrimidine-5-carbonitrile as an amorphous, yellow solid; MS: $[M+H]^+=427$.

b) 4-[4-(4-Fluoro-phenyl)-piperidin-1-yl]-2-[(pyridin-3-ylmethyl)-amino]-6-(2,2,2-trifluoro-ethoxy)-pyrimidine-5-carbonitrile In analogy to the procedure described in example 57c, the 4-[4-(4-fluoro-phenyl)-piperidin-1-yl]-2-methylsulfanyl-6-(2,2,2-trifluoro-ethoxy)-pyrimidine-5-carbonitrile was oxidized by 3-chloro-perbenzoic acid to 4-[4-(4-fluoro-phenyl)-piperidin-1-yl]-2-methanesulfonyl-6-(2,2,2-trifluoro-ethoxy)-pyrimidine-5-carbonitrile which was then treated with 3-picolylamine in dioxane at 40° C. during 18 hours to yield the 4-[4-(4-fluoro-phenyl)-piperidin-1-yl]-2-[(pyridin-3-ylmethyl)-amino]-6-(2,2,2-trifluoro-ethoxy)-pyrimidine-5-carbonitrile as an amorphous, light brown solid; MS: $[M+H]^+=487$.

EXAMPLE 62

4-[4-(4-Fluoro-phenyl)-piperidin-1-yl]-2-(2-hydroxy-ethylamino)-6-(2,2,2-trifluoro-ethoxy)-pyrimidine-5-carbonitrile In analogy to the procedure described in example 57c, 4-[4-(4-fluoro-phenyl)-piperidin-1-yl]-2-methylsulfanyl-6-(2,2,2-trifluoro-ethoxy)-pyrimidine-5-carbonitrile (example 61a) was oxidized by 3-chloro-perbenzoic acid to the 4-[4-(4-fluoro-phenyl)-piperidin-1-yl]-2-methanesulfonyl-6-(2,2,2-trifluoro-ethoxy)-pyrimidine-5-carbonitrile which was then treated with ethanolamine in dioxane at 40° C. during 4 hours to yield 4-[4-(4-fluoro-phenyl)-piperidin-1-yl]-2-(2-hydroxy-ethylamino)-6-(2,2,2-trifluoro-ethoxy)-pyrimidine-5-carbonitrile as a clorless oil; MS: $[M+H]^+=440$.

EXAMPLE 63

4-chloro-2-(cyclopropylmethyl-amino)-6-(4-phenyl-piperazin-1-yl)-pyrimidine-5-carbonitrile a) 4,6-Dichloro-2-(cylopropylmethyl-amino)-pyrimidine-5-carbonitrile A solution of 1.0 g (5.4 mmol) of 4,6-dichloro-2-methylsulfanyl-pyrimidine-5-carbonitrile (*J. Heterocycl. Chem.* 1971, 8, 445–453) in 30 ml of dichloromethane was cooled to 0° C. and treated with 1.59 g (70%, 6.4 mmol) of 3-chloro-perbenzoic acid. The reaction mixture was warmed to room temperature and stirring was continued during 3 hours (completion of the reaction was checked by TLC). For the working-up, the reaction mixture was diluted with 70 ml of dichloromethane and washed rapidly with 30 ml of a cold, saturated aqueous solution of sodium hydrogencarbonate. The organic phase was separated and dried over sodium sulfate. Thereupon, without further working-up, the solution was treated with 385 mg (5.4 mmol) of aminomethyl-cyclopropane. After 18 hours at room temperature, the solution was evaporated and the residue obtained was then chromatographed on silica gel using a 10:1 mixture of hexane and ethyl acetate as the eluent giving 450 mg (1.85 mmol, 34% of theory) of the 4,6-dichloro-2-(cyclopropyl-methyl-amino)-pyrimidine-5-carbonitrile as a white powder; MS: $[M]^+=243$.

b) 4-chloro-2-(cyclopropylmethyl-amino)-6-(4-phenyl-piperazin-1-yl)-pyrimidine-5-carbonitrile In analogy to the procedure described in example 20b, 4,6-dichloro-2-(cyclopropyl-methyl-amino)-pyrimidine-5-carbonitrile was treated with 1-phenyl-piperazine in the presence of N-ethyl-diisopropylamine in dioxane at room temperature during 18 hours to yield 4-chloro-2-(cyclopropylmethyl-amino)-6-(4-phenyl-piperazin-1-yl)-pyrimidine-5-carbonitrile as an amorphous, white solid; MS: $[M+H]^+=369$.

EXAMPLE 64

4-chloro-2-(cyclopropylmethyl-amino)-6-[4-(4-fluoro-phenyl)-piperazin-1-yl]-pyrimidine-5-carbonitrile In analogy to the procedure described in example 20b, 4,6-dichloro-2-(cyclopropyl-methyl-amino)-pyrimidine-5-carbonitrile (example 63a) was treated with 1-(4-fluoro-phenyl)-piperazine in the presence of N-ethyl-diisopropylamine in dioxane at 90° C. to yield 4-chloro-2-(cyclopropylmethyl-amino)-6-[4-(4-fluoro-phenyl)-piperazin-1-yl]-pyrimidine-5-carbonitrile as an amorphous, white solid; MS: $[M+H]^+=387$.

EXAMPLE 65

4-chloro-2-(2-hydroxy-ethylamino)-6-(4-phenyl-piperazin-1-yl)-pyrimidine-5-carbonitrile In analogy to the procedure described in example 20b, 4,6-dichloro-2-(2-hydroxy-ethylamino)-pyrimidine-5-carbonitrile (example 41a) was treated with 1-phenyl-piperazine in dioxane in the presence of N-ethyl-diisopropylamine at room temperature to yield 4-chloro-2-(2-hydroxy-ethylamino)-6-(4-phenyl-piperazin-1-yl)-pyrimidine-5-carbonitrile as an amorphous, white solid; MS: $[M+H]^+=359$.

EXAMPLE 66

4-chloro-6-[4-(4-fluoro-phenyl)-piperazin-1-yl]-2-(2-hydroxy-ethylamino)-pyrimidine-5-carbonitrile In analogy to the procedure described in example 20b, 4,6-dichloro-2-(2-hydroxy-ethylamino)-pyrimidine-5-carbonitrile (example 41a) was treated with 4-(4-fluoro-phenyl)-piperazine in dioxane in the presence of N-ethyl-diisopropylamine at room temperature to yield 4-chloro-6-[4-(4-fluoro-phenyl)-piperazin-1-yl]-2-(2-hydroxy-ethylamino)-pyrimidine-5-carbonitrile as an amorphous, white solid; MS: $[M+H]^+=377$.

EXAMPLE 67

4-chloro-2-(2-hydroxy-ethylamino)-6-(4-phenyl-piperidin-1-yl)-pyrimidine-5-carbonitrile In analogy to the procedure described in example 20b, 4,6-dichloro-2-(2-hydroxy-ethylamino)-pyrimidine-5-carbonitrile (example 41a) was treated with 4-phenyl-piperidine in dioxane in the presence of N-ethyl-diisopropylamine at room temperature to yield 4-chloro-2-(2-hydroxy-ethylamino)-6-(4-phenyl-piperidin-1-yl)-pyrimidine-5-carbonitrile as an amorphous, white solid; MS: $[M+H]^+=358$.

EXAMPLE 68

4-chloro-6-[4-(4-fluoro-phenyl)-piperidin-1-yl]-2-(2-hydroxy-ethylamino)-pyrimidine-5-carbonitrile In analogy to the procedure described in example 20b, 4,6-dichloro-2-(2-hydroxy-ethylamino)-pyrimidine-5-carbonitrile (example 41a) was treated with 4-(4-fluoro-phenyl)-piperidine hydrochloride in dioxane in the presence of N-ethyl-diisopropyl-amine at room temperature to yield 4-chloro-6-[4-(4-fluoro-phenyl)-piperidin-1-yl]-2-(2-hydroxy-ethylamino)-pyrimidine-5-carbonitrile as a white lyophilisate; MS: $[M+H]^+$=376.

EXAMPLE 69

2-Amino-4-methylsulfanyl-6-(4-phenyl-piperazin-1-yl)-pyrimidine-5-carbonitrile

In analogy to the procedure described in example 20b, the 2-amino-4-bromo-6-methylsulfanyl-pyrimidine-5-carbonitrile, which was prepared from 2,2-dicyano-1-methylsulfanyl-vinyl-cyanamide sodium salt as described in European Patent Application EP 244 360 A2 (1987) with excess hydrogen bromide in acetic acid between 0° C. and room temperature, was treated with 1-phenyl-piperazine in dioxane in the presence of N-ethyl-diisopropylamine at room temperature during 36 hours to yield the 2-amino-4-methyl-sulfanyl-6-(4-phenyl-piperazin-1-yl)-pyrimidine-5-carbonitrile as a yellow solid; MS: $[M+H]^+$=327.

EXAMPLE 70

2-Amino-4-[4-(4-fluoro-phenyl)]-piperazin-1-yl]-6-methylsulfanyl-pyrimidine-5-carbonitrile In analogy to the procedure described in example 20b, 2-amino-4-bromo-6-methyl-sulfanyl-pyrimidine-5-carbonitrile (see example 69) was treated with 1-(4-fluorophenyl)-piperazine in dioxane in the presence of N-ethyl-diisopropylamine at room temperature during 36 hours to yield 2-amino-4-[4-(4-fluoro-phenyl)-piperazin-1-yl]-6-methyl-sulfanyl-pyrimidine-5-carbonitrile as a yellow powder; MS: $[M+H]^+$=345.

EXAMPLE 71

2-Amino-4-[4-(2-fluoro-phenyl)-piperazin-1-yl]-6-methylsulfanyl-pyrimidine-5-carbonitrile In analogy to the procedure described in example 20b, 2-amino-4-bromo-6-methyl-sulfanyl-pyrimidine-5-carbonitrile (see example 69) was treated with the 1-(2-fluoro-phenyl)-piperazine in dioxane in the presence of N-ethyl-diisopropylamine at room temperature during 36 hours to yield the 2-amino-4-[4-(2-fluoro-phenyl)-piperazin-1-yl]-6-methylsulfanyl-pyrimidine-5-carbonitrile as a yellow solid; MS: $[M+H]^+$=345.

EXAMPLE 72

2-Amino-4-methylsulfanyl-6-(4-phenyl-piperidin-1-yl)-pyrimidine-5-carbonitrile

In analogy to the procedure described in example 20b, 2-amino-4-bromo-6-methyl-sulfanyl-pyrimidine-5-carbonitrile (see example 69) was treated with 4-phenyl-piperidine in dioxane in the presence of N-ethyl-diisopropylamine at room temperature during 36 hours to yield 2-amino-4-methylsulfanyl-6-(4-phenyl-piperidin-1-yl)-pyrimidine-5-carbonitrile as a yellow foam; MS: $[M+H]^+$=326.

EXAMPLE 73

2-Amino-4-[4-(4-fluoro-phenyl)-piperidin-1-yl]-6-methylsulfanyl-pyrimidine-5-carbonitrile In analogy to the procedure described in example 20b, the 2-amino-4-bromo-6-methylsulfanyl-pyrimidine-5-carbonitrile (see example 69) was treated with the 4-(4-fluorophenyl)-piperidine hydrochloride in dioxane in the presence of N-ethyl-diiso-propylamine at room temperature during 36 hours to yield 2-amino-4-[4-(4-fluoro-phenyl)-piperidin-1-yl]-6-methylsulfanyl-pyrimidine-5-carbonitrile as a yellow solid; MS: $[M+H]^+$=344.

EXAMPLE 74

2-Amino-4-[4-(4-fluoro-phenyl)-3,6-dihydro-2H-pyridin-1-yl]-6-methylsulfanyl-pyrimidine-5-carbonitrile In analogy to the procedure described in example 20b, 2-amino-4-bromo-6-methyl-sulfanyl-pyrimidine-5-carbonitrile (see example 69) was treated with 4-(4-fluorophenyl)-1,2,3,6-tetrahydro-pyridine hydrochloride in dioxane in the presence of N-ethyl-diisopropylamine at room temperature during 36 hours to yield 2-amino-4-[4-(4-fluoro-phenyl)-3,6-dihydro-2H-pyridin-1-yl]-6-methylsulfanyl-pyrimidine-5-carbonitrile as a yellow solid; MS: $[M+H]^+$=342.

EXAMPLE 75

5'-Ethyl-6'-methyl-4-phenyl-3,4,5,6-tetrahydro-2H-[1,2']bipyrazinyl-3'-carbonitrile and 6'-ethyl-5'-methyl-4-phenyl-3,4,5,6-tetrahydro-2H-[1,2']bipyrazinyl-3'-carbonitrile a) 5-Ethyl-6-methyl-3-oxo-3,4-dihydro-pyrazine-2-carboxylic acid amide and 6-ethyl-5-methyl-3-oxo-3,4-dihydro-pyrazine-2-carboxylic acid amide A solution of 8.32 g (80.61 mmol) 2-amino-malonic acid diamide and 9.75 g (83.26 mmol) of 2,3-pentanedione in 60 ml of water was heated under reflux for 18 hours. After cooling to room temperature the crystals formed were collected by filtration and dried in vacuo. There were thus obtained 9.52 g (52.54 mmol, 65.2% of theory) of a 3:2 or a 2:3 mixture of the 6-ethyl-5-methyl-3-oxo-3,4-dihydro-pyrazine-2-carboxylic acid amide and the 5-ethyl-6-methyl-3-oxo-3,4-dihydro-pyrazine-2-carboxylic acid amide as yellow solid; MS: 181 $(M)^+$.

b) 3-chloro-6-ethyl-5-methyl-pyrazine-2-carbonitrile and 3-chloro-5-ethyl-6-methyl-pyrazine-2-carbonitrile (1:1 mixture of the two isomers)

1.81 g (10.0 mmol) of the 3:2 or 2:3 mixture of the 6-ethyl-5-methyl-3-oxo-3,4-dihydro-pyrazine-2-carboxylic acid amide and the 5-ethyl-6-methyl-3-oxo-3,4-dihydro-pyrazine-2-carboxylic acid amide were suspended in 4.2 ml (30 mmol) of triethylamine. Then, 30 ml of phosphorus oxychloride were slowly added between 0° C. and 5° C. and the reaction mixture heated under reflux for 3 hours. It was then cooled to 20° C., 5.3 g (25 mmol) of phosphorus pentachloride were added and the reaction mixture heated again under reflux for 3 hours. It was then added to water while maintaining a temperature of 20° C. to 25° C. The aqueous phase was subsequently extracted 5 times with 100 ml of ether and the combined ether phases washed with saturated sodium hydrogen carbonate solution, dried over magnesium sulfate and evaporated under reduced pressure. The residue formed was chromatographed on silica gel using a 1:1 v/v mixture of dichloromethane and hexane as eluent giving 1.0 g (5.5 mmol, 55% of theory) of a 1:1 mixture of the 3-chloro-6-ethyl-5-methyl-pyrazine-2-carbonitrile and the 3-chloro-5-ethyl-6-methyl-pyrazine-2-carbonitrile in form of an orange red oil; MS: 181 (M)$^+$.

c) 5'-Ethyl-6'-methyl-4-phenyl-3,4,5,6-tetrahydro-2H-[1,2'] bipyrazinyl-3'-carbonitrile and 6'-ethyl-5'-methyl-4-phenyl-3 4,5,6-tetrahydro-2H-[1,2']bipyrazinyl-3'-carbonitrile 0.416 mg (3.0 mmol) of potassium carbonate were added to a solution of 0.182 g (1.0 mmol) of the 1:1 mixture of the 3-chloro-6-ethyl-5-methyl-pyrazine-2-carbonitrile and the 3-chloro-5-ethyl-6-methyl-pyrazine-2-carbonitrile and of 0.199 g (1.2 mmol) of 1-phenylpiperazine in 10.0 ml of N,N-dimethylformamide and the reaction mixture was stirred at room temperature for 16 hours. It was subsequently poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with a 4:1 to 0:100 v/v gradient of hexane and dichloromethane as the eluent giving 0.067 g (0.218 mmol, 21.8% of theory) of the 5'-ethyl-6'-methyl-4-phenyl-3,4,5,6-tetrahydro-2H-[1,2']bipyrazinyl-3'-carbonitrile as orange oil; MS: 308 (M+H)$^+$; and 0.043 g (0.14 mmol, 14% of theory) of the 6'-ethyl-5'-methyl-4-phenyl-3,4,5,6-tetrahydro-2H-[1,2']bipyrazinyl-3'-carbonitrile as yellow solid; m.p. 99–101° C.; MS: 308 (M+H)$^+$.

EXAMPLE 76

5'-Ethyl-4-(4-fluoro-phenyl)-6'-methyl-3,4,5,6-tetrahydro-2H-[1,2']bipyrazinyl-3'-carbonitrile and 6'-ethyl-4-(4-fluoro-phenyl)-5'-methyl-3,4,5,6-tetrahydro-2H-[1,2']bipyrazinyl-3'-carbonitrile In analogy to the procedure as described in example 75c, the 1:1 mixture of 3-chloro-6-ethyl-5-methyl-pyrazine-2-carbonitrile and 3-chloro-5-ethyl-6-methyl-pyrazine-2-carbonitrile was reacted with 1-(4-fluorophenyl)piperazine and N-ethyldiisopropylamine in N,N-dimethylformamide at room temperature for 16 hours to give a 1:1 mixture of 5'-ethyl-4-(4-fluoro-phenyl)-6'-methyl-3,4,5,6-tetrahydro-2H-[1,2']bipyrazinyl-3'-carbonitrile and 6'-ethyl-4-(4-fluoro-phenyl)-5'-methyl-3,4,5,6-tetrahydro-2H-[1,2'] bipyrazinyl-3'-carbonitrile as a light yellow oil; MS: 326 (M+H)$^+$.

EXAMPLE 77

6-Ethyl-5-methyl-3-(4-phenyl-piperidin-1-yl)-pyrazine-2-carbonitrile and 5-ethyl-6-methyl-3-(4-phenyl-piperidin-1-yl)-pyrazine-2-carbonitrile In analogy to the procedure as described in example 75c, the 1:1 mixture of the 3-chloro-6-ethyl-5-methyl-pyrazine-2-carbonitrile and the 3-chloro-5-ethyl-6-methyl-pyrazine-2-carbonitrile was reacted with 4-phenylpiperidine and N-ethyldiisopropylamine in N,N-dimethylformamide at room temperature for 16 hours to give a 1:1 mixture of 6-ethyl-5-methyl-3-(4-phenyl-piperidin-1-yl)-pyrazine-2-carbonitrile and 5-ethyl-6-methyl-3-(4-phenyl-piperidin-1-yl)-pyrazine-2-carbonitrile as a light yellow oil; MS: 307 (M+H)$^+$.

EXAMPLE 78

6-Ethyl-5-methyl-3-(4-phenyl-3,6-dihydro-2H-pyridin-1-yl)-pyrazine-2-carbonitrile and 5-ethyl-6-methyl-3-(4-phenyl-3,6-dihydro-2H-pyridin-1-yl)-pyrazine-2-carbonitrile In analogy to the procedure as described in example 75c, the 1:1 mixture of the 3-chloro-6-ethyl-5-methyl-pyrazine-2-carbonitrile and the 3-chloro-5-ethyl-6-methyl-pyrazine-2-carbonitrile was reacted with 1,2,3,6-tetrahydro-4-phenylpiperidine hydrochloride and N-ethyldiisopropylamine in N,N-dimethylformamide at room temperature for 16 hours to give a 1:1 mixture of 6-ethyl-5-methyl-3-(4-phenyl-3,6-dihydro-2H-pyridin-1-yl)-pyrazine-2-carbonitrile and 5-ethyl-6-methyl-3-(4-phenyl-3,6-dihydro-2H-pyridin-1-yl)-pyrazine-2-carbonitrile as a light brown oil; MS: 305 (M+H)$^+$.

EXAMPLE 79

5'-Ethyl-4-(4-fluoro-phenyl)-6methyl-4oxy-3,4,5,6-tetrahydro-2H-[1,2']bipyrazinyl-3'-carbonitrile and 6'-ethyl-4-(4-fluoro-phenyl)-5'-methyl-4'-oxy-3,4,5, 6-tetrahydro-2H-[1,2']bipyrazinyl-3'-carbonitrile a) 3-chloro-6-ethyl-5-methyl-1-oxy-pyrazine-2-carbonitrile and 3-chloro-5-ethyl-6-methyl-1-oxy-pyrazine-2-carbonitrile 0.212 g (2.18 mmol) of hydrogen peroxide (35% solution in water) were slowly added to a solution of 0.193 g (1.06 mmol) of the 1:1 mixture of 3-chloro-6-ethyl-5-methyl-pyrazine-2-carbonitrile and 3-chloro-5-ethyl-6-methyl-pyrazine-2-carbonitrile (example 75b) in 5.0 ml trifluoroacetic acid. The reaction mixture was then stirred at room temperature for 5 hours. It was subsequently poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with a 9:1 to 1:1 v/v gradient of hexane and ethylacetate as the eluent giving 0.178 g (0.09 mmol, 85% of theory) of the 1:1 mixture of 3-chloro-6-ethyl-5-methyl-1-oxy-pyrazine-2-carbonitrile and 3-chloro-5-ethyl-6-methyl-1-oxy-pyrazine-2-carbonitrile as light yellow oil; MS: 197 (M)$^+$.

b) 5'-Ethyl-4-(4-fluoro-phenyl)-6'-methyl-4'-oxy-3,4,5,6-tetrahydro-2H-[1,2']bipyrazinyl-3'-carbonitrile and 6'-ethyl-4-(4-fluoro-phenyl)-5'-methyl-4'-oxy-3,4,5,6-tetrahydro-2H-[1,2']bipyrazinyl-3'-carbonitrile A solution of 0.416 g (2.10 mmol) of the 1:1 mixture of 3-chloro-6-ethyl-5-methyl-1-oxy-pyrazine-2-carbonitrile and 3-chloro-5-ethyl-6-methyl-1-oxy-pyrazine-2-carbonitrile, of 0.465 g (2.53 mmol) of 1-(4-fluorophenyl) piperazine and of 0.833 g (6.31 mmol) of N-ethyldiisopropylamine in 15.0 ml of N,N-dimethylformamide was stirred at room temperature for 18 hours. The reaction mixture was subsequently poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with a 95:5 to 0:100 v/v gradient of hexane and dichloromethane as eluent giving 0.361 g (1.06 mmol, 50.3% of theory) of a mixture of 5'-ethyl-4-(4-fluoro-phenyl)-6'-methyl-4'-oxy-3,4,5,6-tetrahydro-2H-[1,2,'] bipyrazinyl-3'-carbonitrile and 6'-ethyl-4-(4-fluoro-phenyl)-5'-methyl-4'-oxy-3,4,5,6-tetrahydro-2H-[1,2']bipyrazinyl-3'-carbonitrile [1:1], 100 mg of which was further separated by prep. HPLC (Microsorb 80–120–5C Si) using a 99:1 v/v mixture of n-heptane and ethanol as eluent to give 0.030 g of the 5'-ethyl-4-(4-fluoro-phenyl)-6'-methyl-4'-oxy-3,4,5, 6-tetrahydro-2H-[1,2']bipyrazinyl-3'-carbonitrile as a light brown amorphous solid; MS: 342 (M+H)$^+$ and 0.024 g of the 6'-ethyl-4-(4-fluoro-phenyl)-5'-methyl-4'-oxy-3,4,5,6-tetrahydro-2H-[1,2']bipyrazinyl-3'-carbonitrile as a light brown amorphous solid; MS: 342 (M+H)$^+$.

EXAMPLE 80

4-(4-Fluoro-phenyl)-6'-methyl-5'-phenyl-3,4,5,6-tetrahydro-2H-[1,2']bipyrazinyl-3'-carbonitrile In analogy to the procedure described in example 75a–c, 1-phenyl-1,2-propanedione and 2-aminomalonamide were heated in an aqueous solution to give 5-methyl-3-oxo-6-phenyl-3,4-dihydro-pyrazine-2-carboxylic acid amide. Then, the 5-methyl-3-oxo-6-phenyl-3,4-dihydro-pyrazine-2-carboxylic acid amide was treated with triethylamine and phosphorus pentachloride in phosphorus oxychloride at reflux to give 3-chloro-5-methyl-6-phenyl-pyrazine-2-carbonitrile. The 3-chloro-5-methyl-6-phenyl-pyrazine-2-carbonitrile was finally treated with 1-(4-fluorophenyl)piperazine and N-ethyldiiso-propyl-amine in N,N-dimethylformamide at room temperature to yield the 4-(4-fluoro-phenyl)-6'-methyl-5'-phenyl-3,4,5,6-tetrahydro-2H-[1,2']bipyrazinyl-3'-carbonitrile as yellow solid; m.p. 117–120° C.; MS: 374 (M+H)+.

EXAMPLE 81

3-[4-(4-Fluoro-phenyl)-piperidin-1-yl]-5-methyl-6-phenyl-pyrazine-2-carbonitrile In analogy to the procedure described in example 75c, the 3-chloro-5-methyl-6-phenyl-pyrazine-2-carbonitrile was treated with 4-(4-fluoro-phenyl)-piperidine and N-ethyldiisopropylamine in N,N-dimethylformamide at room temperature to yield the 3-[4-(4-fluoro-phenyl)-piperidin-1-yl]-5-methyl-6-phenyl-pyrazine-2-carbonitrile as yellow oil; MS: 373 (M+H)+.

EXAMPLE 82

3-[4-(4-Fluoro-phenyl)-piperidin-1-yl]-5-(2-hydroxy-ethylamino)-pyrazine-2-carbonitrile a) 3-Bromo-5-chloro-pyrazine-2-carbonitrile A solution of 0.309 g (2.00 mmol) of 3-amino-5-chloro-pyrazine-2-carbonitrile (*J. Org. Chem.* 1975, 40, 2341–2347) in 5.0 ml of acetonitrile was slowly added at a temperature of 65° C. to a suspension of 0.903 g (4.0 mmol) of copper(II)bromide and 0.344 g (3.0 mmol) of tert.-butyl nitrite in 20.0 ml of acetonitrile. The reaction mixture was stirred at 65° C. for 1 hour, then cooled to room temperature. It was subsequently poured into 50 ml of an ice/water mixture and extracted 3 times with 50 ml of dichloromethane. The combined dichloromethane phases were dried over magnesium sulfate and evaporated under reduced pressure. The residue formed was chromatographed on silica gel with a 4:1 to 0:10 v/v gradient of hexane and dichloromethane as the eluent giving 0.333 g (1.53 mmol, 76.2% of theory) of the 3-bromo-5-chloro-pyrazine-2-carbonitrile as light yellow solid; m.p. 66–67° C.; MS: 218 (M)+.

b) 3-Bromo-5-(2-hydroxy-ethylamino)-pyrazine-2-carbonitrile 0.061 g (1.00 mmol) of ethanolamine were added slowly at room temperature to a solution of 0.218 g (1.0 mmol) of the 3-bromo-5-chloro-pyrazine-2-carbonitrile and 0.264 g (2.0 mmol) of N-ethyldiisopropylamine in 15.0 ml of dioxane. The reaction mixture was stirred at room temperature for 18 hours. It was subsequently poured into 50 ml of an ice/water/sodium hydrogen carbonate mixture and extracted 3 times with 50 ml of ethylacetate. The combined ethylacetate phases were dried over magnesium sulfate and evaporated under reduced pressure. The residue formed was chromatographed on silica gel with a 100:0 to 95:5 v/v gradient of dichloromethane and methanol as the eluent giving 0.131 g (0.539 mmol, 53.9% of theory) of the 3-bromo-5-(2-hydroxy-ethylamino)-pyrazine-2-carbonitrile as yellow solid; m.p. 158–160° C.; MS: 243 (M)+.

c) 3-[4-(4-Fluoro-phenyl)-piperidin-1-yl]-5-(2-hydroxy-ethylamino)-pyrazine-2-carbonitrile 0.415 g (3.00 mmol) of potassium carbonate were added slowly at room temperature to a solution of 0.243 g (1.0 mmol) of the 3-bromo-5-(2-hydroxy-ethylamino)-pyrazine-2-carbonitrile and 0.324 g (1.5 mmol) of the 4-(4-fluoro-phenyl)-piperidine hydrochloride in 15.0 ml of N,N-dimethylformamide. The reaction mixture was stirred at room temperature for 64 hours and at 80° C. for 5 hours. It was subsequently poured into 50 ml of an ice/water mixture and extracted 3 times with 50 ml of dichloromethane. The combined dichloromethane phases were dried over magnesium sulfate and evaporated under reduced pressure. The residue formed was recrystallized from hexane/ethylacetate giving 0.314 g (0.92 mmol, 92% of theory) of the 3-[4-(4-fluoro-phenyl)-piperidin-1-yl]-5-(2-hydroxy-ethylamino)-pyrazine-2-carbonitrile as yellow solid; m.p. 155–158° C.; MS: 342 (M+H)[30].

EXAMPLE 83

4-(4-Fluoro-phenyl)-6'-(2-hydroxy-ethylamino)-3,4,5,6-tetrahydro-2H-[1,2']bipyrazinyl-3'-carbonitrile In analogy to the procedure described in example 82c, 3-bromo-5-(2-hydroxy-ethyl-amino)-pyrazine-2-carbonitrile was treated with 1-(4-fluorophenyl)piperazine in the presence of potassium carbonate in N,N-dimethylformamide between room temperature and 80° C. to yield 4-(4-fluoro-phenyl)-6'-(2-hydroxy-ethylamino)-3,4,5,6-tetrahydro-2H-[1,2']bipyrazinyl-3'-carbonitrile as light yellow solid; m.p. 149–151° C.; MS: 343 (M+H)+.

EXAMPLE 84

3-(2-Hydroxy-ethylamino)-5-(4-phenyl-3,6-dihydro-2H-pyridin-1-yl)-[1,2,4]triazine-6-carbonitrile a) 5-chloro-3-methylsulfanyl-[1,2,4]triazine-6-carbonitrile A solution of 500 mg (2.7 mmol) of 3-methylsulfanyl-5-oxo-4,5-dihydro-[1,2,4]triazine-6-carboxylic acid amide (J. J. Huang, *J. Org. Chem.* 1985, 50, 2293–2298; H. Wang et al., *Hua Hsueh Hsueh Pao* 1964, 30 (2), 183–192; CA Vol. 61, 8311b) in 38 ml (408 mmol) of phosphorus oxychloride was heated to reflux during 1.5 h. After cooling the dark brown reaction mixture, the excess of phosphorus oxychloride was evaporated under reduced pressure. To destroy residues of phosphorus oxychloride and to neutralize the reaction mixture, the resulting red-brown oily residue was dissolved in 15 ml of toluene and the solution added to an ice-cold saturated aqueous solution of sodium hydrogencarbonate. The organic phase was diluted with 100 ml of dichloromethane, separated from the aqueous phase, dried over sodium sulfate, and evaporated under reduced pressure. The resulting 5-chloro-3-methylsulfanyl-[1,2,4]triazine-6-carbonitrile was obtained as a brown oil and was used in the following reactions without further purification.

b) 3-Methylsulfanyl-5-(4-phenyl-3,6-dihydro-2H-pyridin-1-yl)-[1,2,4]triazine-6-carbonitrile A solution of 130 mg (0.66 mmol) of 4-phenyl-1,2,3,6-tetrahydropyridine hydrochloride in 5 ml of dioxane was treated at room temperature with 0.23 ml (1.32 mmol) of N-ethyl-diisopropylamine and, thereupon, with 112 mg (0.60 mmol) of crude 5-chloro-3-methylsulfanyl-[1,2,4]triazine-6-carbonitrile. The reaction mixture was stirred at 50° C. during 18 hours. For the working-up, the solution was evaporated under reduced pressure and the residue was chromatographed on silica gel with a 2:1 mixture of hexane and ethylacetate as the eluent. There were obtained 120 mg (0.34 mmol, 64.5% of theory) of 3-methylsulfanyl-5-(4-phenyl-3,6-dihydro-2H-pyridin-1-yl)-[1,2,4]triazine-6-carbonitrile in the form of an orange powder; MS: [M+H]+= 310.

c) 3-(2-Hydroxy-ethylamino)-5-(4-phenyl-3,6-dihydro-2H-pyridin-1-yl)-[1,2,4]triazine carbonitrile A mixture of 68 mg (0.21 mmol) of 3-methylsulfanyl-5-(4-phenyl-3,6-dihydro-2H-pyridin-1-yl)-[1,2,4]triazine-6-carbonitrile and 14.5 mg (0.23 mmol) ethanolamine in 1 ml of dioxane was stirred at 120° C. overnight. For the working-up, the solution was evaporated under reduced pressure and the residue was chromatographed on silica gel with a 90:10:0.1 mixture of dichloromethane, methanol, and ammonium hydroxide as the eluent. There were obtained 35 mg (0.10 mmol, 50% of theory) of 3-(2-hydroxy-ethylamino)-5-(4-phenyl-3,6-dihydro-2H-pyridin-1-yl)-[1,2,4]triazine-6-carbonitrile as an amorphous, white solid; MS: 323 (M+H)$^+$;

EXAMPLE 85

3-(2-Hydroxy-ethylamino)-5-(4-phenyl-piperazin-1-yl)-[1,2,4]triazine-6-carbonitrile a) 3-Methylsulfanyl-5-(4-phenyl-piperazin-1-yl)-[1,2,4]triazine-6-carbonitrile In analogy to the procedure described in example 84b, the crude 5-chloro-3-methyl-sulfanyl-[1,2,4]triazine-6-carbonitrile (see example 84a) was treated with 1-phenyl-piperazine in ethanol in the presence of N-ethyl-diisopropylamine at room temperature during 3 days to yield 3-methylsulfanyl-5-(4-phenyl-piperazin-1-yl)-[1,2,4]triazine-6-carbonitrile as a white solid; MS: [M+H]$^+$=313.

b) 3-(2-Hydroxy-ethylamino)-5-(4-phenyl-piperazin-1-yl)-[1,2,4]triazine-6-carbonitrile In analogy to the procedure described in example 84c, 3-methylsulfanyl-5-(4-phenyl-piperazin-1-yl)-[1,2,4]triazine-6-carbonitrile was treated with ethanolamine in a sealed tube at 140° C. during 18 hours to yield 3-(2-hydroxy-ethylamino)-5-(4-phenyl-piperazin-1-yl)-[1,2,4]triazine-6-carbonitrile as an amorphous, white solid; MS: [M+H]$^+$=326.

EXAMPLE 86

{2-[6-cyano-5-(4-phenyl-piperazin-1-yl)-[1,2,4]triazin-3-ylamino]-ethyl}-carbamic acid tert-butyl ester In analogy to the procedure described in example 84c, 3-methylsulfanyl-5-(4-phenyl-piperazin-1-yl)-[1,2,4]triazine-6-carbonitrile was treated with N-Boc-ethylene-diamine in a sealed tube at 130° C. during 48 hours to yield {2-[6-cyano-5-(4-phenyl-piperazin-1-yl)-[1,2,4]triazin-3-ylamino]-ethyl}-carbamic acid tert-butyl ester as an amorphous, light yellow solid; MS: [M+H]$^+$=425.

Example A

Tablets of the following composition are produced in a conventional manner:

|  | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

Example B

Tablets of the following composition are produced in a conventional manner:

|  | mg/Tablet |
|---|---|
| Active ingredient | 200 |
| Powdered lactose | 100 |
| White corn starch | 64 |
| Polyvinylpyrrolidone | 12 |
| Na carboxymethylstarch | 20 |
| Magnesium stearate | 4 |
| Tablet weight | 400 |

Example C

Capsules of the following composition are produced:

|  | mg/Capsule |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound of the formula

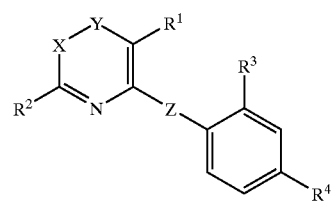

I or a pharmaceutically acceptable salt thereof, wherein $R^1$ is selected from the group consisting of nitro and cyano;

$R^2$ is selected from the group consisting of hydrogen, ($C_1$–$C_7$)-alkyl and —NHR$^{10}$; wherein $R^{10}$ is selected from the group consisting of hydrogen, ($C_1$–$C_7$)-alkyl, —(CH$_2$)$_m$—OR$^{11}$, —(CH$_2$)$_p$—($C_3$–$C_6$)-cycloalkyl, —(CH$_2$)$_m$—NH—C(O)O—($C_1$–$C_7$)-alkyl and —(CH$_2$)$_p$-pyridyl; wherein $R^{11}$ is selected from the group consisting of hydrogen and (($C_1$–$C_7$)-alkyl;

$R^3$ is selected from the group consisting of hydrogen, ($C_1$–$C_7$)-alkyl, fluoro, hydroxy, ($C_1$–$C_7$)-alkoxy, ($C_1$–$C_7$)-alkylthio, cyano and nitro;

$R^4$ is selected from the group consisting of hydrogen and fluoro;

is selected from the group consisting of

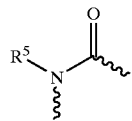
(a)

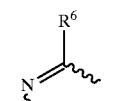
(b)

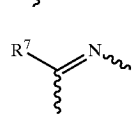
(c)

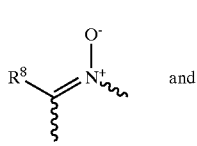
(d)

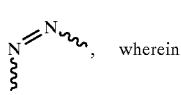, wherein
(e)

$R^5$ is selected from the group consisting of hydrogen, $(C_1-C_7)$-alkyl, $(C_1-C_7)$-alkenyl, $-(CH_2)_m-OR^{11}$, fluoro-$(C_1-C_7)$-alkyl and $-(CH_2)_n-CN$;

$R^6$ is selected from the group consisting of $(C_1-C_7)$-alkyl, halogen, hydroxy, $(C_1-C_7)$-alkoxy, $(C_1-C_7)$-alkylthio, $-O-(CH_2)_m OR^{11}$, $-O$-fluoro-$(C_1-C_7)$-alkyl and $-NHR^{12}$; and $R^{12}$ is selected from the group consisting of $(C_1-C_7)$-alkyl, $-(CH_2)_m-OR^{11}$, $-(CH_2)_p-(C_3-C_6)$-cycloalkyl and $-(CH_2)_p$-pyridyl;

$R^7$ is selected from the group consisting of hydrogen, $(C_1-C_7)$-alkyl and phenyl;

$R^8$ is selected from the group consisting of hydrogen, $(C_1-C_7)$-alkyl and phenyl;

Z is selected from the group consisting of

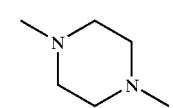
(i)

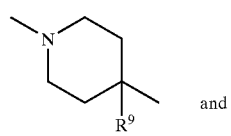
(ii)

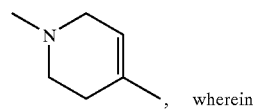, wherein
(iii)

$R^9$ is selected from the group consisting of hydrogen, hydroxy and cyano;

m is independently from each other in each occurrence 2, 3, 4, 5 or 6;

n is independently from each other in each occurrence 1, 2, 3, 4, 5 or 6; and p is independently from each other in each occurrence 0, 1, 2, 3, 4, 5 or 6.

2. A compound in accordance with claim 1 of the formula

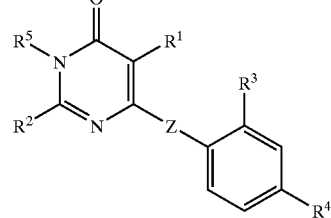
Ia wherein $R^1$ to $R^5$ and Z are as defined in claim 1, or a pharmaceutically acceptable salt thereof.

3. A compound of formula 1a in accordance with claim 2, of the formula

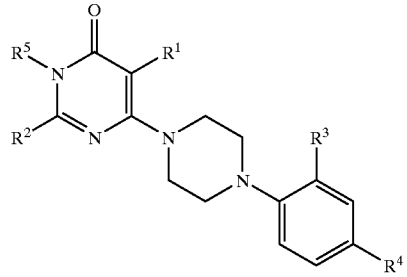
Ia1 wherein $R^2$ is lower alkyl and $R^5$ is selected from the group consisting of $(C_1-C_7)$-alkyl, $(C_1-C_7)$-alkyl substituted by halo and $(C_1-C_7)$-alkyl substituted by hydroxyl.

4. The compound of claim 3 wherein the compound is selected from the group consisting of 6-[4-(4-Fluoro-phenyl)-piperazin-1-yl]-2-methyl-5-nitro-3-(2,2,2-trifluoro-ethyl)-3H-pyrimidin-4-one;

3-ethyl-6-[4-(4-fluoro-phenyl)-piperazin-1-yl]-2-methyl-5-nitro-3H-pyrimidin-4-one; and 6-[4-(4-fluoro-phenyl)-piperazin-1-yl]-3-(2-hydroxy-ethyl)-2-methyl-5-nitro-3H-pyrimidin-4-one.

5. A compound of formula Ia in accordance with claim 2, of the formula

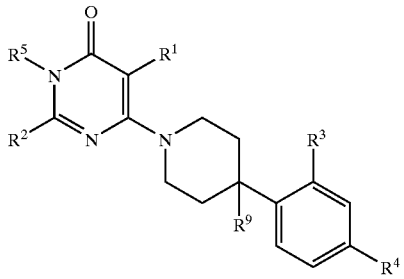

Ia2 wherein $R^2$ is selected from the group consisting of $(C_1-C_7)$-alkyl and $-NHR^{10}$, $R^{10}$ is selected from the group consisting of $(C_1-C_7)$-alkyl, $-(CH_2)_m-OR^{11}$, $-(CH_2)_p-(C_3-C_6)$-cycloalkyl, and $R^{11}$ is selected from the group consisting of hydrogen and $(C_1-C_7)$-alkyl, $-(CH_2)_m-NH-C(O)O-(C_1-C_7)$-alkyl and $-(CH_2)_p$-pyridyl;

$R^3$ is selected from the group consisting of hydrogen and fluoro; and wherein $R^9$ is hydrogen.

6. A compound of formula Ia2 in accordance with claim 5, wherein $R^3$ is hydrogen and $R^5$ is selected from the group consisting of-$(C_1-C_7)$-alkyl, $-(CH_2)_m-OR^{11}$ and fluoro-$(C_1-C_7)$-alkyl.

7. A compound of formula Ia2 in accordance with claim 6, wherein the compound is selected from the group consisting of 6-[4-(4-fluoro-phenyl)-piperidin-1-yl]-2-methyl-5-nitro-3-(2,2,2-trifluoro-ethyl) pyrimidin-4-one, 2-methyl-5-nitro-6-(4-phenyl-piperidin-1-yl)-3-(2,2,2-trifluoro-ethyl)-3H-pyrimidin-4-one, and 6-[4-(4-fluoro-phenyl)-piperidin-1-yl]-3-(2-methoxy-ethyl)-2-methyl-5-nitro-3H-pyrimidin-4-one.

8. A compound in accordance with claim 1 of the formula

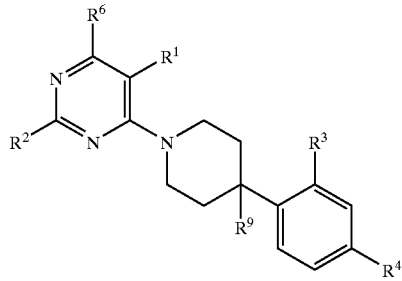

Ib or a pharmaceutically acceptable salt thereof.

9. A compound in accordance with claim 8 of the formula

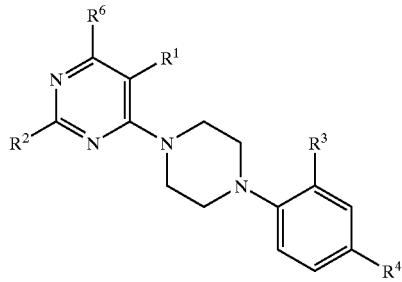

Ib1 wherein $R^2$ is selected from the group consisting of $(C_1-C_7)$-alkyl and $-NHR^{10}$; and $R^{10}$ is selected from the group consisting of $(C_1-C_7)$-alkyl, $-(CH_2)_m-OR^{11}$, $-(CH_2)_p-(C_3-C_6)$-cycloalkyl; and $R^{11}$ is selected from the group consisting of hydrogen and $(C_1-C_7)$-alkyl, $-(CH_2)_m-NH-C(O)O-(C_1-C_7)$-alkyl and $-(CH_2)_p$-pyridyl;

$R^3$ is selected from the group consisting of hydrogen and fluoro;

$R^6$ is selected from the group consisting of halogen, $(C_1-C_7)$-alkoxy, $(C_1-C_7)$-alkylthio, $-O-(CH_2)_m-OR^{11}$, $-O$-fluoro-$(C_1-C_7)$-alkyl and $-NHR^{12}$, and $R^{12}$ is selected from the group consisting of $(C_1-C_7)$-alkyl, $-(CH_2)_m-OR$ and $-(CH_2)_p-(C_3-C_6)$-cycloalkyl.

10. A compound of formula Ib1 in accordance with claim 9, wherein the compound is selected from the group consisting of 2-(cyclopropylmethyl-amino)-4-[4-(4-fluoro-phenyl)-piperazin-1-yl]-6-(2-hydroxy-ethylamino)-pyrimidine-5-carbonitrile, 2-(cyclopropylmethyl-amino)-4-(2-hydroxy-ethylamino)-6-(4-phenyl-piperazin-1-yl)-pyrimidine-5-carbonitrile, 2-cyclopropylamino-4-[4-(4-fluoro-phenyl)-piperazin-1-yl]-6-(2-hydroxy-ethylamino)-pyrimidine-5-carbonitrile, 2-cyclopropylamino-4-(2-hydroxy-ethylamino)-6-(4-phenyl-piperazin-1-yl)-pyrimidine-5-carbonitrile, 2-{6-[4-(4-fluoro-phenyl)-piperazin-1-yl]-2-methyl-5-nitro-pyrimidin-4-yloxy}-ethanol and 2,4-bis-cyclopropylamino-6-(4-phenyl-piperazin-1-yl)-pyrimidine-5-carbonitrile.

11. A compound in accordance with claim 8 of the formula

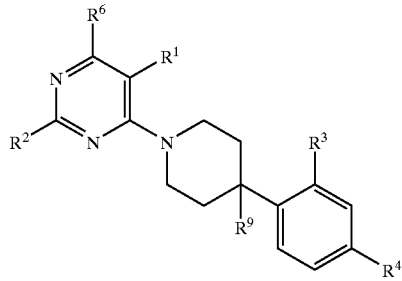

Ib2 wherein

R² is selected from the group consisting of (C₁–C₇)-alkyl and —NHR¹⁰; and

R¹⁰ is selected from the group consisting of (C₁–C₇)-alkyl, —(CH₂)ₘ—OR¹¹, —(CH₂)ₚ—(C₃–C₆)-cycloalkyl, and R¹¹ is selected from the group consisting of hydrogen and (C₁–C₇)-alkyl, —(CH₂)ₘ—NH—C(O)O—(C₁–C₇)-alkyl and —(CH₂)ₚ-pyridyl;

R³ is selected from the group consisting of hydrogen and fluoro;

R⁶ is selected from the group consisting of halogen, (C₁–C₇)-alkoxy, (C₁–C₇)-alkylthio, —O—(CH₂)ₘ—OR¹¹, —O-fluoro-(C₁–C₇)-alkyl and —NHR¹²;

R⁹ is hydrogen; and

R¹² is selected from the group consisting of (C₁–C₇)-alkyl, —(CH₂)ₘ—OR and —(CH₂)ₚ—(C₃–C₆)-cycloalkyl.

12. A compound of formula Ib2 in accordance with claim 11, selected from the group consisting of 2-(cyclopropylmethyl-amino)-4-(2-hydroxy-ethylamino)-6-(4-phenyl-piperidin-1-yl)-pyrimidine-5-carbonitrile, 4-(4-phenyl-piperidin-1-yl)-2-[(pyridin-3-ylmethyl)-amino]-6-(2,2,2-trifluoro-ethoxy)-pyrimidine-5-carbonitrile, 4-[4-(4-fluoro-phenyl)-piperidin-1-yl]-2-[(pyridin-3-ylmethyl)-amino]-6-(2,2,2-trifluoro-ethoxy)-pyrimidine-5-carbonitrile, 2-cyclopropylamino-4-(2-hydroxy-ethylamino)-6-(4-phenyl-piperidin-1-yl)-pyrimidine-5-carbonitrile, 4-[4-(4-fluoro-phenyl)-piperidin-1-yl]-2-(2-hydroxy-ethylamino)-6-(2,2,2-trifluoro-ethoxy)-pyrimidine-5-carbonitrile, 2-(cyclopropylmethyl-amino)-4-[4-(4-fluoro-phenyl)-piperidin-1-yl]-6-(2-hydroxy-ethylamino)-pyrimidine-5-carbonitrile, 4-(2-hydroxy-ethylamino)-6-(4-phenyl-piperidin-1-yl)-2-[(pyridin-3-ylmethyl)-amino]-pyrimidine-5-carbonitrile, 2-(2-hydroxy-ethylamino)-4-(4-phenyl-piperidin-1-yl)-6-(2,2,2-trifluoro-ethoxy)-pyrimidine-5-carbonitrile and 4-chloro-2-(2-hydroxy-ethylamino)-6-(4-phenyl-piperidin-1-yl)-pyrimidine-5-carbonitrile.

13. A compound in accordance with claim 1 of the formula

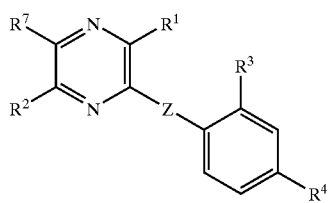

Ic or a pharmaceutically acceptable salt thereof.

14. A compound in accordance with claim 13 of the formula

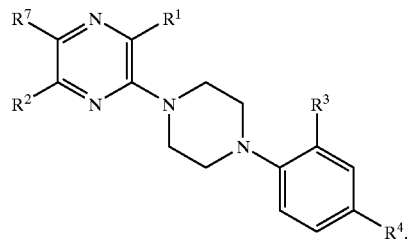

Ic1

15. A compound of formula Ic1 in accordance with claim 14, wherein

R² is selected from the group consisting of (C₁–C₇)-alkyl and —NHR¹⁰; wherein

R¹⁰ is selected from the group consisting of (C₁–C₇)-alkyl, —(CH₂)ₘ—OR¹¹, —(CH₂)ₚ—(C₃–C₆)-cycloalkyl; and R¹¹ is selected from the group consisting of hydrogen and (C₁–C₇)-alkyl;

R³ is selected from the group consisting of hydrogen and fluoro; and

R⁷ is selected from the group consisting of (C₁–C₇)-alkyl and phenyl.

16. A compound of formula Ic1 in accordance with claim 15, wherein R² is (C₁–C₇)-alkyl and R³ is hydrogen.

17. A compound of formula Ic1 in accordance with claim 16, selected from the group consisting of 4-(4-fluoro-phenyl)-6'-methyl-5'-phenyl-3,4,5,6-tetrahydro-2H-[1,2']bipyrazinyl-3'-carbonitrile, 5'-ethyl-4-(4-fluoro-phenyl)-6'-methyl-3,4,5,6-tetrahydro-2H-[1,2']bipyrazinyl-3'-carbonitrile, 6'-ethyl-4-(4-fluoro-phenyl)-5'-methyl-3,4,5,6-tetrahydro-2H-[1,2']bipyrazinyl-3'-carbonitrile, 5'-ethyl-6'-methyl-4-phenyl-3,4,5,6-tetrahydro-2H-[1,2']bipyrazinyl-3'-carbonitrile and 6'-ethyl-5'-methyl-4-phenyl-3,4,5,6-tetrahydro-2H-[1,2']bipyrazinyl-3'-carbonitrile.

18. A compound in accordance with claim 13 of the formula

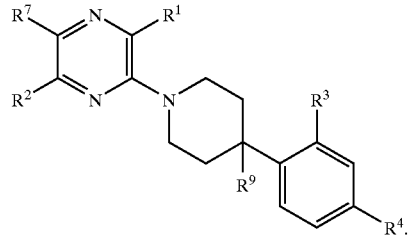

Ic2

19. A compound of formula Ic2 in accordance with claim 18, wherein

R² is selected from the group consisting of (C₁–C₇)-alkyl and —NHR¹⁰; wherein

R¹⁰ is selected from the group consisting of (C₁–C₇)-alkyl, —(CH₂)ₘ—OR¹¹, —(CH₂)ₚ—(C₃–C₆)-cycloalkyl, and R¹¹ is selected from the group consisting of hydrogen and (C₁–C₇)-alkyl;

R³ is selected from the group consisting of hydrogen and fluoro; and

R⁷ is selected from the group consisting of (C₁–C₇)-alkyl and phenyl.

20. A compound of formula Ic2 in accordance with claim 19, wherein $R^2$ is $(C_1-C_7)$-alkyl, $R^9$ is hydrogen and $R^3$ is hydrogen.

21. A compound of formula Ic2 in accordance with claim 20 wherein the compound is selected from the group consisting of 6-ethyl-5-methyl-3-(4-phenyl-piperidin-1-yl)-pyrazine-2-carbonitrile and 5-ethyl-6-methyl-3-(4-phenyl-piperidin-1-yl)-pyrazine-2-carbonitrile.

22. A compound of formula Ic in accordance with claim 13 of the formula

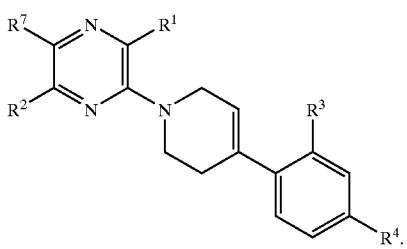

Ic3

23. A compound of formula Ic3 in accordance with claim 22 wherein $R^2$ is selected from the group consisting of $(C_1-C_7)$-alkyl and $-NHR^{10}$, $R^{10}$ is selected from the group consisting of $(C_1-C_7)$-alkyl, $-(CH_2)_m-OR^{11}$, $-(CH_2)_p-(C_3-C_6)$-cycloalkyl, and $R^{11}$ is selected from the group consisting of hydrogen and $(C_1-C_7)$-alkyl;

$R^3$ is selected from the group consisting of hydrogen and fluoro; and $R^7$ is selected from the group consisting of $(C_1-C_7)$-alkyl and phenyl.

24. A compound of formula Ic3 in accordance with claim 23, wherein $R^2$ is $(C_1-C_7)$-alkyl and $R^3$ is hydrogen.

25. A compound of formula Ic3 in accordance with claim 24 wherein the compound is selected from the group consisting of 6-ethyl-5-methyl-3-(4-phenyl-3,6-dihydro-2H-pyridin-1-yl)-pyrazine-2-carbonitrile and 5-ethyl-6-methyl-3-(4-phenyl-3,6-dihydro-2H-pyridin-1-yl)-pyrazine-2-carbonitrile.

26. A compound in accordance with claim 1 of the formula

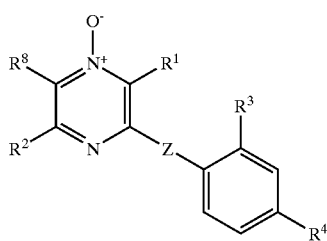

Id or a pharmaceutically acceptable salt thereof.

27. A compound in accordance with claim 26 of the formula

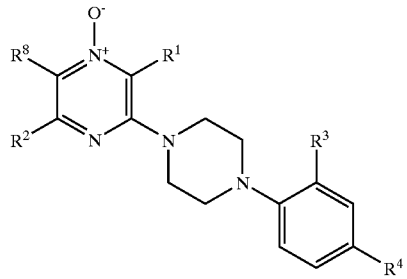

Id1 wherein
$R^2$ is $(C_1-C_7)$-alkyl;
$R^3$ is selected from the group consisting of hydrogen and fluoro; and
$R^8$ is $(C_1-C_7)$-alkyl.

28. A compound of formula Id1 in accordance with claim 27, selected from the group consisting of 5'-ethyl-4-(4-fluoro-phenyl)-6'-methyl-4'-oxy-3,4,5,6-tetrahydro-2H-[1,2']bipyrazinyl-3'-carbonitrile and 6'-ethyl-4-(4-fluoro-phenyl)-5'-methyl-4'-oxy-3,4,5,6-tetrahydro-2H-[1,2']bipyrazinyl-3'-carbonitrile.

29. A compound in accordance with claim 1 of the formula

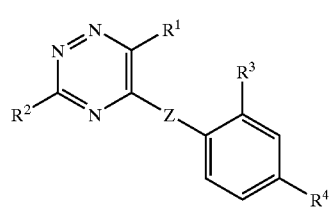

Ie or a pharmaceutically acceptable salt thereof.

30. A compound in accordance with claim 29, of the formula

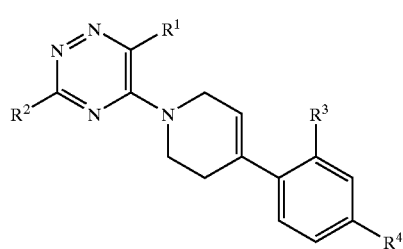

Ie1 wherein
$R^2$ is $-NHR^{10}$,
$R^{10}$ is selected from the group consisting of $(C_1-C_7)$-alkyl, $-(CH_2)_m-OR^{11}$, $-(CH_2)_p-(C_3-C_6)$-cycloalkyl, and
$R^{11}$ is selected from the group consisting of hydrogen and $(C_1-C_7)$-alkyl; and
$R^3$ is hydrogen.

31. A compound of formula Ie1 in accordance with claim 30, 3-(2-hydroxy-ethylamino)-5-(4-phenyl-3,6-dihydro-2H-pyridin-1-yl)-[1,2,4]triazine-6-carbonitrile.

32. A pharmaceutical composition comprising a therapeutically effective amount of a compound of formula I according to claim 1 or a pharmaceutically acceptable salt thereof and at least one pharmaceutically acceptable excipient.

33. A process for the manufacture of a compound of formula comprising reacting a compound of formula

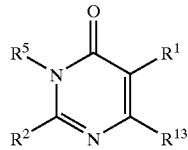
IIa wherein $R^{13}$ is halogen, with a compound of formula

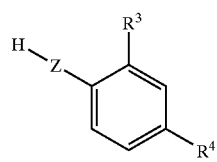
III forming a compound of formula

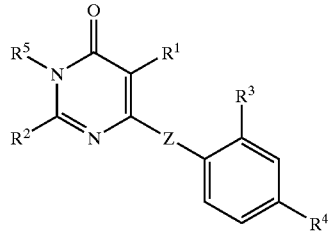
Ia wherein

- $R^1$ is selected from the group consisting of nitro and cyano;
- $R^2$ is selected from the group consisting of hydrogen, $(C_1-C_7)$-alkyl and —$NHR^{10}$; wherein
  - $R^{10}$ is selected from the group consisting of hydrogen, $(C_1-C_7)$-alkyl, —$(CH_2)_m$—$OR^{11}$, —$(CH_2)_p$—$(C_3-C_6)$-cycloalkyl, —$(CH_2)_m$—NH—C(O)O—$(C_1-C_7)$-alkyl and —$(CH_2)_p$-pyridyl; wherein
    - $R^{11}$ is selected from the group consisting of hydrogen and $(C_1-C_7)$-alkyl;
- $R^3$ is selected from the group consisting of hydrogen, $(C_1-C_7)$-alkyl, fluoro, hydroxy, $(C_1-C_7)$-alkoxy, $(C_1-C_7)$-alkylthio, cyano and nitro;
- $R^4$ is selected from the group consisting of hydrogen and fluoro;

is selected from the group consisting of

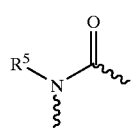
(a)

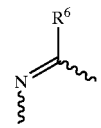
(b)

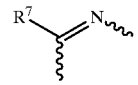
(c)

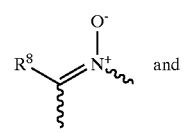
(d)

and

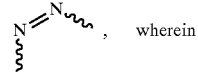
(e)

, wherein $R^5$ is selected from the group consisting of hydrogen, $(C_1-C_7)$-alkyl, $(C_1-C_7)$-alkenyl, —$(CH_2)_m$—$OR^{11}$, fluoro-$(C_1-C_7)$-alkyl and —$(CH_2)_n$—CN; and Z is selected from the group consisting of

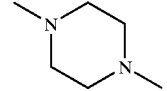
(i)

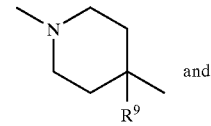
(ii)

and

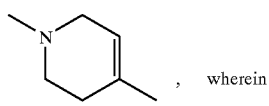
(iii)

, wherein $R^9$ is selected from the group consisting of hydrogen, hydroxy and cyano.

34. A process for the manufacture of a compound of formula I or a pharmaceutically acceptable salt thereof, comprising reacting a compound of formula

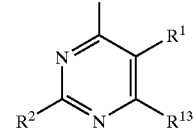
IIb wherein $R^6$ and $R^{13}$ are halogen, with a compound of formula

III

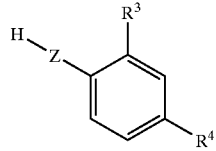

and, substituting the halogen of $R^6$ with the resepctive nucleophiles to obtain a compound of formula Ib

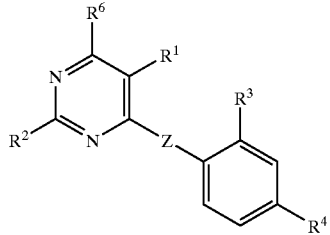

wherein $R^1$ is selected from the group consisting of nitro and cyano;

$R^2$ is selected from the group consisting of hydrogen, $(C_1-C_7)$-alkyl and —$NHR^{10}$; wherein
  $R^{10}$ is selected from the group consisting of hydrogen, $(C_1-C_7)$-alkyl, —$(CH_2)_m$—$OR^{11}$, —$(CH_2)_p$—$(C_3-C_6)$-cycloalkyl, —$(CH_2)_m$—NH—C(O)O—$(C_1-C_7)$-alkyl and —$(CH_2)_p$-pyridyl; wherein
    $R^{11}$ is selected from the group consisting of hydrogen and $(C_1-C_7)$-alkyl;

$R^3$ is selected from the group consisting of hydrogen, $(C_1-C_7)$-alkyl, fluoro, hydroxy, $(C_1-C_7)$-alkoxy, $(C_1-C_7)$-alkylthio, cyano and nitro;

$R^4$ is selected from the group consisting of hydrogen and fluoro;

is selected from the group consisting of (a)

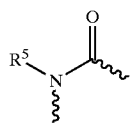

(b)

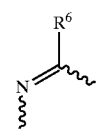

(c)

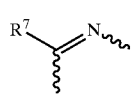

(d)

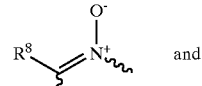

and (e)

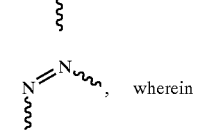

, wherein $R^5$ is selected from the group consisting of hydrogen, $(C_1-C_7)$-alkyl, $(C_1-C_7)$-alkenyl, —$(CH_2)_m$—$OR^{11}$, fluoro-$(C_1-C_7)$-alkyl and —$(CH_2)_n$—CN;

$R^6$ is selected from the group consisting of $(C_1-C_7)$-alkyl, halogen, hydroxy, $(C_1-C_7)$-alkoxy, $(C_1-C_7)$-alkylthio, —O—$(CH_2)_m$—$OR^{11}$, —O-fluoro-$(C_1-C_7)$-alkyl and —$NHR^{12}$; and $R^{12}$ is selected from the group consisting of $(C_1-C_7)$-alkyl, —$(CH_2)_m$—$OR^{11}$, —$(CH_2)_p$—$(C_3-C_6)$-cycloalkyl and —$(CH_2)_p$-pyridyl;

and Z is as defined in claim 1, and converting a compound of formula Ib into a pharmaceutically acceptable salt.

35. A process for the manufacture of a compound of formula I or a pharmaceutically acceptable salts thereof, comprising reacting a compound of formula IIc

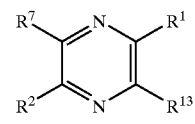

wherein $R^{13}$ is halogen, with a compound of formula

III

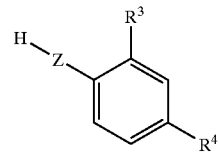

to obtain a compound of formula

Ic

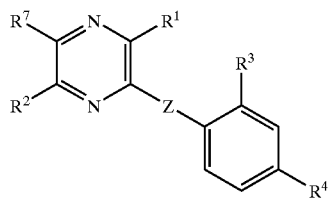

wherein $R^1$ is selected from the group consisting of nitro and cyano;

$R^2$ is selected from the group consisting of hydrogen, $(C_1-C_7)$-alkyl and —$NHR^{10}$; wherein
  $R^{10}$ is selected from the group consisting of hydrogen, $(C_1-C_7)$-alkyl, —$(CH_2)_m$—$OR^{11}$, —$(CH_2)_p$—$(C_3-C_6)$-cycloalkyl, —$(CH_2)_m$—NH—C(O)O—$(C_1-C_7)$-alkyl
  and —$(CH_2)_p$-pyridyl; wherein $R^{11}$ is selected from the group consisting of hydrogen and $(C_1-C_7)$-alkyl;

$R^3$ is selected from the group consisting of hydrogen, $(C_1-C_7)$-alkyl, fluoro, hydroxy, $(C_1-C_7)$-alkoxy, $(C_1-C_7)$-alkylthio, cyano and nitro;

$R^4$ is selected from the group consisting of hydrogen and fluoro;

is selected from the group consisting of

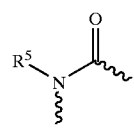
(a)

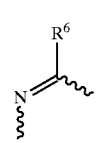
(b)

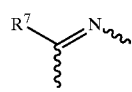
(c)

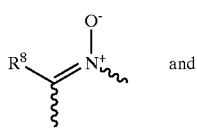
and (d)

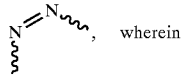
, wherein (e)

$R^7$ is selected from the group consisting of hydrogen, $(C_1-C_7)$-alkyl and phenyl; and Z is selected from the group consisting of

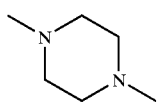
(i)

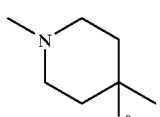
and (ii)

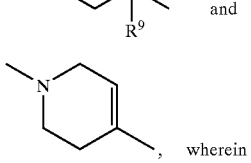
, wherein (iii)

$R^9$ is selected from the group consisting of hydrogen, hydroxy and cyano.

36. A process for the manufacture of a compound of formula I or a pharmaceutically acceptable salts thereof, comprising reacting a compound of formula

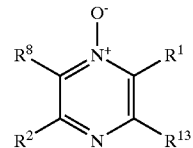
IId wherein $R^{13}$ is halogen, with a compound of formula

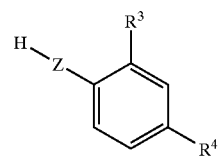
III to obtain a compound of formula

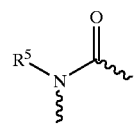
Id wherein $R^1$ is selected from the group consisting of nitro and cyano;

$R^2$ is selected from the group consisting of hydrogen, $(C_1-C_7)$-alkyl and $-NHR^{10}$; wherein $R^{10}$ is selected from the group consisting of hydrogen, $(C_1-C_7)$-alkyl, $-(CH_2)_m-OR^{11}$, $-(CH_2)_p-(C_3-C_6)$-cycloalkyl, $-(CH_2)_m-NH-C(O)O-(C_1-C_7)$-alkyl and $-(CH_2)_p$-pyridyl; wherein $R^{11}$ is selected from the group consisting of hydrogen and $(C_1-C_7)$-alkyl;

$R^3$ is selected from the group consisting of hydrogen, $(C_1-C_7)$-alkyl, fluoro, hydroxy, $(C_1-C_7)$-alkoxy, $(C_1-C_7)$-alkylthio, cyano and nitro;

$R^4$ is selected from the group consisting of hydrogen and fluoro;

is selected from the group consisting of

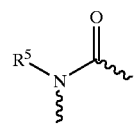
(a)

-continued (b)
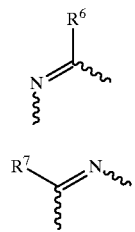

(c)
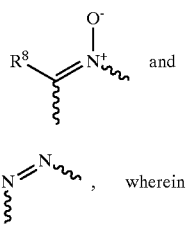

(d)
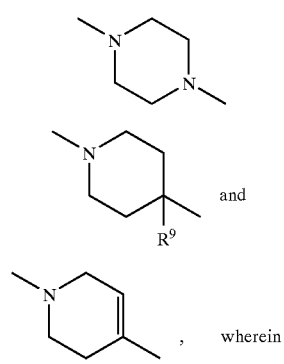
and (e)
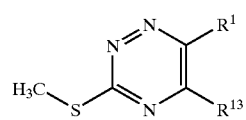, wherein $R^8$ is selected from the group consisting of hydrogen, $(C_1-C_7)$-alkyl and phenyl; and Z is selected from the group consisting of (i)
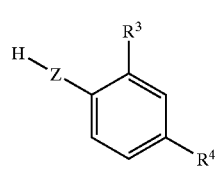

(ii)

(iii)

, wherein $R^9$ is selected from the group consisting of hydrogen, hydroxy and cyano.

37. A process for the manufacture of a compound of formula I or a pharmaceutically acceptable salts thereof, comprising reacting a compound of formula IIe wherein $R^{13}$ is halogen, with a compound of formula

III and substituting the thiomethyl group with the respective nucleophiles to obtain a compound of formula Ie-1
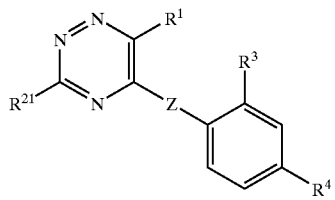

wherein $R^{21}$ is —$NHR^{10}$ and $R^1$ is selected from the group consisting of nitro and cyano;

$R^3$ is selected from the group consisting of hydrogen, $(C_1-C_7)$-alkyl, fluoro, hydroxy, $(C_1-C_7)$-alkoxy, $(C_1-C_7)$-alkylthio, cyano and nitro;

$R^4$ is selected from the group consisting of hydrogen and fluoro;

is selected from the group consisting of (a)
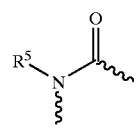

(b)
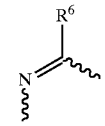

(c)
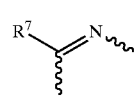

(d)
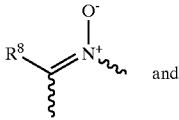
and (e)
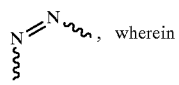, wherein

Z is selected from the group consisting of (i)
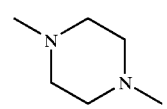

(ii)
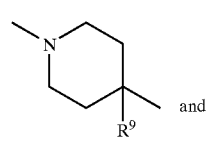
and

-continued

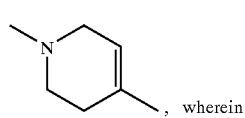, wherein

R⁹ is selected from the group consisting of hydrogen, hydroxy and cyano.

38. A process for the manufacture of a compound of formula I or a pharmaceutically acceptable salt thereof, comprising reacting a compound of formula

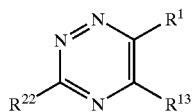     IIf wherein $R^{22}$ is $(C_1-C_7)$-alkyl and $R^{13}$ is halogen, with a compound of formula

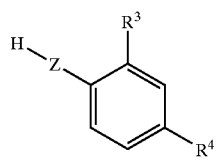     III to obtain a compound of formula

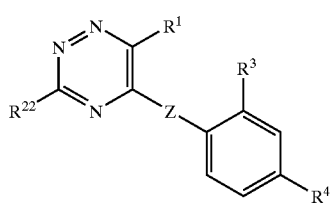     Ie-2 wherein $R^{22}$ signifies $(C_1-C_7)$-alkyl and
$R^1$ is selected from the group consisting of nitro and cyano;

$R^3$ is selected from the group consisting of hydrogen, $(C_1-C_7)$-alkyl, fluoro, hydroxy, $(C_1-C_7)$-alkoxy, $(C_1-C_7)$-alkylthio, cyano and nitro;

$R^4$ is selected from the group consisting of hydrogen and fluoro;

is selected from the group consisting of

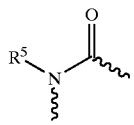     (a)

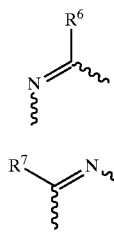     (b)

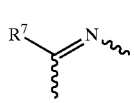     (c)

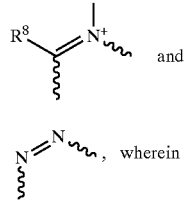     (d)

and

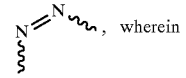, wherein     (e)

Z is as defined in claim 1,
and converting a compound of formula Ie into a pharmaceutically acceptable salt.

* * * * *

UNITED STATES PATENT AND TRADEMARK OFFICE
CERTIFICATE OF CORRECTION

PATENT NO. : 6,673,795 B2
DATED : January 6, 2004
INVENTOR(S) : Alfred Binggeli et al.

It is certified that error appears in the above-identified patent and that said Letters Patent is hereby corrected as shown below:

<u>Title page,</u>
Item [54], Title, reads "PYRIMIDINE, PYRAZINE AND TRIAZANE DERIVATIVES" should read -- PYRIMIDINE, PYRAZINE AND TRIAZINE DERIVATIVES --.

<u>Column 68,</u>
Line 24, "and converting a compound" should read -- and optionally converting a compound --.

<u>Column 74,</u>
Line 41, "and converting a compound" should read -- and optionally converting a compound --.

Signed and Sealed this

Fourth Day of May, 2004

JON W. DUDAS
*Acting Director of the United States Patent and Trademark Office*